US011535843B2

(12) United States Patent
McBrine et al.

(10) Patent No.: US 11,535,843 B2
(45) Date of Patent: Dec. 27, 2022

(54) PHAGE ENGINEERING: PROTECTION BY CIRCULARIZED INTERMEDIATE

(71) Applicant: The Charles Stark Draper Laboratory, Inc., Cambridge, MA (US)

(72) Inventors: Connor McBrine, Somerville, MA (US); Jason Holder, Swampscott, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 794 days.

(21) Appl. No.: 15/994,002

(22) Filed: May 31, 2018

(65) Prior Publication Data

US 2018/0346905 A1 Dec. 6, 2018

Related U.S. Application Data

(60) Provisional application No. 62/513,707, filed on Jun. 1, 2017.

(51) Int. Cl.

| | |
|---|---|
| ***C12N 15/10*** | (2006.01) |
| ***C12N 15/90*** | (2006.01) |
| ***C12N 7/00*** | (2006.01) |
| ***C12N 9/22*** | (2006.01) |
| ***C12N 15/113*** | (2010.01) |
| ***C12N 15/86*** | (2006.01) |

(52) U.S. Cl.

CPC .......... *C12N 15/1072* (2013.01); *C12N 7/00* (2013.01); *C12N 9/22* (2013.01); *C12N 15/1037* (2013.01); *C12N 15/1058* (2013.01); *C12N 15/1086* (2013.01); *C12N 15/113* (2013.01); *C12N 15/86* (2013.01); *C12N 15/902* (2013.01); *C12N 2310/20* (2017.05); *C12N 2795/10243* (2013.01)

(58) Field of Classification Search

CPC ................................................ C12N 15/1072

See application file for complete search history.

(56) References Cited

U.S. PATENT DOCUMENTS

2014/0274806 A1* 9/2014 O'Hagan ............ A61K 39/145 506/17

FOREIGN PATENT DOCUMENTS

| | | | | |
|---|---|---|---|---|
| WO | WO-2016/100389 A1 | | 6/2016 | |
| WO | WO-2016100389 A1 | * | 6/2016 | .............. C12N 7/00 |
| WO | WO-2017/172645 A2 | | 10/2017 | |

OTHER PUBLICATIONS

Makarova et. al., Evolution and classification of the CRISPR-Cas systems. 2011 Nat Rev Microbiol. 9(6): 467-477 (Year: 2011).*

Weigel et. al. Bacteriophage replication modules. FEMS Microbiol Rev 30 (2006) 321-381 (Year: 2006).*

Ando et al., Engineering Modular Viral Scaffolds for Targeted Bacterial Population Editing. 2015, Cell Systems1, 187-196 (Year: 2015).*

Koonin et al. Diversity, classification and evolution of CRISPR-Cas systems. 2017. Current Opinion in Microbiology, 37-67-78 (Year: 2017).*

International Search Report and Written Opinion on PCT PCT/US2018/035420 dated Dec. 3, 2019.

Jia-Wang Wang et al: "CRISPR/Cas9 nuclease cleavage combined with Gibson assembly for seamless cloning", Biotechniques Rapid Dispatches,vol. 58, No. 4, Apr. 1, 2015 (Apr. 1, 2015), XP055385711.

Marie-Laurence Lemay et al: "Genome Engineering of Virulent Lactococcal Phages Using CRISPR-Cas9", ACS Synthetic Biology, vol. 6, No. 7, Mar. 30, 2017 (Mar. 30, 2017), pp. 1351-1358, XP055503259,Washington, DC,USA.

* cited by examiner

*Primary Examiner* — Nancy J Leith
*Assistant Examiner* — Tiffany Nicole Grooms
(74) *Attorney, Agent, or Firm* — Foley & Lardner LLP

(57) ABSTRACT

The present disclosure provides methods of generating recombinant bacteriophage genomes. Specifically, the present technology provides methods of integrating a heterologous nucleic acid sequence into a linear bacteriophage DNA genome, and isolating recombinant bacteriophages that express the heterologous nucleic acid sequence.

12 Claims, 17 Drawing Sheets

Specification includes a Sequence Listing.

FIG. 3

>NC_011043.1 Klebsiella phage K11, complete genome (SEQ ID NO: 1)
TCTCACAGTTTACACTTTTGGTTATCCCCCGGTACCCTCCAGTTCACCCAAAGTAACCTAGGGTACCCC
TCTTTACCTTTGGTTTAACCTTGGGTGGTACCTTGGGAATCCCTTAGGTGATACCATATGTTGGGGTAAT
GGTGACCTGAGGACACTATATGTTGATGTCTCTGTGTCCCTATCTGTTGGTACTCATTAAGTCACACCTC
AAGTCGCCACCTGAGGTTAGACCAGAGGTAACCACCTGAGGTTATACCTGAGACCATATACCTAAGGTGA
GCTGACTGCTCACGAGGTTCACCGTTTGACTAACGTTTAGCAGTGACTGTTAGTAGGTCACATTAAGAGA
GTCGGTGCTATTAGTAATAGCGGTAAGTATCTCGTTTAGCAGTCCCTGAGACACTGAGAGCGGGACAAGA
GGGTATCGGTGAGTCATCACTATAAGGGCTATTGGTGGTCAGTGTCAACACCATAATCAATTAGGACACA
CTATAGGGAGACACTTAAAGTATTACTATGAGACCATCACCATAAAGATCACTATCACTATAGGTCTAAC
TAAAAGTTTAACTTTAAGTGTTGACATTCAGATTCCTTTATGAGACATTAGCAACCGTTGAGAGACACAA
CGTCACCAACGACCAGACAATACCACGAGTTATCTGGTTAGACTGAGGGTCTCAAGTAGTCATCAACCGG
ACATACGAAAGTGGTTGACTCAACGATGAACAAGTAGTAAGATGTACCACAGATTCACGAAGCACCGCTC
TTTAACAATATGGATTAGTCGCTGATATGTACACCATGACATTAGTGTTTAACTAGTGGTTACATTCAGG
TCTCTGGCAAGGTACGTCCTGTCACCCTGAGAGTAGCCACGATGATAACCACTAACATCGAGGATACACA
GCATGGAAATCGTAATGCAGGCACTGAACCACGGGGTCATTATGACGACAGCACGGGACTACACCGGGGC
CACCAAATACATGGTGCAATACGGCTTACAGTTCACGGTGTTTGACTCGTTCCGTGAGGCACTGCAAGAT
TACACAGATTTGCGTCACCCATTTCGCAAGAGTGTGGGGACTAGCGGTTAACGACAGGTCATCCAAGCGG
TGGCCTGAAAGATAACCACTAACTGAAGGATATACACGATGATTTTCACTAAAGAGCCAGCAAATAAAGC
CTTCGTATTCGTAACCGCTTACCGTGGCTATGAGTCGCTCGAAGTTAACGAGAAGGTCCTCAAGGGTCTC
ATCCGCACCATTAAGACCTATCCGGGTGCTTACGGTAACATCCGCGATGAGAATGTTGTGGGATGCTTCA
AAGAGGCTGGCATGGAGTACGCAACGGAAGAGCGCACGCTCAAGGTTGAATGCACCGTTAAACAAGCGGC
TGAACTGGCGTGGCTGGCATGTAAGACCTACCATCAAGACGCTGTACTAGTGGTTAACTCACAGACCCAC
ACAGCCTCCTTATGGTCTATTGAGAACGTAGGGGAGTATCCTCAGGTATACCCACGCTTGAAAGAGGTGT
CTTTAGGTGGTACGCTGCAACAAGTTGATGCACCTAAGGGTGAATGCTATTCAGTCATCGACGGGCAATA
CTGGGAGGTGGCGTGATGGTTGACTATGGTCTCACACAAGAACACTTGAAGTTATACCGCACGGCCATGG
CATATGGTGCATCGTTCGGTTACTGTATGGCCCAACTGGCCCAGACCTACCGCACACGCAAGGTGATGTA
TGGTAACCCTGTTCGTAATTAGTGTGTACGCCCTGATTGTCCTGTACTTTGTGCGGGACTTTCGCAAGGG
CCTCAAGGTGCACAAAGCATCATTCAGTTACATGAAGTGGGGCGTGTTACCTCGCTTTACTGTACGGCTA
CCTAATGGCCGCTTTAAGGCTAACAAGGTAGGTATTTTCTATATCGCAACCCATTAACACATCGCACATA
AGGAAACAACCAAATGAACTACACCGACATGCAAGAGCGCTTAGACGTCGTCCGTAACCTGCCAATCTGT
GAACTCGACAAGCGCCAGCCGCTGCTGGTAGCACTCATGGCGGACATTGTGAACGCTGAGACGTCCGATG
GTGACGATACGGATAGCGGTTGGGGTCTGGAACGTCAGGACTACTGGCAAACCCTGAAGATTAAGGCCAA
AGATGCTGGGTTTAACCTGCTGGGCAACGGTCACTTCAGCGCAGCGTTTAAGCACGAGCTGCTACCGGGT
AGGGCCATTAAGGTTGGCTTTAAGAAAGAGGACTCAGGGGCCGCATACGTGGCTTTCTGCCGGATGCACC
AAGGACGGGTAGGGATACCTAACGTCTATCACGTAGCGCGTCACGCTGGGTGCTACACGGTGGTACTTGA
TGAGCTGGAACCGTGCCAGCGCAGTGGGAACGATGAGCACGAGCACTACGCAGACCTAGCGTATTACTTT
GTCGAAGGTGAATCGGACCCAGCGGACTACTCGGAGGGCGACCAGCCGTTTATTGAGACGTGCCAAATGA
TTCGCAAGTTCTTCTACGGGATTGCGTCCTTTGATATGCACAGCGGTAACATCATGTTCACCAAGGACGG
CAAGCCAGTGATTACCGACCCGGTGTCATTCTCAGCGGACCGGGACCGGGAGCCTTTCTCACTGGAACCT
GAGGACCTGCTCGCAGAGATTGAGCAGATAGCGCACGACAAGATGATCGAACGCTGTAAGCGCAACAAGG
CTAAGCGTGACCCGAACGGAGAGCTGCGCATCGCACGCCGTAAGGCCAATAAGGAACGTCGAGCACGCCG
TAAGGCACACGCTCGGTGGCGTAAGGAGCGCGAGCGTATTAACGCTGATGCCTTAAAGTTTGACCTTGCT
AAAATCGAGGAGCGGGTACTAGCGTGGCAAATGGGACCAGGCCTGGCGATACAAATGGGCAAGCCGTTAC
CACTCGACAACTACCTTCAGGGTAGACTTATGGGTTAACGAGGTGTATCTTAGGTGTCTCCGAACGGTGA
GGCACCCATAGATAAACTTTATCCACAAAGAGGCACACAATGAACGCATTAAACATTGCACGTAATGACT
TCTCCGAGATTGAACTTGCTGCTATTCCGTACAACATCCTCAGCGAGCACTACGGGGACAAGCTGGCACG
TGAGCAGTTAGCACTGGAGCATGAAGCGTACGAGCTTGGCGAACAACGTTTCCTGAAGATGTTAGAACGT
CAGGTGAAAGCTGGTGAGTTCGCTGACAACGCGGCCGCTAAGCCGCTGGTCTTAACGTTGCACCCACAGC
TGACCAAGCGCATTGACGACTGGAAGGAGGAGCAAGCAAACGCTCGCGGTAAGAAGCCTCGCGCATACTA
CCCGATTAAGCACGGCGTCGCCTCAAAGTTAGCTGTTAGCATGGGCGCTGAGGTGCTAAAAGAGAAGCGC
GGAGTGTCCAGTGAGGCAATCGCACTGCTGACCATTAAGGTCGTCTTGGGGACGCTCACAGACGCCTCAA
AGGCCACAATCCAGCAGGTATCCTCTCAGTTAGGCAAGGCTCTTGAGGATGAGGCCCGCTTCGGTCGTAT
CCGTGAGCAGGAAGCCGCATACTTCAAGAAGAACGTAGCGGACCAGCTGGACAAGCGAGTAGGCCACGTG

FIG. 3 (contd.)

TACAAGAAGGCTTTCATGCAGGTAGTCGAGGCCGATATGATATCCAAAGGGATGCTGGGCGGCGACAACT
GGGCGAGCTGGAAAACTGACGAGCAGATGCACGTAGGGACCAAGCTGCTGGAGCTACTCATTGAGGGAAC
TGGTCTGGTGGAAATGACCAAGAACAAGATGGCCGATGGCTCCGATGATGTAACCAGTATGCAGATGGTC
CAGCTGGCTCCGGCCTTTGTGGAACTCCTGAGCAAACGGGCAGGCGCACTCGCGGGTATCAGCCCGATGC
ACCAGCCGTGCGTAGTCCCTCCGAAACCTTGGGTGGAGACCGTAGGCGGTGGCTACTGGTCAGTCGGTCG
CCGTCCGCTGGCACTGGTGCGTACCCACTCCAAGAAGGCGCTGCGCCGCTACGCTGACGTGCACATGCCA
GAGGTATACAAGGCGGTAAACCTCGCGCAAAACACGCCGTGGAAGGTGAACAAGAAGGTGCTGGCGGTAG
TCAACGAGATTGTCAACTGGAAGCACTGCCCGGTAGGTGACGTCCCAGCGATTGAACGCGAAGAGTTACC
GCCGCGCCCGGACGATATTGACACCAACGAGGTGGCACGTAAGGCATGGCGCAAGGAGGCCGCAGCGGTC
TACCGTAAGGACAAGGCCCGCCAGTCTCGCCGTTTGTCGATGGAGTTCATGGTCGCACAGGCTAACAAGT
TCGCTAACCACAAGGCCATTTGGTTCCCGTACAACATGGACTGGCGCGGGCGTGTGTACGCTGTGAGCAT
GTTCAACCCACAGGGTAACGATATGACCAAGGGGATGCTGACGCTGGCCAAGGGTAAGCCAATTGGTCTC
GACGGGTTCTACTGGCTGAAGATTCACGGCGCAAACTGTGCAGGTGTCGACAAGGTTCCCTTCCCTGAGC
GCATCAAGTTCATCGAAGAGAACGAGGGCAACATTCTGGCGAGCGCAGCGGACCCGCTGAATAACACTTG
GTGGACCCAGCAAGATTCGCCGTTCTGTTTCTTAGCGTTCTGCTTCGAGTACGCAGGTGTTAAGCATCAC
GGCCTGAATTACAACTGCTCGCTGCCGCTGGCGTTCGATGGGTCCTGCTCTGGGATTCAGCACTTCAGCG
CGATGCTCCGAGATTCCATCGGTGGTCGTGCGGTTAACCTGCTGCCTTCTGATACCGTGCAGGATATCTA
CAAGATTGTGGCCGACAAGGTGAACGAAGTGCTCCACCAGCACGCCGTCAACGGGTCTCAGACCGTGGTC
GAGCAGATTGCTGACAAAGAGACTGGCGAGTTTCACGAGAAGGTGACTCTGGGCGAGTCCGTACTGGCTG
CGCAGTGGTTGCAATATGGTGTGACCCGCAAGGTGACTAAGCGTTCGGTCATGACGCTGGCATACGGTTC
CAAAGAGTTTGGCTTCCGCCAGCAGGTTCTTGAGGACACCATTCAGCCTGCTATTGACAACGGCGAGGGC
CTGATGTTTACGCACCCTAACCAAGCAGCTGGCTACATGGCTAAGCTGATTTGGGACGCTGTGACCGTGA
CCGTAGTGGCCGCTGTCGAGGCAATGAACTGGCTGAAGTCTGCCGCTAAGCTGCTGGCTGCTGAAGTCAA
GGACAAGAAGACCAAAGAGGTGCTGCGTAAGCGCTGCGCAATCCACTGGGTAACACCCGATGGCTTCCCG
GTGTGGCAGGAGTACCGCAAGCAGAACCAAGCGCGCCTGAAGCTGGTCTTCCTCGGGCAGGCCAACGTCA
AGATGACGTATAACACTGGGAAGGACTCCGAGATTGATGCCCACAAGCAGGAATCCGGCATCGCTCCTAA
CTTTGTTCACTCACAGGATGGCAGTCACCTGCGCATGACTGTAGTACACGCCAACGAGGTCTACGGATT
GACTCCTTCGCACTCATTCACGACTCCTTTGGGACCATTCCGGCTGACGCTGGGAATCTCTTTAAGGCAG
TCCGCGAGACGATGGTCAAGACCTACGAGGACAACGATGTAATTGCAGACTTCTACGACCAGTTTGCCGA
CCAGCTGCACGAGTCTCAACTGGACAAGATGCCTGCGGTTCCGGCCAAAGGTGACCTGAATCTGCGCGAT
ATCTTGGAGTCTGACTTCGCGTTTGCGTAAGGTCTCAGGCAATTAGGGCACACTATAGGGAACCTTCGAA
TGACCGAGGGTTCCATTACTTAAAGTCTTAACTTAAAGAATACTTAAAGAGGCACGCTATGACTTACTCA
ATCGTTGTAACCATCTTGTTAATCATCACCCTTACGCTCCTCATTAACACCATACGCAATTCACTACGCA
GCGAGGAGCGGCTGGGGCGCAAGGTCCAAGAGGCCAACTCCGCGTTTAGCAGTGAGTCCTGCAAGGTCCT
GCGTCTGGCAGACAGGGCTGACTCGCTCAGTAGACAGGTTCGTTACTTAGAGGGTGAGCTTGAGAGCGAG
AAACAGAAGGTGCGCGATGTGAACGAACTTCGAGAGCACCAGCGGGAACGCATGAAGTTTCTTCGTAAGT
CCCTGAAGGAAGCACAAGACGAGCTGATGATGGTCTCCGACCTGATTCACGTTAAGTTCACCGCAGTGTT
GCCAGACGGTACCCACTCTAAGACGATCTTTAAGTTAGGACTCGGGCCGTGTGGTCTGCACGTTAAGTCC
CTGCGCTGGACCGAGCTGGACGACCGCTATCTGATAGACCAGCTGTGCACCAACGGTGAGCGCAAGCAGT
TCGTCTACTACAAGAGCGAAGTAGTAGGGCGCATCGAGTTCCGCCACGGTAAGCTGTAATTAGGACCCAC
TATCAGGAACATACTCAAGGTCATCATTCGGTGGCCTTCATGAATGTCCCTTACTATCACAATCAGGAGC
AACACCATGTATCAGAACACAATCAATTTCGAGCGCAACCGTGAACGTCAGCAGACTGAGGGTTATATCC
CTAAGGGCCGCAAGCTGAACAAGACGAAGCGCGGCGGTGGCGTGAAGGGTTCCTTCCGTAACGCTAAGGG
TGACAGCGTTGTTAACCAAGAGAAATACTTCGTAGGAGCGTAACAAATGGCTACGGAAAAAAGATGGCTC
TTCGATGGAAGCACCTCACAATGGTCTCGTTTAGGAGCAGCGGAGCGTAGACTACTAGATACGACAGGCC
TGCACGTGGTCATGCTTGACGACCCATTCACTAACACCGTGCTGTTCAACGTATTCGAGCCACGCGGGTC
ACTTCTAATAAGTAAGCGGTTCAGCCACTGGTCGATTGACTCAGCGTCAGACTGGCTGGCAAAACTCACC
GCAGACTACTCGAGCTGGAAGTAATTAGGACACACTATAGGCAGACTCAAGGTCATCGGATTCCGGCGGC
CTTTATGATTGCTTATTGCACACTAAATGAACACTACACTTCGGAGACATCATCATGATGAACATTAAGA
CTAATCCATTTAAGGCCGTATCGTTCGTTCGCTCTGCTATCGAGAAGGCGCTGGAGACTTCCGGTTACCT
CATCGCAGACACTAAGCATGATGGTGTACGCGGGAACATTTGCGTAGACAACACGGCTAACTCATCGTGG
CTCAGCCGGGTCTCCAAGACCATTCCGGCCCTTGAGCACCTCAACGGTTTCGACCAGCGCTGGCAGAAGT
TACTGAAAGATGACCGCTGGATTTTCCCGGATGGCTTCATGCTTGATGGTGAACTCATGGTCAAAGGCGT
GGACTTCAACACCGGGTCTGGCCTGCTGCGCACCAAGTGGCTCAAAGAGACCAACTGGATGTACTCCAGC
AAGGATGGAGTGGTGAAGGGCAAGAAGGAACCTTTCGAGCTGGATACCAAGCAACTAAAAGTTGTCCTCT

FIG. 3 (contd.)

ATGATATCATTCCGCTTGACATTATCGAGTCCGGTGATGACTACAACGTGATGACCCTCCTCCGCCTTGA
GCATGTCAAGGTAGCCTTACCAGTCCTGCAAGACCACTTCCCTGAAGTCGAGTGGTGCCTCTCGGAGTCC
CATGAAGTTTACGACATGGACGAACTCGAAGCGCTGTACCGACAGAAACGTGAAGAAGGTCACGAAGGTC
TGGTGGTCAAGGACCCTCAGGGCATCTACAAGCGTGGTAAGAAGTCCGGCTGGTGGAAGATGAAGCCAGA
GAATGAAGCTGACGGTGTAGTTGTGGGACTCAACTGGGGAACTCCCGGTCTTGCCAACGAGGGCAAGGTG
ATTGGCTTCGAGGTCCTCCTTGAGTCTGGTCGCGTGGTATCCGCCAACAACATCTCTCAGGCACTTATGG
AGGAGTTCACAGCCAAAGTTAAGGCCCACACCATGTGCGCCAATGGTTGCCGGATGTCTAAGGATGTCGG
TATGGATAATCACTCCTGCGCTGGCAAGTGTGCTTACGACCAACACCCGTCGAATAACCCTTATGAGGGC
TGGGCGTGCCAAATCAAGTACATGGAGGAAACTCCAGACGGCTCCCTGCGTCACCCGACCGTTCGACAAA
TGGCGTGGCACTGAGGCTGACCCGACCATCAAGATGTAATTAGGACCCACTATAGGAGACACCAAATGTC
TATCAACCTGATTCTAATCATCGTGCTCATCCTCGCGGCTATCGTGTGGTCAATGAATGACGAGCCACCT
AAAGGAGCATAAACCATGCGCTTACACTTCAATAAATCCAACGGTATCTTCTCGGTTCGCCGGGAGGACC
GCAGCACTGTAGCGGCCACCGAGCGCCACGGTAAGATTCCACGTATCGGCGACACCTTCGAGCTGGCACC
TAGCGTTCACATCTTGGTTACTCGCGGTCTCTACGAATTGGCTCAGACCAAGAGCCGTCCTTTCGTACCC
GTTGTGGTAACCAAGTGGCCACGCCTTCGTCTGTTCTGGGAGCGCATCAAGGAGGTGGTCAATGACTGAA
CGTGAAATTCAAGTTGTGGACCTTCTGGTTGGGCAAAACACTGACCGCCCAGACTCCACAACGTGCGCTG
ATGGCGTCATATGCTACAAGGTATCGTGTAGCGAGTGTCCGCTAAACGTCAAAGGTACGACCATTGGGGA
GGTCCGTACAATGAAGGACAGCAAAGGCTCCGCCCACTTCCCGGAGTGCAAGATATGGAACGGCGCTGGT
CAGTGTACCTGCGAGCCGACCCGAGACGACGGTGTTAAGCAGCCGAGCCACTACCAGCTGTTCGACGGTG
TCGAGGCCATCGAGGTGATTGCTCGCAGCATGACCCAAGAGATGTTTAAGGGGTACTGCCTCGGGAACAT
CCTCAAGTACCGCCTTCGGGCCGGGAAGAAGTCCGAGCTGGCTACCTTAGAGAAAGACATGGCGAAGGCC
GCTTTCTATCTGGAGCTGTACACCAAGCACAAGGGTCTGTGTTATGACGCCAAGTGAGTGGGCAAGAAAG
ATGTACGAGAAGACGCTCGACCCTGCGTACATCACCCTGTATAACATGTGGAAGGAGCGAGAAGATGCAA
AAGTTCGTCGTAACGGTCGAGACAGCTAACGCATCGTACGAACTCCCGGTACACGCTGGGTCTCTTGATG
AGGCCCTCGAAGTTGCCGAGGCGGAGTACGAAGAGTTAGGCCAAGTGACTCGGGTACGCCCGGATAGTCA
TTAGGACACACTATAGGGACACAGGTTGTCCCTCTTTCTGTTATAAACCAAAGGAGATTCACCATGGCAT
TCGCTAAGAAGAAAATTTACACCACCAAGATTGGTACCTGTGAGCCGTACGCTTACTTCAACAAGCCGGA
CTATGGCGGTGAGGGTTTTGAGAACCCACGTGGTACCTACAAAGGTTACGTAACGTTCAAGAACGAAGAC
TGTCAGGAGCTGGTAGACCTCATCGTTAAGACCCATGAGGAAAACTACGCCGCTCGTCTGGAAGCGCACG
AAGCGAACCCGCCTAAGGTTCAGAAGGGTAAGAAACCTCTGAAGCCGTATGAAGGCGACATGCCGTTCTT
CGATAACGGTGACGGCACCACCACGTTCAACTTCAAGTGCTACGGTTCGTACGAGGACAAGAAGACTGGC
GAGACCAAGAAGATTGTTCTGGGCGTAGTAGACGCGAAGGGCAAGCGCATTCAGGACGTTCCGATTATCG
GTGGCGGCTCCAAAGTGAAGATTCGCTTCTCGCTGGTACCGTACGGCTGGTCTGCGGTAGCTGGCGCTTC
CGTTAAGTTGCAGCTGGAAGGCGTGATGCTGGTCGAACTGGCTACCTTTGGTGGTGGCGAAGACGACTGG
GCTGACGAAGCCGTAGAAGGCGGTTACGAAGCGGACGAATCTCGCAGCCGTAAACCTCAGGAAGACCCGG
AAGACTGGTCTGGTGAGGAAGCTGACGAGGGCGAAGCCGAAGAAGACGATGACTTCTAATGGCGGGCTAT
GGGGCCAAAGGGATTCGGAAGGTGGGTGCCTTCCGGTCTGGCCTTGAGGACAAGGTGTCCAAGCAGTTAG
AAGCAAAGGGCGTCACGTTCGATTACGAATTGTGGCGCATCCCTTACGTTATTCCTGCGAGTGACCACCT
TTACACTCCAGACTTCTTGTTACCCAACGGTATCTTCGTGGAGACTAAGGGTCTCTGGGAAGCCGAGGAC
CGCAAGAAGCACCTACTGATTCGTGAGCAGCACCCGGAGTTAGACATCCGGTTAGTGTTCTCTTCGAGTC
GCACTAAGATTTACAAAGGGTCACCAACCAGTTACGCTGAGTGGTGTGAGAAGCATAACATCTTGTTTGC
CGACAAACTGATTCCCGTAGACTGGCTGAAGGAGCCGAAGCGTGATGTACCGTTCGGCAAGTTCAAGCAG
AAGAAAGGAGCAAAGTAAGTATGGCCAAGGTTCAATTCACTAAGCGACAGGAGACCTCTCAGATTTTCGT
TCACTGTTCCGCCACCAAGGCAAACATGGACGTAGGCGTCCGTGAGATTCGCCAGTGGCACAAAGAGCAG
GGCTGGCTGGATGTAGGGTATCACTTCATCATCCGTCGTGACGGTACCGTTGAGGCGGGCCGCGACCAAG
ACGCTGTGGGTTCACACGTCAAGGGATACAACTCGACCTCTGTCGGTGTGTGTCTGGTAGGTGGTATCGA
CGCCAAGGGTAACCCCGAGGCAAACTTCACGCCTCAGCAGATGAGCGCACTGAATGGGTTGCTGCACGAG
CTGAGGGGGACCTACCCCAAGGCTGTCATTATGGCGCACCACGATGTAGCGCCGAAGGCTTGTCCTAGCT
TCGACCTGCAACGTTGGGTAAAGACTGGCGAGCTGGTCACTTCTGACCGTGGGTAAACATTAGGGCACAC
TACAGGGAGACAATTACGTTTCCCTGTTGTCACACATTCTGTACAAATTATGGTCAGGCTAAGGTGCACT
TGGCGTAGCGCTGCGTTTCATTCGGGTTCGATTCCCGGACTGACCACACCAACGGAGATTACTTTATGAA
CAAGTTCAAAGAACACTTTGCTGACTCATGGCCACTGTATGTGTACGCATCGGCATTCATCATTGGCGCA
CTGCGAGTGTTGCTCCCATGAGTTACGGGGACAGTCGAGAAGACGGTCAGGAAAGTATCTTCCTGTTCCA
CGCTCCGTGCGAAAACTGTGGTTCTTCTGATGGTAACTCAGTGTACTCTGACGGGCATGAGTATTGCTTC
GTGTGTCAACACCGGGTTCCCGGCTCAGAGGAACGTACCGAAAAGTTATCATCGAGAAGACCCAAAGGAG

FIG. 3 (contd.)

GGAATTACGGGATGAATACACAAGGCTCAGGACTACTGGTATTCGGCGAGAGTGACGGTCGGTACACTGA
CCTGACTGCTCGTGGTATCTCAAAGGCGACATGCCAGAAGGCTGGCTATTGGGTCGCCAAGGTCAGAGGA
ACCGCCTATCAGGTGGCCGACTATCGTGACCAGAATGGCTCCATCGTCTCCCAGAAGCTGAGGGACAAGG
AGAAGAACTTCTCTACCCGAGGGTCCCACAAAGGGGATGCACTGTTTGGTAAGCACCTATGGAATGGTGG
TAAGAAGATTGTCATCACCGAGGGTGAAATCGACATGCTAACCGTGATGCAACTACAGGACTGTAAGTGG
CCTGTGGTTTCTCTCGGTCACGGTGCGTCAGCCGCTAAGAAAACTTGTAGTGCAAACTACGAGTATTTTG
ATAGCTTCGACCAGATTATCCTGATGTTCGACATGGATGACCCCGGTCGGGCAGCTGTAGAGGAAGCCGC
TCAGGTTCTCCCTCCCGGTAAGGTGCACGTAGCTGTGCTGACCGAGAAGGATGCCAACGAGTGTTTACTC
AAAGGTAAGGGAAAGGAGGTTCTCGACCAGATATGGAACGCGGCACCTTGGGTACCTGATGGTGTCATCG
GTGCGATGTCCATGAAGGACCGAGTGCGTGAGGCCATGACCAGCGAACAAAGCGTAGGATACCTTTTCTC
GGGATGCCCGGGACTGAATGACCGAACCTTGGGTGCACGTGGTGGCGAAGTCATCATGGTCACTTCTGGG
TCAGGAATGGGTAAGTCTACGTTCGTTCGTCAGCAGGCTCTAGGGTTCGCCAGAGGGCAAGGACTGAGGG
TAGGCATGGCGATGCTTGAGGAGTCCGTAGAGGAGACCATGGAGGATGTCCTAGGGATTGCTAACGGAAT
CCGCTTACGGCAGCAGCCTCGGGAGTTCAAGCAGAAACTCATTGAGGATGGTACGTACGATGAGTGGTTC
GATGAGCTGTATGGCTCCGACCAGTTCCATCTCTACGACTCCTTTGCGGAAGCTGAGGTGGACCGCCTGC
TGGCCAAGCTGCACTACATGCGCACAGGGTTGAACTGTGACGTAATCATTCTGGACCACATCTCAATCGT
AGTGTCTGCCTCGGAGGAATCCGATGAGCGCAAGATGATTGACCGACTCATGACCAAGCTGAAAGGGTTC
GCTAAGTCAACCGGAGTGGTACTTATTGTTATTTGCCACCTGAAGAACCCGGAGAAAGGTAAAGCTCATG
AAGAAGGACGTGCTGTTTCCATTACTGACCTGCGTGGGTCTGGGTCTCTGCGCCAGCTCTCTGATACTAT
CATTGCACTTGAGCGTAATCAGCAAGGGGATATGCCTAATCTTGTCCTCCTTCGTATTCTCAAGTGCCGC
TTTAATGGTATTGGCGTTGGCATTGCGGGGTACATGGAGTACAACGAAAAGACAGGACTCCTTGAACCGT
CTAGCTACACTGGCGGAGAAGGAGAGGGAGATACTGGCTGGGAAGGCCACGAAGAAGACGATTACTAAAC
GTAAATGCAATGGGGCGTACTGCTGGTGCGCCTTTGACCCTGATTATCAATAACGGAAGGAGAGCCATCA
TGTTTAAACTTATCGAAGCATTAGGCCGTCTGGTCATCGCACTGTACGTACGTGAAGCCAAGGCACTGGA
CAAAGCGTCCAAGGTGGAAGCGAAAGCAGCCGCTAAGCTGGCTAAGGCAGCCGACAAGGCACGTCAGGCA
TCTCTGGATGCAACCGCAGAGGCAGCTAAAGTTGCCGCTAAAGCTCAGAAACTTAAGGAGTTCTTCTAAT
GACTACCAAAGTTAAATTCCCCGGCAATACCATTCAGCTGTCCGACACCGTTGACCAGTGGGGACGCAAG
GTTCACATCAACGTTCGCAACGACAAGGTCACTCTGGTCTACCGCTGGAAGGCCAAGAGCGATAATCGTG
CGCATACTCAGCGTGTGACCCTCGACGACACACAGGCAGCTCGGCTGCTGGCGTCCGTAGCTGTAGCCGC
TACTGTGGCCATAGGTGAGGACAAAGTGCGTGAGGCAATCCTGAGCAAAGAGGTTGGCGAAACGTCCGTG
CGTCTGGCCGAAGCGTCAGAAGTTAAGTGATAAACTCAAGGTCATTACTATATGTAGTGGCCTTTATGAT
TATACACACAACATATTGAGAGGACATTACCATGCGTAAACCTGAAGAGATTCGTAAAGAGATTGAAGCG
CTGAACAAAGAGCTGGCTGAGGCCAAGACCTATGAGGCTAAGCGTGACGCTGCTGTGCACATTCTGGAGA
ACTTAGGGTGGACCCACAGTGGCCACAAGGGCTGGCAGAAGCCTTCGCAAAAGTGGAGCGACTATAAGGC
TCCCCTGAAGGCTGGTGAGCTGGCAACTTGGGACGACAAGGTACTAGGTGGGATAGTGTACATACGCAGT
GTGGGCGATAAGTACGCTCAGGTGTCCCACGTTCGTGGTGTTAGTAGACTGGGAGCTGATGTACTGAACA
GTAGCTTTGCTGTCGAGAAGAGTAAGTTAACCGTGCGTCCTCGTGAGTATTTCATCGGGCGTCGTTAAGC
AACAGGAGACCACTATGTTAGTAACCGATATCGAGGCGAACAACCTCTTAGAGAAAGTCACTCAGTTCCA
CTGTGGTGTCATTTATGACTACAGTACGGACGAGTACGTATCGTATCGACCTTGGGACTTCTCAGCGTAT
CTCGATGCGTTGGAAGCTGAGGTGGCTCGTGGTGGTCTCATCGTATTCCACAACGGTCACAAGTACGATG
CCCCAGTGTTAACCAAGCTGGCCAAGCTCCAGTTAAACCGAGAGTTCCACCTGCCGCGTGAGAACGTAGT
GGACACGTTGGTGCTCAGTCGTTTACTGTTTGCGAACATTAAGGACTCCGACATGGCCCTGCTGCGTTCC
GGTAAGTTACCCGGTAAGCGCTATGGGTCTCACGCTCTGGAGGCGTGGGGTTACCGCTTGGGCGAGATGA
AGGGTGAGTACAAGGACGACTTCAAGAAGCTACTTGAGGAACAGGGAGAGGACTATGTTGACGGTGCTGA
GTGGATTAGCTTCAACGAGCCGATGATGGCGTATAACGTTCAGGACGTTGTGGTGACCAAGGCTCTCTTA
GAGAAGCTGCTGAGCGACAAGCACTACTTCCCACTGTTTGGTAGTAACACCATAGAGTTCTACACCTCAG
CGTACTGCTTGAGGTTCTGGGAGGAGGCTTGTGAGGCCGTCTGGTTGGAACATCGGGCCGCTTGGTTACT
CGCTAAGCAGGAGCGCAACGGATTCCCGTTCAACACCAAGGCCATTGAGGAGTTGTACGTTGAACTCGCT
GGTCGTCGTTCTGAACTCCTTCAGACACTTACCGACACTTTCGGAACTTGGTACCAACCTAAAGGCGGCA
CTGAGTTATTCCTGCACCCGCGCACTGGTAAACCTCTGGGTAAATACCCACGAGTGAAGTACCCGAAACA
GGGTGGTATCTACAAGAAACCCAAGAACAAAGCTCAACGAGAGGGTCGTGAACCCTGTGAGCTGGACACT
CGGGATTACGTAGAGGGTGCTCCATACACACCAGTAGAGCACGTTGTGTTCAACCCAAGTAGCCGAGACC
ACATTGCGCTCAAGCTGAAGGAAGCCGGATGGGTACCCACAGAGTTCACCGAAAAGGGTGCACCTAAGGT
AGACGACGAGGTCCTTGAGCATGTTCGTGTGGGGGACCCTGAGAAGCAGCGCTGTATCGACCTCATCAAA
GAGTACCTGATGATACAGAAGCGTATCGGTCAGGCGGCTGAGGGCGACAAAGCGTGGCTACGTTACGTTC

FIG. 3 (contd.)

AAGAGGATGGTAAAATCCATGGAAGTGTTAACCCTAATGGTGCAGTTACAGGGCGAGCAACGCATAGCTT
CCCTAACCTTGGTCAAGTTCCGGGCGTTCGTTCGCCGTATGGTGAGCCTTGTCGAGCAGCGTTCGGCGCA
GAGCATCACTTGGACGGACTTACCGGACAGCCTTGGGTTCAAGCAGGCATCGACGCCAGCGGACTCGAAC
TCCGTTGTCTGGCACACTTCATGTCTAAGTACGACGACGGGGCATATGCGGATGTCATTCTCAACGGTGA
TATACACACAGTCAACCAAACGGCGGCTGAGTTGCCAACACGTGATAACGCCAAGACATTCATCTACGGT
TTCCTCTATGGTGCTGGAGACGAAAAGATTGGACAGATTGTGGGCGCAGGTAAGGAACGCGGAAAGGAAC
TCAAGAAGAAATTCCTTGAGAACACCCCAGCAATCGCAGCCCTGCGTGAAGGAATCCAGCAGACCCTCGT
CGAGTCATCCCGATGGGTTGCCGGAGAGCAGAAGGTCAAGTGGAAACGACGCTGGATTAAGGGACTGGAT
GGAAGAAAGGTACACGTTCGGTCACCACATGCCGCGCTCAACACGTTGCTTCAGTCAGCGGGTGCGCTCA
TTTGTAAGCTGTGGATTGTCGAGACTGAAGAGTTGCTTCTTAAGGCAGGATTGAAGCACGGATGGGATGG
CGACTTCGCCTACATGGCGTGGGTTCACGATGAAATACAAGTGGCCTGCCGGACCTCAGAGATTGCACAG
CAGGTGATTGACATAGCGCAGCAAGCTATGCGTAACGTGGGAGACCACTTTAAGTTCCGTTGCCGTCTGG
ACACAGAAGGTAAGATGGGTCCGAACTGGGCCGTATGTCACTAATAATACAGGAGATTTATCATGGGTAT
TAACAAACAGTTTCGCGTAACGTTCGATGTAACGGCTACTATGAGTGATGACCAAGAGCGGGAGTTCCTT
GAGGACCTACTATCTCTTGCGTATGGCGTGGACGACAAACGTCAGGCGCACATTGTAACCGAAGCAATCA
CCAAAGGTCATGAGGCGGCACTGGCATTCGTCATGCAGAGTGGTCTGCGGGAAGCTATTAAGGACATCGG
TAAGGAGCTGAGCTGCTCCGCTGTGACAGTACGCTTCTCTCCGGCAACCGTGAGGGTGACTAAGTGAGCG
AGTACCTCAAAGTTCTGGCGGCCCTCAAGGGCTGCCCTAAGTCCTTCCAGTCGAACTACGTGCGGAACAA
CGCCGCGTTAGTCGCTGAGGCTGCGAGCCGTGGTCACATTTCATGTCTGACCATGAGTGGTCGTAACGGT
GGCGCTTGGGAAATTACCAGTGCCGGAGTGAAATTCCTTAAGGCCCATGGAGGTTGTCTATGAAAGACTT
TTTAGGTAACGATATCGAGATTGGCGACACCATTGTGTATGCTGACGCTGGTGGCCGTGGAGGCTCTTCG
GGTCTTAACAAGACAGTAGTTACCCGAATGACTGATAAACAGGTCATGGTGTACGAATCAACGTGGTCAA
AACTGTGGCGTCCGTTTGACCGTGTTGTGGTTGTTGCTAAGGGAGGTTCCCAATGAAGCACACATTGTTA
TCCTTCAGTGACTACCGGGCAACCCAGAAGATTGCCAAGGGTGTCCTTGTGATGGATGGTGACTGGTTGG
TATTCCAAGCCATGAGTGCCGCTGAGTTCGATGCCTCGTGGGAGGAGGAGATTTGGCACCGTTGCTGTGA
CCACGCTAAGGCCCGAGAGATTCTGGAGAACTCCATCGAGTCCTACAAGGGCCGCAAGAAGGCGTGGAAG
AATGCAGACGTTGTCCTAGCGTTCACTGACCGTGTCAACTGGCGCAAGCTGCTTGTGGACCCGACGTACA
AAGAGAACCGCGCAGTCGTCAAGAAACCTGTGGGTTACTTTGAGTTCCTTGAGTACGTCTTTGAGTCCTA
CACATGTGTCCTTGAGCCTCAGCTCGAAGGTGATGACGTGATGGGTATCATCGGGTCTAACCCTCTCGTG
TACAACTACGAGAAGGCCGTGCTGGTCTCCTGCGACAAGGACTTTAAGACCATCCCGGATTGTGATTTCC
TGTGGTGCACGACTGGTAACATCCTCGTTCAGACTCAGGAGACAGCCGACTACTGGCACCTCTTCCAGAC
TATCAAGGGTGACATCACCGATGGTTACGGTGGGATTCCCGGATGGGGAGATACCGCTGAGGACTTCCTC
AAGGAACCCTTCATTGTGGAGCCTGTAACGTCCGTGCTGAAGTCCGGTAAGAACAAGGGCCAAGAGGTAA
CCAAGTGGGTGAAACGCGCTCCTGAGCCGGGAGAGACGCTCTGGGACTGCATTAAGTCCATTGGTGCCAA
AGCAGGGATGACCGAAGCGGAAGTAATTAAGCAGGGCCAGATGGCTCGCATCCTCCGTTCTGATGAGTAC
AACATCGAGACTGGGGAGATTACTCTATGGCAACCGGGCAGCTGATTCTCATCGTCCTGACCATGGGCTT
AGTTGCTCGTGGTCTCTGGATGTTGGCCTTGATTATCAAGCAGATAGTCGAGCATAAAGCAGAGTGATAA
ACTCATGGGCACAATTAGGACCCACTATAGGGAAGTGCCCATTATGATTATTACTTAAAGATTACTTAGA
GAGGAGACTCAAATGTTAAAACCTATAGAGCACATCCTTAACAATCCTAATGACCTTCCTGACGTACCGC
GAGCTGTCAAGGAGTACCTACAGTCTCGCTTCAATGCTGACTTCCTGTATCAGTCAGAGGTCCGTAAGCT
GCGTGAGGCTGGCCACAGTGAGGAGTTCATCTCCGGTGTACTGTATGGTCACTACATGGCTTCTCGTGTC
CTTGACGAGATGGAGGGCCGCCAGCGTGCACTCAAAGAAGGAGATTGATTATGTGTTTCTCACCTAAGAT
GAAAGCACCTAAGGTCGACACAACGACTGTCCCTGAGCCAGCTCCGCTCACTGAGGAACCTAAGGGTATC
CAGTACGGTGGCGACGAAGACTCAAACAGCACCACTCCTGAGGTGTCAGGGCGTAAGTCACTCAAGGTGA
CCAAGACGACCGAGCCCACAGGGTCAGTCAGTAAAATCCGTAAGTCAGCTTTAGGAGGCTAACATGGGAC
TGTTCAAGAAAATCAAGAAGGCTATCTCCAAGGTAGTCAAGGCACCACTCAAGGCCGTGGGTCTAGCAGC
AGATGCGCCTAACGTGCAGACAGCCGCTGAGACACCTGTGGCAGCACCTCAGGAAGCACCGAAAGAGGTC
GTGGAGGACGTTGAGTCTTCAGCAGACACCGAGTCTGGTAAGAAGAAATCCCGAGCGTCTGGTAAGAAGT
CCCTCTCAGTTTCCCGCAGCTCAGGCGGTGGGATTAACTTATGATTGGTTACGGGGAGGGCTAACAAATG
GCAGAAGTTAAACTCGAAGGCTTCGCAGAGGAGGGAGCCAAGGCGGTGTATGACCGTCTGAAGAACGACC
GACAACCTTACGAGACACGAGCAGAGTCCTGTGCGCAGTACACGATTCCATCACTGTTCCCTAAGGACTC
CGATAACGCATCAACAGATTACACGACTCCGTGGCAATCCGTAGGTGCTCGCGGCCTGAACAACCTAGCG
TCCAAGCTGATGTTGGCCCTGTTCCCGATGCAGTCATGGATGAAGTTGACCATTAGTGAATACGAAGCGA
AGAACCTTCTGGGTGACGCTGAGGGTCTCGCTAAGGTCGATGAGGGCCTATCAATGGTAGAGCGAATCAT
CATGAACTACATCGAGTCCAACAGTTACCGAGTGACTCTCTTCGAGTGCTTGAAGCAACTGTGTGTGGCC

FIG. 3 (contd.)

GGGAACGCATTGCTGTACTTACCGGAGCCTGAGGGTTACACCCCGATGAAGCTCTATCGCCTGAACTCGT
ATGTGGTCCAGCGAGACGCTTTCGGTAACGTACTCCAGATTGTCACTCTCGACAAGATTGCGTTCAACGC
TCTCCCTGAGGATGTCCGCAGCCAAGTGGAAGCAGCCCAAGGTGAGCAGAAGGAAGACGCTGAGGTTGAC
GTCTACACCCACGTGTACCTGAACGAATCCGGGGATGGCTACTCGAAGTACGAAGAGGTTGCCGAAGCAG
TAGTACCGGGCAGCGAGGCTGAATACCCGCTCGAAGAGTGTCCGTACATTCCGGTCCGCATGGTCCGCAT
CGACGGTGAATCCTACGGTCGTTCCTACGTGGAAGAGTATCTGGGTGACCTCAAGTCCCTAGAGAACCTC
CAAGAGTCCATCGTGAAGATGGCGATGATTACCGCGAAGGTCATCGGTCTGGTAGACCCGGCAGGTATCA
CTCAGGTCCGCCGACTCACGGCAGCACAGTCTGGTGCGTTCGTACCGGGCCGTAAGCAGGACATTGAGTT
CCTCCAGCTGGAGAAGTCCGGTGACTTTACCGTAGCGAAGAACGTAAGCGACACCATTGAGGCTCGCCTA
TCGTATGCCTTTATGCTCAACAGTGCGGTACAACGTACAGGCGAGCGAGTCACAGCCGAAGAGATTCGGT
ACGTGGCGTCAGAGCTGGAAGATACCCTAGGCGGTGTCTACTCGATTCTATCGCAGGAACTCCAGCTGCC
TCTGGTAAGAGTGCTCTTGAAGCAACTACAAGCCACGCAGCAAATCCCGGAGTTACCTAAAGAGGCCGTC
GAGCCAACTATCAGCACTGGCCTTGAGGCTATCGGACGTGGTCAGGACCTTGACAAGCTGGAGCGGTGCA
TTGCCGCATGGTCAGCCCTTAAGGCCCTCGAAGGTGATGACGACCTCAACTTGGCTAACCTCAAGTTACG
TATCGCTAACGCTATTGGACTCGACACTGCTGGTATGCTTCTCACTCAGGAGCAGAAGAACGCCCTTATG
GCACAGCAAGGTGCTCAGATTGCCACACAGCAAGGGGCCGCAGCGCTGGGTCAAGGGATGGCCGCACAGG
CTACTGCAAGTCCTGAAGCGATGGCCGCAGCAGCTGATTCAGTAGGTATGCAACCGGGCATGTAATTAGG
GCACACTATAGGGAGACCGATTGGTTTCCCTCTTAGTCTTAACTTTAAGGAGATTGAAATGGCTGGCGAA
TCTAACGCAGACGTATACGCATCCTTCGGTGTTAACAGTGCTGTACTGACTGGTAGTACACCTGAGGAGC
ACCAAGAAAACATGTTGGCTCTTGATGTTGCTGCCCGTGATGGCGATGATGCAATCGAGCTGAACACAAA
CAGTGATGACCCGTATGGTTCCGATGTGGACCCGTTCGGTGAACCTGAAGAGGGCCGTATGCAGGTCCGT
ATCTCCGCTGACGGTTCAGACGAACAGGACGGCGAAGAGGGTCAGGGTGACGAAGAACAGCAGGGCGACG
AAGAGAGTCAGCCGGAGGAAGTAACCGATGAAGGTGAACCTGAAGAGTTCAAACCTATTGGTGAAACTCC
GGCTGACATCAACGAAGCCTCTCAGCAGCTGGAAGAACACGAAGCTGGCTTTAACGACATGGTTGCTACT
GCAATCGAACGCGGTCTCTCACAGGATGCTGTGACCCGTATTCAGCAGGAGTACCAGAACGAGGACAGTT
TGTCCGACGAGTCTTACCGAGAGCTGGCCGAGGCGGGCTACAGTAAGGCGTTCGTCGATGCGTACATTCG
CGGTCAGGAGGCTCTGGTCAACCAGTACGTTGAGAAAGTGATGGACTTCGTGGGAGGCCGTGAGCGATTC
CAGCAGGTCTACAGTCACATGCAGACCAATAACCCTGAGGGTGCCGAGGCGCTCATCAAGGCTTTTGAGT
CTCGTGATGTAGCCACCATGAAGACGATTCTGAACCTAGCGGGACAGTCTCGTGATAAAACCTTTGGTAA
GAAAGCTGAGCGCTCTATTGCCAAGCGTGCAACCCCAGCGAAACCTGCTCCCCGCAAGGCTGTAGGCTTC
GAGTCTCAAGCTGAGATGATTAAGGCGATGTCCGACCCGCGCTACCGCACCGACTCTAAGTATCGTCGTG
AAGTAGAGCAAAAGGTAATCGACTCAACGTTCTAATGAATTAGGGCACACTATAGGGAGACCATCAGACT
GAACACGGTGACGTCCACTGGCTCCCTTCGAGTTACACAATGAGTATCACCTCGTTTCAAGTAGTAACTG
ACGCGACCTTAGGGCAAGACCTTATGATAGGCGCGGAGAATCACCCCAAGAGCTTGGCAACGATAGGCCC
GTTTGGTCAGCGTAATGACTAATTCTATTCGTAAACAACATAAGGAGATTCAACATGGCTAACATGCAAG
GTGGACAGCAGCTCGGTACTAACCAAGGTAAAGGTCAATCCGCAGCAGACAAGCTGGCGCTATTCCTGAA
AGTATTCGGCGGTGAAGTCCTGACCGCATTCGCTCGTACCTCTGTGACCACCAACCGTCACATGCAGCGT
CAAATCAGCTCCGGTAAGTCCGCACAGTTCCCTGTGATTGGCCGCACCAAGGCTGCTTACCTGCAACCGG
GCGAGTCTCTGGATGACAAACGTAAAGACATCAAGCACACCGAGAAGACCATTAACATTGATGGCCTGCT
GACCGCTGACGTGCTGATTTACGACATCGAAGACGCGATGAACCACTATGACGTGCGCTCCGAGTACACC
TCTCAGATTGGTGAATCTCTGGCGATGGCGGCGGATGGTGCGGTTCTGGCTGAGCTGGCTGGTCTGGTTA
ACCTCGCTGATTCCGTCAACGAGAACATCGCGGGTCTGGGCAAACCGTCCCTGCTGGAAGTTGGTGCTAA
GGCTGACCTGACCGACCCGGTTAAACTGGGCCAAGCGGTTATCGCACAGCTGACCATTGCTCGTGCGGCC
CTGACCAAGAACTACGTCCCGGCGAACGACCGTACGTTCTACACCACCCCGGACGTGTACTCTGCGATTC
TGGCGGCTCTGATGCCTAACGCTGCGAACTATGCGGCTCTGATTGACCCTGAGCGTGGCTCTATCCGTAA
CGTGATGGGCTTCGAAGTCGTAGAGGTTCCGCACCTGACCGCTGGTGGTGCTGGTGATGACCGCCCGGAC
GAAGGCGCAGAAGCGACCAACCAGAAGCACGCCTTCCCGGCAACTGGCGGTAAAGTCAACAAAGAGAACG
TTGTGGGCCTGTTCCAGCACCGTTCCGCTGTCGGCACCGTTAAACTGAAAGACCTGGCTCTGGAGCGTGC
TCGTCGTACTGAGTATCAGGCTGACCAGATTGTTGCCAAGTACGCGATGGGTCATGGTGGTCTGCGTCCA
GAATCTGCTGGTGCGCTGGTTTTCACAGCAGCCTAAGCGTAAATACCTTTAGTGCTCGGACGGTAACTCC
GTCTGAGTATGAGGTACAGACTGTGGCCATTACTGGTGATTCACTTAAGGTGACACTTGGTGGGCTGGAG
GGAGTAACGGACTGGTCAACACTTGAGGTAACTTATGGTACTTCCGGGATTGCCAGCCACACTCGCCGGA
CCAACACGCTGTACTTCAAAGGAATCGCTGTGGGCGAAACTCTAGTGACTGTCAGCTTTGACGGGTCTGA
AAGGAAGTCCTTTAAGCTGGTCGTGACTAATTAAAACTAAGCCAAACCCCTTGGGGACCACTCACGGTCT
CTGAGGGGTTTTTTCGTTAGGAGCTTACATTATGAACATGCAAGATGCTTACTTTGGGTCTGCCGCTGAG

FIG. 3 (contd.)

CTGGATGCTATCAACGAGATGCTCGCAGCTATCGGTGAATCCCCGGTGACCACCCTTGACGAAGATGGTA
GCGCAGACGTAGCTAACGCTCGTCGTATCCTCAACAGGATTAACCGCCAGATTCAGTCTAAAGGTTGGGC
CTTCAACATCAACGAGTCGGCCACGCTGACCCCTGACGCGGACACTGGGCTTATCCCGTTCCGTCCGGCC
TACCTGTCCATCCTTGGTGGCCAGTACGTCAACCGTGGTGGTTGGGTGTACGACAAGTCCACAGAGACGG
ATACCTTCTCTGGGGCAATCACAGTGACCCTAATCACACTTCAGGACTACGACGAGATGCCTGAGTGTTT
CCGCCAGTGGATTGTCACCAAGGCCAGCCGTCAGTTCAACTCTCGGTTCTTCGGAGCGGAGGACGTAGAG
AACTCTCTGGCACAGGAAGAGATGGAAGCGCGTATGGCATGCAACGAGTACGAGATGGACTTCGGTCAGT
ACAACATGCTTGACGGCGACGCATACGTGCAGGGTCTCATCGGTCGTTAATCAGAAACTTAAGGAGGACC
AAATGGCTCTCGTATCACAATCAATCAAGAACCTCAAGGGAGGCATTAGCCAGCAGCCTGAAATCCTACG
GTACCCAGAGCAGGGTACACTTCAGGTCAACGGTTGGTCCTCCGAGACTGAGGGTCTCCAGAAGCGACCA
CCTATGGTGTTCATCAAGTCCCTTGGACCTAGGGGCTACTTGGGGGAAGACCCGTACATTCACCTCATCA
ACCGAGATGAATACGAGCAGTATTACGCAGTGTTCACTGGGAACGATGTTCGGGTATTCGACCTGTCCGG
CTATGAGTACCAAGTAAGAGGTGACCGCTCGTATATCTCAGTAGTCAACCCTAAGGATAACTTGCGGATG
ATAACCGTGGCCGACTACACGTTCATCGTTAACCGTACCCGACAGGTCCGCGAGAACCAGAACGTGACCA
ACGGTGGTACCTTCAGGGACAACGTGGACGGTATTGTCAACGTCCGTGGTGGCCAGTATGGTCGTAAGCT
CGAAGTGAACATTAACGGTGTATGGGTCAGCCACCAGCTGCCTCCGGGTGACAACGCTAAGGATGACCCG
CCCAAGGTTGACGCACAGGCCATTGCGGCTGCACTCGCTGACCTACTTCGTGTGGCCCACCCAACGTGGA
CATTCAACGTGGGGACTGGTTATATCCACTGCATCGCACCAGCTGGGGTAACTCTTGATGAGTTCCAGAC
GAGGGACGGTTACGCGGACCAGCTGATTAACCCGGTGACCCACTACGTTCAGAGCTTCTCTAAGTTGCCA
CTTAACGCGCCTGACGGGTACATGGTGAAGATTGTCGGGGACACGTCCAAGACTGCTGACCAGTATTACG
TGAAGTATGACGCTTCTCAGAAGGTCTGGAAGGAAACCGTGGGCTGGAACATCTCGGTCGGCCTTGAGTA
TCACACGATGCCTTGGACTCTGGTGCGTGCAGCTGACGGTAACTTTGACCTCGGGTATCACGAGTGGAGG
GACCGCCGTGCTGGTGACGACGACACTAACCCTCAGCCGTCCTTTGTTAACTCAACGATAACCGATGTGT
TCTTCTTCAGGAACCGCTTAGGGTTCATCTCTGGGGAGAACATCGTGCTTTCCCGCACCAGTAAATACTT
TGAGTTCTACCCGCCGTCAGTGGCCAACTATACGGACGATGACCCGCTAGATGTTGCCGTGAGTCATAAC
CGTGTGTCGGTCCTTAAGTACGCTGTGAGCTTCGCTGAGGAGCTTCTGCTGTGGTCCGATGAGGCTCAGT
TCGTCCTGTCGGCCAACGGTGTGTTATCCGCTAAGACTGCACAGCTGGACCTGACCACTCAGTTCGATGT
GTCAGACCGTGCGCGTCCTTACGGTATCGGCAGGAACATCTACTATGCGTCTCCTCGAAGCTCCTTTACG
TCCATCATGCGCTACTACGCGGTACAGGATGTAAGCTCTGTGAAGAACGCAGAGGACATGACGGCCCACG
TCCCGAACTACATCCCGAACGGTGTGTACAGTATCAACGGGTCCGGTACTGAGAACTTCGCGTGTGTGCT
GACCAAGGGTGCTCCCAGCAAGGTGTTCATCTACAAGTTCCTCTACATGGACGAGAACATTCGACAGCAG
TCATGGTCCCACTGGGACTTCGGAGATGGTGTGGAGGTGATGGCTGCAAACTGCATCAACTCAACGATGT
ACCTGCTGATGCGGAACGCCTACAACGTGTGGATAGCTGCTGTGGACTTTAAGAAGGAGTCGACTGACTT
CCCGTTCGAGCCTTACAGGTTCCACGTGGATGCCAAGCGGTCATATCACATCTCAGAGACTGCGTACGAC
ATCGAGACCAACCAGACGGTAGTGAACGTCAAGGACATCTACGGTGCGTCGTTCTCCAATGGTACGGTGG
CAATCTGCGAGAGTGACGGCAAAATCACCGAGTATGAGCCGATGGGTGACTCTTGGGATTCAACCCCAGA
CATCCGCATTAGCGGTGACATCTCTGGCAAGGATATCGTCATTGGGTTCCTGTACGACTTCCAATATGTG
TTCAGTCGGTTCCTCATCAAGCAGGAGCAGAACGATGGCACAACGTCCACAGAGGACGCCGGACGCCTAC
AACTTCGGAGAGCGTGGGTGAACTATCAGGACACTGGTGCGTTCACTGTGAGTGTCGAGAATGGCAACCG
TGAGTTCAACTATCTGGTCAACGCCAGAGTAGGCTCCACGGGTCTACGTCTTGGCCAGAAGGCAACGACC
ACTGGTCAGTATCGCTTCCCGGTGACAGGTAACGCCTTGTACCAGAAGGTGTCCCTGAGTTCCTTCAACG
CTTCCCCGGTGTCAATCATTGGGTGCGGCTGGGAAGGTAACTACAGCAGACGAGCCAACGGCATTTAACT
GAAGGAATCCTTATGGTGTGCTCAATTAGGGCACACTATAGGGAGACCACACTAAGAGGGGACTTAAAGC
ATGTACATAAGACAATCCACTAAAACTGACCTATTTGTGTTCAAGCCGTCCCGTGACGATAGACTTGAGG
CAGCAGCCTTGGGTATAGCTCCGGGATTCCCACCGCATACCGAATGTGTCTCACTGGTTACCGATGGTGA
CATAGAGGGCACATACAACCTTCTGGCTATTGGAGGCAACGTGGGTGACCAAGTGTGGTTCGTAACGGAC
CAGAAGGTATCACGCTTGACCAGAGAGGAGCGTTTAGAGTTTCGTAAGAACATTATCGAATACCGCGACA
GGTTACACGAGAAGTACCCAATCCTCTGGAACTACGTGTGGGTAGGTAACAAGTCGCACATTCGGTTCCT
GAAGACAATTGGTGCTGTATTCGAGAATGATTTTACACTCAACGGCACCTTCCAACTGTTCACCATAACG
AGGAGGTAACTATGTGCTGGATGGCAGCTATTCCTATCGCAATGACGGCGGTGCAGGCCATCGGCCAGTC
ACGCAATGAAGCCAAGATGATTGGCCTTCAGAATGACCAGATGCGCCGACAGTCTGCCCAGATGATTAAA
GAGTCAAACATTCAGAACGCTAACGCCAGCCTTGAGCAGAAGCAGAAGCTGGAAGAAGCCAGTTCGGACC
TGACCGCTAAGAATCTCGATAAGGTTCAGGCCATGGGTACAATCCGTGCAGCAATCGGAGAGGGAAACCT
TGAGGGTGCCAGCATGGACCGTATCAGTCGAATCGAGGAGGGCAAGTTCATTCGGGAGGCCAACGCGGTC
ACCGATAACTACCGTCGAGACTATGCGTCACTGTTCGCTCAGCAGCTGGGCAACTCAGAGTCAACTATTG

FIG. 3 (contd.)

ACCAAGTTAAGTCCATGCAGAAGGCTGAGGGCAAAGGTAAGTCTAAGCTGGAACAGGTGCTGGACCCGCT
GGCATTGATGACCTCACAAGGCGCATCCGCATATTCGTCAGGTGCGTTCGACAGTAAGGGAACCAAGGCA
CCAATTAGTCAGGCCCAAGGTACTAAGGTAGGAGGTAAGTAATGGCCAGTAAATTAGAACAAGCATTAAG
CCAACTGCCGCAGGCCGGGTCTACCCGCATCCGTGGTGGCTCAGCGTCCATGCAGTATCGCCCAGTAACC
ATCCAACAGGAAGGGTTCCGTCAGTCCAACCTCGTGCAGTCCTTGGCGAAGTTTGGTACTGCGGTGGGTG
AGGCAGCGGATGCCTACGACAAGCGCCAACGGGACAAGGCCGATGAGCGGTCCGACGAGATTATCCGCAA
GTTGACCCCAGAGCAGCGCCGGGAGGCAATCAAGAACGGGACCCTGCTGTATCAGGATGACCCGTACGCT
ATGGAGGCCCTACGGTTCAAGACTGGTCGTAACGCAGCGTTCCTCATTGACGACGAAGTGGCACAGCGTG
TTCAGAACGGTGAGTTCCGTACCCGTGCTGAGATGGAAGAGTACCGCCACAAACGGTTGACCGAAGGTGC
CAACGAGTTCGCTGAACAGTTCATGATTAACCCTGAGGACTCTGAGTTCCAGAGAGGGTTCAACGCGAAC
ATCACTGAGCGCAACATCTCGCTGTACGGTAAGCACGATACGTTCCTGAGCGAGCAGGCCCAGAAGGGTG
CCATACTGGCCTCGAAGGTGGAGCTGTCAGGTGTGCTCAAAGACCCTGCCGTTCTGGCCCGTCCAGAGTC
CGGTGAGTTCTTCCAGCGCTACATCGACAACGCACTTAAGACTGGGAGTATCCCTAGCGACGCTCAGGCA
CAGCAGGTCATCATCGGGTCCCTTAACGACGTCATTCAGCGTCCGGGTGCTACCAACTTCCTCCAGAGCC
TTGAGGGCCGCCCAGTCACCCTTAATGGGAAGACCACGACCTATAAGGAGCTGATGGGAGAGGAGCAATG
GAACGCCCTGATGGTCAAGGCCCAGTCAACTCAGTTCGACAATGACGCTAAGTTGTCTGAAGGTTTCCGC
CTTGGGATTACCAGCGCGTTGAACCAAGACGATACCAGCAAGGGCTGGGAGATGCTTCAGGGTGCCAAAG
CGGAACTTGACCGCCTGCAACCCGGTGAGCAGATGACCCCAGAGCGTGAGCGCTTGATTCAGGCTGAGGA
GCAGATGCAGGCCCGTTTCCGTCAGGAGGCCCAAGCCGCAGCCAAGGAGATGGACAAGCGTCAGAAGACC
ATCAACAAGAATCAGGTCATCGACCAGCAGTTCACCAAGCGTATCAACGGTCAGTACGTGTCCACCAGCT
ACAAGGACATGCCGACCAATGAGAACACCGGAGAGTTCACGCACAGTGACATGGTGAACTACGCTAACGG
TAAGCTGGCCGAGATTGACCAGATGCAGCTCACGGAGCAACAGAAGGACCGCATGAAGCTGAGCTACCTC
CGGGCAGACTCAGAGGGTGGAGCCTTCCGTACCGTTGTGGGCCAGTTGGTAACCGACGCCGGGTCTGAAT
GGTCTGCCGCTGTGATTAACGGTAAGTTACCGGAGGACACCACAGCGTTGAACAAACTGCGCACCATGCG
TAACACCGACCCGGACCTCTTCGCTGCACTGTACCCGGACAAGGCTGACTTGTTCCTGACGATGGACATG
ATGGATAAGCAGGGCATTGACCCGCAGATTCTCATCGACGCTGACCGTTCTCGCCGCAGTCTCACCAAGG
AGATGCAGTACGAGGACGATAAGGCGTGGGCGTCCCTGAAGAACAACTCAGAGTCCCCAGAGCTGTCCCG
CATTCCGGCTAGTCTGGATGGTATGGCCCGTAAGATTTACGACAGCGTCAAGTACCGTACAGGCAACAGC
GACATGGCGATGCAGCAGACCGACAAGTTCCTCAAGGAATCCACTGTGACCTTCAAGGGTGATGACGTGG
ATGGCGATACCATTGGTATTATCCCGAAGAACATCCTACAGGTCAGTGATGACCCTAAGAGCTGGGAGCA
GGGCCGAGACATCCTCGAAGAAGCCCGTAAGGGAATCATTGCGGCTAACCCTTGGGTGACCAACAAGCAG
CTGACGATGTACCAGCAGGGTGACTCTATCTACATGATGGACACCACTGGCACTGTGCGAATCCGCTACG
ACAAGGAGCTACTGACTCGCACTTATCAGGAACAGCAGCAGCGTCTGGCCAAGGAAGCCGAAGAGAAGGC
ACTGAAGGAAGCAACCAAGCGTGCACCTATCGCCGCAGCCACTCAGGCCCGTAAGGCCGCTGGTGAGCGT
GTCCGTGCGAAACGTAAAGCCACTCCGAAGTTCATCTATGGAGGTGGTGACCAATAATCATTAAGGAGAC
AACATGAGCTACGATAAGTCCAAACCTAGCGATTACGATGGCATCTTTCAGAAGGCAGCAGACTCTCATG
GGGTCTCCTATGACCTCCTGCGTAAGTTATCGTTTAACGAATCATCCTTCAACCCTAAGGCCGTCTCTAA
GACTGGCCCTAAGGGAATCATGCAGTTCACCCGCAACACGGCCCGAGCGATGGGCCTTAACGTGACAGAT
GGTGACGACGATGGGCGCTACAACCCTGAGTTAGCCATTGACGCTGGCGCTAAGCTGCTTGCGAGCCTCG
TTAAGAAGTACAATGGGGATGAGCTTAAAGCGGCCCTAGCGTACAACCAAGGGGAAGGCCCAGCAGGTGC
CCCTCAGCTCCAAGCGTACGACAAGGGAGACTTCGGGTCTATCTCGGAGGAAGGGCGTAACTACATGCGC
AAGCTGCTGGATGTGGCCAAGAGTCCGAACTCAGGCGCACTGGAGGCGTTCGGTGGCATCACCCCAAAGG
GTAAAGGGATTCCCGCAGAGGATGCCTTCAAGGGCATCGCTAAGGCTGGAAAGGTTGGTACCGAACTGCC
GGAGTCCCATGGGTTCGACATTGAGGGTGTAGCGCAGGAAGCACCAAACACTCCATACGCTAAGGACTTC
TGGGAGAAGACCGGGACTACTCTCGATGAGTATAACTCTCGGTCAACCTTCTTCGGGTTCGGGGACGCTG
CTGAGGCTCAGATTCAGAACTCCACATTAGGTGTGGCCTTCCGTGCTGCGCGGGCTGACGATGGGTACGA
TGTGTTCAAGGACACGATGACCCCGACTCGCTGGAACTCTTATGTTCCCTCCAAGGAAGACCTACAGAAG
CTGCGCGACTCTGGGCTACCTCCGAGCTACTACGGTGTGGTGACTGGTGGTGACGGTGAGAACTGGGATG
CACTCATCAAGCTGGCCAAGGATAACTTCGAGGCTGACCAACGGGCCGCTGAGGCTGGTACTGGGGCGAA
ACTCGCTGCTGGTATCGTTGGGGCTGGTGTAGACCCACTCAGCTATGTACCTCTGGTCGGTGTGGCCGGG
AAGGGACTCAAGGTTGTCAATAAGGCCCTGCTAGTAGGCGCACAGGCTGGGGCACTCAGTGTTGCCTCTG
AGGGAATCCGTACGTCAGTGGCTGGTGGCGAGGCTCACTACGCTGATGCGGCACTCGGTGGGTTACTGTT
TGGCGCTGGTATGTCGGCTCTCAGTGATGCTGTGGCGGCTGGTATCCGTAAGGCCCGTGGAGTCGATTCT
GTGAATGAGTTCGCTGGACCAGCACTCCGTATGGAAGCGCGAGAGACTGCCATCAACACTGGTGGTCATG
ACACCTCGACGCTACCTCCAGAGAACTTCTCGTTCGAGCAGGACCACAGAGGCGTTCCGTTTGCTGACCA

FIG. 3 (contd.)

CCCGACCGAAGAGGGAGCAGTGGTTCTGGCCAATGGTTCCATCCTGAGCGATACCAACCCGCTTAACCCA
AGGACTCAACGTGACTTCGCAGAGATTGACCCAGAGCGTGCAGCTCCCGGTATCAAACTCGGTGGGTTCA
CTGAGATTGGCCTGAAGACCTTAGGGTCCAAGGATGCTGGTGTACGTGCAATCGCTCAGGACCTCGTGCG
CTCTCCCACAGGGATGCAATCAGGGTCTAGTGGTAAGTTCGGTGCGACCGCTTCGGACATCCACGAGCGA
CTCCATGCGACTGACCAACGGATGTATAACCAACTGTATGACGCTGTTGACCGTGCCATGAAGGACCCAG
AGTTCTCCGTGGGCGAGCAGAAGATGTCACGCAGAGCCATCCGTCAGGAAGTCTACAAGCGTGCCTCATT
GGCGATTGAGCGCCCAGAGTTACAGGCTGATTTGACCAAAGGTGAACGTGAGGTGATGGACCTGCTGAAA
GAGCACTTCGACACCAAGCGTGAACTGATGGAACAGCCGGGTATCTTCGGTAACGCTAACGCCGTGAGCA
TCTTCCCCGGTAGTCGACACAAGGGTACTTACGTGCCTAACGTGTACGACAGGGGTGCCAAGGAACTGAT
GATGCAGAAGCTGGGCGGACCTGAAGGACTCCAACAGGCAATCGCTCAGAGCTGGCTTACCAGTTACCGA
GTGCGACCTGAGGTCAAGGCGCGTGTTGACGAGTACCTGATGGAACTCAACGGCTACAAGTCGGTAGACC
AAGTGACACCTGAGGTGGTCCAGAAGCACGCTATGGATAAGGCGTACGGTATCAGCCACACTGAGGACTT
CACAGCGTCCAGTGTCATTGACGACAACATCACAGGTCTGGTCGGTATCGAGAACAACTCGTTCCTTGAG
GCCCGTAACATGTTCGACAGCGACCTCCCGGTTACCTTACCGGATGGGTCAACCTTCAGCGTCAACGACC
TGAGGGACTTCGACATGGCACGGATTATCCCAGCGTACGACCGTCGAGTTAACGGTGATATCTCCATCAT
GGGCGGTAGCGGTAAGACCACGCAGCAGCTCAAGGACGAAATCATGGCGTTAGACAAGCGGGCTGAGCGT
AAGGGACAGCTGAAGGGCGAAGTGGAAGCACTGAAGGACACCGTTAAGATTCTCACGGGGCGTGCTCGTC
GTAACAACGATACAGCCTTTGAGACCGCCATGCGTACCCTGAACGACCTAGCGTTCTTCGCTAAGAACTT
CTACATGGGTCCGCAGAACCTCACAGAGATTGCTGGGATGTTGGCTAAGGGTAACGTTAAGGCGATGCTC
CACGGTATCCCGACGTTGCGTGACCTAGCCACCAGAACCTCTCCGGTGTCCGGTAGTGAACTCCGCGAAC
TCCATGGGGCGCTGTTCGGTAAGGAACTCGACCAGTTAATCCGTCCGGGGCGTGAGGATATCGTACAGCG
AATCCGCGAGGCTTCCGATACCAGTGGGGCCATGGCGTCAGTCATTGGCACCATCAAGTTCGGTACTCAG
GAGCTGTCGGCTCGTTCTCCTTGGACCAAGATGCTGAACGGTACGGCTAACTACATTCTGGACACTGCCC
GTCAGGGTGTGCTCGGTGATGTGGCTGGTGCGGCCCTAGGCGGTAAGGGTTCCAAGTTTGGCAAAGAGAA
CTTCCTCAAAGCTGCCTCTATCAGTCCTGAGCAGTGGAAGGGAATCAAGCAACTCTTTGTCGACCACGCA
ACTCGTGACGCTAACGGCCAGTTCACCATCAAGGACAAGAAGGCTTTCAGTCAGGACCCGAGAGCGATGG
ACCTGTGGCGTCTTGCCGATAAGGTTGCCGACGAGACCATGCTGCGCCCTCACAAGGTATCCCAGCAGGA
TTCCAAGGCGTACGGTGCTGGTGTCAAGATGGCTATGCAGTTCAAGAACTTCACCATCAAGTCACTCAAT
GCCAAGTTCATTCGGTCCTTCTACGAGGGCTACAAGAACAACCGCGCTATCGACATGGCGTTGACACACG
TGTTGTCTCTGGGTATCGCCGGGACTTACTTTGCGATGCAGGCCCACGTGAAGGCTTACGGCCTCCAAGA
GTCCCAACGTAAGGACTACCTGAAGAAAGCCCTGAACCCGACCATGCTGGGCTACGCAGCGTTGACTCGA
AGTTCCCACACTGGTGCCCCGCTGTCCATCGTTTCGATGATGGCTGGTGCCGCTGGGTTCCAAGACGCCA
ACATGCTGCGCTCCACCATCTTACCTAAGGAGGAACAATTCCAGAAGAAAGATGGAGCGTCCAAAGGTCG
AGCCGAGTCGAGCAACCTTGCGGGTAACTTAGGGTCTCAGGTCCCAGCTCTGGGTTACGTAGGGAACGTC
ATTGCTACCGCCAAGAACGCCTACGGTGTTGCTACAGCACCCAACAAGCCGACTGAGCGTGACTACATGA
CTGGCCTGATGAACTCCACCAAGGAGCTTGTTCCGAACGACCCACTGACCCAGCAGCTCATCATGAAAAT
CTATGAAGCCAACGGGGTCACCATCAAGCAGCAGCCGAAGCCTAACTAATTAGGACACACTATAGGGAGA
CCGATTGGTTTCCCCCCTTCTCATTCAACTAAAGGAGGTCACAATGGACCAAGACATTAAAACAGTCATT
CAGTACCCAGTAGGGGCCACTGAGTTCGACATCCCGTTCGACTACCTGTCCCGTAAGTTTGTCCGTGTGT
CGCTGGCAGCTGACGACAACCGCAGACTGCTGAGTAACATCACTGAGTACCGCTACGTGTCTAAGACCAG
AGTGAAGCTCCTTGTGGAAACTACCGGGTTCGACCGTGTGGAAATCCGCAGATTCACCTCAGCGTCTGAG
CGTATTGTTGACTTCAGCGACGGCTCCGTACTGCGGGCAACAGACCTTAACGTTTCTCAGATTCAGTCTG
CCCATATCGCAGAGGAAGCACGTGATTCAGCACTGTTGGCTATGCCGCAGGATGATGCTGGCAACCTTGA
TGCCCGTAACCGCAGAATCGTTCGGCTGGCTCCGGGTGTCGAAGGTACGGATGCAATCAACAAGAACCAG
CTGGACACCACCTTAGGTGAAGCTGGTGGCATCCTGTCGGAAATCAAACAGACCGAGAAGGACATTCAGG
ATTACATCGAGAACTTTGCAGATGACACCACGTCTCTCAAGGGAATCAACTGGGTGTATAACAATGGGTC
GGCCAATGGTGGCGAGACCTCCATCCTGATTACCCGCGAGGGGCCAGTGTTCGCTGTGCCTACCATTTAC
ATCAATGGGGACAGACAGTCTGTTGGTTACCACTACTCTTACGACTCCGGTGATAAGACCATTCACCTAG
TTAAGCCGCTAACTGCTGGAGACTTTGTGGAATGTGTTACCTCTGAGGGCGTACTGCCGCTGTCTAATCT
TCTGTCGACACCAGACGGGGCCAGTCAGATTGGCACTAAAAGCGGCCTGACTGTGCAAGACTACCTTAAC
GGCGTGAAGTCCGCTACCATCCTGCGCAACATTGAGCCAGTCATTGATGGACAGCGCATCGTCCTCTCTG
AGATTAGCCCTACTTTGGGGCCTAAGTCTGGAGGTACCTTGGTGTACGACCAGTCTGATACATCCTCTGT
GGACGACGGGTACACTGTTTTCGTGACAGCTGGCGGTAAACGGTGGAAGCGAGAAGAGTCCTACATTGAC
GTAGCGTGGTTCGGTCCTAACTTTGGCCTTGCCTTACAGACCGCTGTTAACCTCGTTGACAACTACGTGA
GAACTGTCGGTTTCTACAGTCGCAAGACCATCTACATTGCAGCTGGTACCTATACGACAGACCGTCAGGT

FIG. 3 (contd.)

GGACATTCCATCTTATGTCTCTGTGGTGGCCATAGGTAACGTTAGCATCAATGGTTCTGGGCTTCCAGTA
AACTCCTACGTACTCCGCATAACGAACAAGGTTGGTGGCATTGTCACAACCCACCACTCAGGGTGGAACC
TCGGGGCCGTAGGTGGGACCCTTCGTCTTGTAGGAAACGGCAACACCGGGCAAGTGGATGGGCTTTATGT
GGGCGGTGCGACTTCTATGAGCGACGTACGGAACGTTAGCCTTTACGCTGTGTCAACTTCGGGTGTTCGC
TATGGGCTAACATTTGGTAGCACCAACACTTACCTCTTCACGGCAACCAAATGCCACTTTGAGACGTCTC
TTGTAAACCTGTACATTCCGGGCACCACAAGCTCTAACTCAGGGGAGAAGATGGTATTCAATGATACTGT
GTTCGGTGGCTCATCTAGGAACCATGTAGAGGTAAGCACCCCAGGCATGGACCTCACGTTCAATAACTGC
TCTTTCGACTTCACAAGCGGTAGCGTCCTGTACGGGACAGAGACTTGGGGCTATGCGAAAGTAGGCATGA
ATAATTGCCACTTCGAGGGGTTCAATAGTTTGTGGATAAAGGTGGATGCCCCGCAAGGTGGATTCATTGG
GTCAAACCGAGCGATAACCGTATCAAACGCCACAGTCCTTCCTAGGCTTCGCTCCAACACTGCTGGAACA
AACTCGGCGAGCCGTATGCACATTGATGCCAAGTCTACCCCGGTGTATATCAGTGGGCTGGACCTACGGC
ACGAGGTCGTACCATACACCGAGGAAATCTTCATGGCTTCAGCTGAAACTACCCTGTCTCTGCAAGGATA
TCTTAAGGACCCGCATTTCCAGATTCCAAGTGCTGCGCACATTCAGAACCGTGGGTGGAACATCGCTGAC
GAAACAACTGGAACTGTTGTGAACAGCCCCGCAACCTTGGATTCCCTTACGCGATTTACATGCACCGAGA
GGAACGCGATGTCTGCGGCTGTGGTCGATGGTGGAACTTCTGGTAAGCTCTTAGCAATGACTGGAGCGGG
TGGGTATTTCACTCTGGTCACTAAAGGATTCATTCCGGTGAGTACGTTCCAACGGATTGGCGGAGCAATG
TCGATTCAGGCAGCAGCAAGTACCGGAAACATCCAGTGCACGCTTGGTGTCCAGTGGTTCGACTACGATG
GTAACCTAATCGGGACAGACCAAGCCTTTGCGATTAACATGCGTGAGGTGTTCAACAACTCTTCTCTACC
TAACTTCGCCGAAGGCAACAACCGCTTCATCTCTACATCTGCGAGAACATTCCGTGCGCCAGCGGGGGCC
GCTAAGTGTAAACCATTGTGGCGAATCTCTGGTCATACTGGCGTTGTGAACATCTCGAGATTAGCATCAT
TTGTTTTATAAGGAGACAACATGCTGAATGATTTAAACCAACCACGAGGCTCGACGCTGGGCCTCTTTAC
TCCAAACCTTCCGTTGAAGAAGCGGTTGGACACCTTACCAAACATTTTAGATTTTGATTCAGACAGCCTT
AACGATGATAGCACTCGGTTTCAAAAGGCTATTACAGCTGGTGTGAAATCTTTATACGTCCCAGAACCTC
AGTTCTTTGGCAACAATAAGCCTCTTAAAATTGCTAACGTTGACATTGTGACCAATATGCACATCTACGG
GAACGGCTCAGCGGGATACCGTCAGGTTGGCGGGGCCATCACCATCCTAGATGGAGCGGACTATGGGTTT
AAACTGGCTGGTGTCGACTCTCAGACGCGAAACATTGGAGGCCGCATTGACGGTCTCTCGTTCCAAGGTG
AGTTCCCAACGACCGTGGCCGACGCCATCCGGTGCCAATCTGCCAGTAGCTTCGCGCTGGTCAACCTCTC
GTTCAGGAACCTCTCCGGGTCCGCTCTGGACCTGCGTGACTTCATGGAGAGCCACATTGAGCACTGCTAC
TTTAACTCAGTAGGTTCCGACACAAAGAACCCAATCAACATCGGGGACTTCGTCGGGTCGGCTCCTTGGA
ACGTCAACAACCTGCACATTGAGAACAACACCTTCGGGTCATGTAGTGGGAACATTATCAACATTAGTGA
CTCAGCTAACGCCGACCTCATTTGGATTCTCAACAATAAATTCGAATGGGACTCGACCCCAGTAAGCCCC
AACGTTTCCAACAAGGCGGTGGCATACATCGGGCGAGCCGAGCGTGTAAATGTGTCCGGTAACGGCTTCG
TGTACTACTACCCGGCCCACAACAAGTACGATGCCCTTATCCGAGTTTCCGATAAGTCGGCCTATGGTAA
CTTGTTCTCTGATAATACCGCTTGGGGCTGTACGCCTCCTTCAGGTAGTGACCTCACTCCAGCGTTCTAT
TGGGACATTGCTGGTGGGTCGTCTGCGGGGTCTAACAACAAGGCTAACACAAACCTCCCTACGCGCTGCA
CCAGTATCCACTCTCAGGATATCGACGAGCCGCTGGTAAGGACTACTCCGGGTAACCGACCAAACCTCCA
GAGCATCGGGGCAATGTCTCCCGGATATCTCTCTGCGCACTCCTTAGGTGGGGCTAACGCTTCCAACTTC
TTTGTGCCAGACACTGGTGCTACCAAGTACGGTACGGTGCTAGAGGCTCAAACTGGTGGTGAGGTTCGCC
GCTTGTTCATTCCTAAGGACATTGTTAGCCAGCGTGCTTGCGTTCGAGTTCAGGCCAGAGTGATGCCGTC
GCCGACAGCTGATGCCCTTGTGGGGCTGACCTGTGACGGCTCCATTGTTTCCACCACAATCCAAGGCGCA
ACCCAAGACTACCATACGGTGGCGGCTGGTGGCGGCTGGCAGATTGTCGAGTGGCTCATCCCGGCGTCTA
GTTACACTGCGGGCCAGTTAATCTTCACGAACCGTAGTGACACCGTCAAGTTCAAACTTGATGGCGTCCG
TGTGTCACGTGCAGACTTCGTAGATGTGACGATTGCATGGAGTCCGACCCCAATCTCCGCAGGGTCTGTG
GTAAACACCACTGCATCAATCACTCGCGTAAGTTCCCACGTGGTCGGCACTAGTGGTCTGAAGACAGACG
GTACGTTAGGTGGCGCTGTTAGTAGCTCTTATTTCAACCGTGGGGCCAATACCTTAGTGGTACAGCTGGC
AGCACTCACAGCAGCCACTCCGTCAATCACTCAGGTTACGGTTAGGCTGTTCCTTAACTAAGGAGGTAAC
ATGTTGTCCCTAGACTTCAACAACGAAGTTATCAAGGCGGCTCCCATTGCGGGGGTCGCTGGGGCCGATG
GTGTAGCGAGGCTCTTCTGGGGCCTCTCACTCAACGAGTGGTTCTACGTCGCGGCAATCGCCTACACAGT
GGTTCAGATTGGTGCCAAGGTAGTCGACAAAATCATTGACTGGAAGAAAGCAAATAAGGAGTAACATATG
GACCTGATTAAGTTCCTCGAAATGTTAGATACTGAGATGGCTCAGCAGATGCTCATGGACCTGAAGAATC
CCGAGAAGCGAACCCCTCAGCTGTACAACGCCATTGGTAAACTACTGGAGCGCCATAAGTTCCAAATCTC
TAAGCTGACCCCTGACGTTAACATCTTGGGCGGACTGGCTGAGGGTCTGGAGGCTTACAACTCCAAGGTG
GGCGCCGATGGTCTGACAGACGACGATACGTTCACCCTACAGTGATATACTCAAGGTACTACTATATGTA
GTGCCTTTATGGATGTCATTGCACTACGCTAGGCGTTCCTACGTGAAATCTGAGAAACAACGGGAGGCAT
TATGCTGGAGTTCACAAAGAGAATCGTCCCGTATCTTGTGGCTATCATGGTGTTTGCCTTCGGGTGGCAC

FIG. 3 (contd.)

TTGGGGTCTCAATCTACGGACGCTAAATGGAAGGAGGTAGTACAGCATGAATACGTTAAGAAGCAAACGG
CTAGAGCTGAAACTCAGAAAGCGATTGACGCAATATCGGCTAAGTACCAAGCAGACCTTGAGGGGCTGGA
GGGCAGCACTGATAGGGTTATTGCTGATTTGCGTAGCGACAATAAGCGGCTGCGCGTCAGAGTCAAACCT
ACCAGTGTCGCCGCAGGACCAGACGGTCGATGCCTCGTTGATGGTTCCGTCGAACTACACGAAGCAACTG
CTCGAAGTCTTATCGCAATAACCCAGAAGGCCGACCTCAAAGAGAAGGCCCTACAGGACACTATTCGCAA
GCTACAGCGGAAAGGAGGTGAACATTGAGTAACTCTCAGCAAGCCAAGAACGCCTTAATCATTGCGCAAC
TGAAGGGTGACTTTGTCGCCTTTCTCTTCGTGCTCTGGAAGGCCCTGAACCTGCCGGAACCAACCAAGTG
TCAAATCGACATGGCCAAGTGTCTGGCGAACCCAAAGAACAAGAAGTTTATCCTTCAGGCTTTCCGTGGT
ATCGGGAAGTCATTCATCACGTGTGCGTTCGTAGTGTGGACCCTGTGGCGTGACCCTCAGTTAAAGATAC
TGATTGTCTCGGCCTCAAAGGAACGTGCGGACGCTAACTCCATCTTCATCAAGAACATCATCGACTTGTT
GCCTTTCCTGAGTGAGCTTAAGCCCCGCCCCGGTCAGCGTGACTCCGTGATTAGCTTTGATGTAGGCCCT
GCCAAGCCAGACCACAGCCCGTCAGTTAAGTCTGTGGGTATTACTGGTCAGCTTACTGGTAGCCGTGCTG
ATATCATCATTGCGGATGACGTGGAGATTCCCGGTAACTCTGCAACCCAAGGCGCTCGTGAGAAACTCTG
GACGCTGGTTCAGGAGTTCGCCGCACTGTTGAAACCTCTGCCGACTAGCCGTGTTATCTATCTGGGTACA
CCTCAGACCGAGATGACGCTCTACAAGGAACTTGAGGACAACCGTGGGTACTCCACCATTATCTGGCCTG
CACAGTATCCTCGCTCCAAAGAGGAGGACCTGTACTATGGCGACCGACTGGCCCCGATGCTCCGTAGTGA
GTACGATGAGGACAAAGAGGGCCTCAGCAGTCAGCCTACTGACCCGGTTCGATTCGACTCCATGGACCTT
CAGGAACGTGAGGTGGAATACGGCAAGGCTGGCTATACGCTTCAGTTCATGCTCAACCCGAACCTCAGTG
ACGCCGAGAAGTACCCGCTACGCCTCCGTGACGCTATCGTGTGCGGTCTACAGATGGACAAGGCCCCAAT
GCATTACCAGTGGTTGCCGAACCGTCAGAACCGCAATGAGGAGCTTCCTAACGTGGGCATGAAGGGTGAC
GAGATTTACTCCTTCCATACAGCCTCAAGTAACACTGGCGCGTATCAGGGTAAGATTCTGGTCATTGACC
CCAGCGGTCGCGGTAAGGATGAGACTGGCTGGTGCGTACTGTACACCCTCAACGGTTACATCTACTTGAT
GGACGCTGGCGGTACTCGTGGGTACGAAGAGAAGTCCCTTGAGTTCCTCGCTAAGAAAGCCAAACAGTGG
CAGGTTCAGACTGTGGTCTTCGAGAGCAACTTCGGTGACGGTATGTTCGGTAACGTGTTCCAGCCTGTGC
TCCTGAAGCATCACCCAGCGCAACTCGAAGAGATTCGTGCTCGTGGTATGAAAGAGGTCCGTATCTGCGA
TACCCTTGAGCCTGTACTGGCAAGTCACCGCTTGGTCATCCGTGATGAGGTTATCCGACAGGACTACCAG
ACGGCACGTGATGCAGACGGTAAGCACGCTCTGAAGTACAGTCTGTTCTACCAGATGACCCGTATGAGCC
GTGAGAAGGGCGCGGTGGCACACGATGACCGACTTGATGCGTTAGCATTGGGTGTCGAGTTCCTACGCTC
TACGATGCAGCAGGACGCTGTGAAGATAGAGGCTGAGGTACTTCAGGAGTTCTTGGAGCACCACATGGAG
AAGCCCCTGAGTAACATCTCCCAGTTCCGGGCCACCAGTAGCAACGGTGTGGACATCCGATGGGAAGACG
ATGGGGATGACACTATGTTCATCGCATGGTGATTATGCAGGGATTGTGCATAAGGATTCATTAGGCCACG
GAAGGCCACTTTGAGGAAACTCCATGTATAACAGACACTTGGAATTAGGACCCACTATAGGGAGAGACCC
TTGAAGACTTACTATAAGACAACTTAAAGATTCATTCATATAGTTATTCACTTTAAGTCTCCTTAAAGGC
AGAGGGTAGTGATGATAATATCACCCTCTCACTATAAGACACTAAGAGCCAACATAAGGAGGACCTATGC
GCTTATTGTTAACCTTACTGCGCCATAGGGCTACTTGGCGATTTCTGCTGGTACTTGCTGGTGCCCTTGG
GGCTTCACTGGTTACTCAGCAGCAACTCAGTGGACTGGAGACTCTCGTGTGCTCTCTACTCACTTGTAGC
GATTAGGGTCTTCCTGACGCGCTAGGGATTCCGTAGTGATGCTTATCAGCATACACCACTCCATCCCTCT
ACAGTCAATACTTAAAGTTAACCTTAGGTGATTCACTGGGTCTACCTACGGGTCTATGCAATGACCTGAG
GAGTACCTGAGGTTACCTTTAAGAATTTTACATAAAGTTCTGAGTGTACATCTCACAGTTTACACTTTTG
GTTATCCCCCCGGTACCCTCCAGTTCACCCAAAGTAACCTAGGGTACCCCTCTTTACCTTTGGTTTAACC
TTGGGTGGTACCTTGGGAATCCCTTAGGTGATACCATATGTTGGGGTAATGGTGACCTGAGGACACTATA
TGTTGATGTCTCTGTGTCCCT

SEQUENCE LISTING

<160> NUMBER OF SEQ ID NOS: 5

<210> SEQ ID NO 1
<211> LENGTH: 41181
<212> TYPE: DNA
<213> ORGANISM: Klebsiella phage K11

<400> SEQUENCE: 1
tctcacagtt tacacttttg gttatccccc cggtaccctc cagttcaccc aaagtaacct 60
agggtacccc tctttacctt tggtttaacc ttgggtggta ccttgggaat cccttaggtg 120
ataccatatg ttggggtaat ggtgacctga ggacactata tgttgatgtc tctgtgtccc 180
tatctgttgg tactcattaa gtcacacctc aagtcgccac ctgaggttag accagaggta 240
accacctgag gttatacctg agaccatata cctaaggtga gctgactgct cacgaggttc 300
accgtttgac taacgtttag cagtgactgt tagtaggtca cattaagaga gtcggtgcta 360
ttagtaatag cggtaagtat ctcgtttagc agtccctgag acactgagag cgggacaaga 420
gggtatcggt gagtcatcac tataagggct attggtggtc agtgtcaaca ccataatcaa 480
ttaggacaca ctatagggag acacttaaag tattactatg agaccatcac cataaagatc 540
actatcacta taggtctaac taaaagttta actttaagtg ttgacattca gattccttta 600
tgagacatta gcaaccgttg agagacacaa cgtcaccaac gaccagacaa taccacgagt 660
tatctggtta gactgagggt ctcaagtagt catcaaccgg acatacgaaa gtggttgact 720
caacgatgaa caagtagtaa gatgtaccac agattcacga agcaccgctc tttaacaata 780
tggattagtc gctgatatgt acaccatgac attagtgttt aactagtggt tacattcagg 840
tctctggcaa ggtacgtcct gtcaccctga gagtagccac gatgataacc actaacatcg 900
aggatacaca gcatggaaat cgtaatgcag gcactgaacc acggggtcat tatgacgaca 960
gcacgggact acaccggggc caccaaatac atggtgcaat acggcttaca gttcacggtg 1020
tttgactcgt tccgtgaggc actgcaagat tacacagatt tgcgtcaccc atttcgcaag 1080
agtgtgggga ctagcggtta acgacaggtc atccaagcgg tggcctgaaa gataaccact 1140
aactgaagga tatacacgat gattttcact aaagagccag caaataaagc cttcgtattc 1200
gtaaccgctt accgtggcta tgagtcgctc gaagttaacg agaaggtcct caagggtctc 1260
atccgcacca ttaagaccta tccgggtgct tacggtaaca tccgcgatga gaatgttgtg 1320
ggatgcttca aagaggctgg catggagtac gcaacggaag agcgcacgct caaggttgaa 1380
tgcaccgtta aacaagcggc tgaactggcg tggctggcat gtaagaccta ccatcaagac 1440
gctgtactag tggttaactc acagacccac acagcctcct tatggtctat tgagaacgta 1500

-continued

```
ggggagtatc ctcaggtata cccacgcttg aaagaggtgt ctttaggtgg tacgctgcaa   1560
caagttgatg cacctaaggg tgaatgctat tcagtcatcg acgggcaata ctgggaggtg   1620
gcgtgatggt tgactatggt ctcacacaag aacacttgaa gttataccgc acggccatgg   1680
catatggtgc atcgttcggt tactgtatgg cccaactggc ccagacctac cgcacacgca   1740
aggtgatgta tggtaaccct gttcgtaatt agtgtgtacg ccctgattgt cctgtacttt   1800
gtgcgggact ttcgcaaggg cctcaaggtg cacaaagcat cattcagtta catgaagtgg   1860
ggcgtgttac ctcgctttac tgtacggcta cctaatggcc gctttaaggc taacaaggta   1920
ggtattttct atatcgcaac ccattaacac atcgcacata aggaaacaac caaatgaact   1980
acaccgacat gcaagagcgc ttagacgtcg tccgtaacct gccaatctgt gaactcgaca   2040
agcgccagcc gctgctggta gcactcatgg cggacattgt gaacgctgag acgtccgatg   2100
gtgacgatac ggatagcggt tggggtctgg aacgtcagga ctactggcaa accctgaaga   2160
ttaaggccaa agatgctggg tttaacctgc tgggcaacgg tcacttcagc gcagcgttta   2220
agcacgagct gctaccgggt agggccatta aggttggctt taagaaagag gactcagggg   2280
ccgcatacgt ggctttctgc cggatgcacc aaggacgggt agggatacct aacgtctatc   2340
acgtagcgcg tcacgctggg tgctacacgg tggtacttga tgagctggaa ccgtgccagc   2400
gcagtgggaa cgatgagcac gagcactacg cagacctagc gtattacttt gtcgaaggtg   2460
aatcggaccc agcggactac tcggagggcg accagccgtt tattgagacg tgccaaatga   2520
ttcgcaagtt cttctacggg attgcgtcct ttgatatgca cagcggtaac atcatgttca   2580
ccaaggacgg caagccagtg attaccgacc cggtgtcatt ctcagcggac cgggaccggg   2640
agcctttctc actggaacct gaggacctgc tcgcagagat tgagcagata gcgcacgaca   2700
agatgatcga acgctgtaag cgcaacaagg ctaagcgtga cccgaacgga gagctgcgca   2760
tcgcacgccg taaggccaat aaggaacgtc gagcacgccg taaggcacac gctcggtggc   2820
gtaaggagcg cgagcgtatt aacgctgatg ccttaaagtt tgaccttgct aaaatcgagg   2880
agcgggtact agcgtggcaa atgggaccag gcctggcgat acaaatgggc aagccgttac   2940
cactcgacaa ctaccttcag ggtagactta tgggttaacg aggtgtatct taggtgtctc   3000
cgaacggtga ggcacccata gataaacttt atccacaaag aggcacacaa tgaacgcatt   3060
aaacattgca cgtaatgact tctccgagat tgaacttgct gctattccgt acaacatcct   3120
cagcgagcac tacggggaca agctggcacg tgagcagtta gcactggagc atgaagcgta   3180
cgagcttggc gaacaacgtt tcctgaagat gttagaacgt caggtgaaag ctggtgagtt   3240
cgctgacaac gcggccgcta agccgctggt cttaacgttg cacccacagc tgaccaagcg   3300
cattgacgac tggaaggagg agcaagcaaa cgctcgcggt aagaagcctc gcgcatacta   3360
cccgattaag cacggcgtcg cctcaaagtt agctgttagc atgggcgctg aggtgctaaa   3420
agagaagcgc ggagtgtcca gtgaggcaat cgcactgctg accattaagg tcgtcttggg   3480
gacgctcaca gacgcctcaa aggccacaat ccagcaggta tcctctcagt taggcaaggc   3540
tcttgaggat gaggcccgct tcggtcgtat ccgtgagcag gaagccgcat acttcaagaa   3600
gaacgtagcg gaccagctgg acaagcgagt aggccacgtg tacaagaagg ctttcatgca   3660
ggtagtcgag gccgatatga tatccaaagg gatgctgggc ggcgacaact gggcgagctg   3720
gaaaactgac gagcagatgc acgtagggac caagctgctg gagctactca ttgagggaac   3780
tggtctggtg gaaatgacca agaacaagat ggccgatggc tccgatgatg taaccagtat   3840
gcagatggtc cagctggctc cggcctttgt ggaactcctg agcaaacggg caggcgcact   3900
```

-continued

```
cgcgggtatc agcccgatgc accagccgtg cgtagtccct ccgaaacctt gggtggagac   3960
cgtaggcggt ggctactggt cagtcggtcg ccgtccgctg gcactggtgc gtacccactc   4020
caagaaggcg ctgcgccgct acgctgacgt gcacatgcca gaggtataca aggcggtaaa   4080
cctcgcgcaa aacacgccgt ggaaggtgaa caagaaggtg ctggcggtag tcaacgagat   4140
tgtcaactgg aagcactgcc cggtaggtga cgtcccagcg attgaacgcg aagagttacc   4200
gccgcgcccg gacgatattg acaccaacga ggtggcacgt aaggcatggc gcaaggaggc   4260
cgcagcggtc taccgtaagg acaaggcccg ccagtctcgc cgtttgtcga tggagttcat   4320
ggtcgcacag gctaacaagt tcgctaacca caaggccatt tggttcccgt acaacatgga   4380
ctggcgcggg cgtgtgtacg ctgtgagcat gttcaaccca cagggtaacg atatgaccaa   4440
ggggatgctg acgctggcca agggtaagcc aattggtctc gacgggttct actggctgaa   4500
gattcacggc gcaaactgtg caggtgtcga caaggttccc ttccctgagc gcatcaagtt   4560
catcgaagag aacgagggca acattctggc gagcgcagcg gacccgctga ataacacttg   4620
gtggacccag caagattcgc cgttctgttt cttagcgttc tgcttcgagt acgcaggtgt   4680
taagcatcac ggcctgaatt acaactgctc gctgccgctg gcgttcgatg ggtcctgctc   4740
tgggattcag cacttcagcg cgatgctccg agattccatc ggtggtcgtg cggttaacct   4800
gctgccttct gataccgtgc aggatatcta caagattgtg gccgacaagg tgaacgaagt   4860
gctccaccag cacgccgtca acgggtctca gaccgtggtc gagcagattg ctgacaaaga   4920
gactggcgag tttcacgaga aggtgactct gggcgagtcc gtactggctg cgcagtggtt   4980
gcaatatggt gtgacccgca aggtgactaa gcgttcggtc atgacgctgg catacggttc   5040
caaagagttt ggcttccgcc agcaggttct tgaggacacc attcagcctg ctattgacaa   5100
cggcgagggc ctgatgttta cgcaccctaa ccaagcagct ggctacatgg ctaagctgat   5160
ttgggacgct gtgaccgtga ccgtagtggc cgctgtcgag gcaatgaact ggctgaagtc   5220
tgccgctaag ctgctggctg ctgaagtcaa ggacaagaag accaaagagg tgctgcgtaa   5280
gcgctgcgca atccactggg taacacccga tggcttcccg gtgtggcagg agtaccgcaa   5340
gcagaaccaa gcgcgcctga agctggtctt cctcgggcag gccaacgtca agatgacgta   5400
taacactggg aaggactccg agattgatgc ccacaagcag gaatccggca tcgctcctaa   5460
ctttgttcac tcacaggatg gcagtcacct gcgcatgact gtagtacacg ccaacgaggt   5520
ctacgggatt gactccttcg cactcattca cgactccttt gggaccattc cggctgacgc   5580
tgggaatctc tttaaggcag tccgcgagac gatggtcaag acctacgagg acaacgatgt   5640
aattgcagac ttctacgacc agtttgccga ccagctgcac gagtctcaac tggacaagat   5700
gcctgcggtt ccggccaaag gtgacctgaa tctgcgcgat atcttggagt ctgacttcgc   5760
gtttgcgtaa ggtctcaggc aattagggca cactataggg aaccttcgaa tgaccgaggg   5820
ttccattact taaagtctta acttaaagaa tacttaaaga ggcacgctat gacttactca   5880
atcgttgtaa ccatcttgtt aatcatcacc cttacgctcc tcattaacac catacgcaat   5940
tcactacgca gcgaggagcg gctggggcgc aaggtccaag aggccaactc cgcgtttagc   6000
agtgagtcct gcaaggtcct gcgtctggca gacagggctg actcgctcag tagacaggtt   6060
cgttacttag agggtgagct tgagagcgag aaacagaagg tgcgcgatgt gaacgaactt   6120
cgagagcacc agcgggaacg catgaagttt cttcgtaagt ccctgaagga agcacaagac   6180
gagctgatga tggtctccga cctgattcac gttaagttca ccgcagtgtt gccagacggt   6240
```

-continued

```
acccactcta agacgatctt taagttagga ctcgggccgt gtggtctgca cgttaagtcc   6300
ctgcgctgga ccgagctgga cgaccgctat ctgatagacc agctgtgcac caacggtgag   6360
cgcaagcagt tcgtctacta caagagcgaa gtagtagggc gcatcgagtt ccgccacggt   6420
aagctgtaat taggacccac tatcaggaac atactcaagg tcatcattcg gtggccttca   6480
tgaatgtccc ttactatcac aatcaggagc aacaccatgt atcagaacac aatcaatttc   6540
gagcgcaacc gtgaacgtca gcagactgag ggttatatcc ctaagggccg caagctgaac   6600
aagacgaagc gcggcggtgg cgtgaagggt tccttccgta acgctaaggg tgacagcgtt   6660
gttaaccaag agaaatactt cgtaggagcg taacaaatgg ctacggaaaa aagatggctc   6720
ttcgatggaa gcacctcaca atggtctcgt ttaggagcag cggagcgtag actactagat   6780
acgacaggcc tgcacgtggt catgcttgac gacccattca ctaacaccgt gctgttcaac   6840
gtattcgagc cacgcgggtc acttctaata agtaagcggt tcagccactg gtcgattgac   6900
tcagcgtcag actggctggc aaaactcacc gcagactact cgagctggaa gtaattagga   6960
cacactatag gcagactcaa ggtcatcgga ttccggcggc ctttatgatt gcttattgca   7020
cactaaatga acactacact tcggagacat catcatgatg aacattaaga ctaatccatt   7080
taaggccgta tcgttcgttc gctctgctat cgagaaggcg ctggagactt ccggttacct   7140
catcgcagac actaagcatg atggtgtacg cgggaacatt tgcgtagaca acacggctaa   7200
ctcatcgtgg ctcagccggg tctccaagac cattccggcc cttgagcacc tcaacggttt   7260
cgaccagcgc tggcagaagt tactgaaaga tgaccgctgg attttcccgg atggcttcat   7320
gcttgatggt gaactcatgg tcaaaggcgt ggacttcaac accgggtctg gcctgctgcg   7380
caccaagtgg ctcaaagaga ccaactggat gtactccagc aaggatggag tggtgaaggg   7440
caagaaggaa cctttcgagc tggataccaa gcaactaaaa gttgtcctct atgatatcat   7500
tccgcttgac attatcgagt ccggtgatga ctacaacgtg atgaccctcc tccgccttga   7560
gcatgtcaag gtagccttac cagtcctgca agaccacttc cctgaagtcg agtggtgcct   7620
ctcggagtcc catgaagttt acgacatgga cgaactcgaa gcgctgtacc gacagaaacg   7680
tgaagaaggt cacgaaggtc tggtggtcaa ggaccctcag ggcatctaca agcgtggtaa   7740
gaagtccggc tggtggaaga tgaagccaga gaatgaagct gacggtgtag ttgtgggact   7800
caactgggga actcccggtc ttgccaacga gggcaaggtg attggcttcg aggtcctcct   7860
tgagtctggt cgcgtggtat ccgccaacaa catctctcag gcacttatgg aggagttcac   7920
agccaaagtt aaggcccaca ccatgtgcgc caatggttgc cggatgtcta aggatgtcgg   7980
tatggataat cactcctgcg ctggcaagtg tgcttacgac caacacccgt cgaataaccc   8040
ttatgagggc tgggcgtgcc aaatcaagta catggaggaa actccagacg gctccctgcg   8100
tcacccgacc gttcgacaaa tggcgtggca ctgaggctga cccgaccatc aagatgtaat   8160
taggacccac tataggagac accaaatgtc tatcaacctg attctaatca tcgtgctcat   8220
cctcgcggct atcgtgtggt caatgaatga cgagccacct aaaggagcat aaaccatgcg   8280
cttacacttc aataaatcca acggtatctt ctcggttcgc cgggaggacc gcagcactgt   8340
agcggccacc gagcgccacg gtaagattcc acgtatcggc gacaccttcg agctggcacc   8400
tagcgttcac atcttggtta ctcgcggtct ctacgaattg gctcagacca agagccgtcc   8460
tttcgtaccc gttgtggtaa ccaagtggcc acgccttcgt ctgttctggg agcgcatcaa   8520
ggaggtggtc aatgactgaa cgtgaaattc aagttgtgga ccttctggtt gggcaaaaca   8580
ctgaccgccc agactccaca acgtgcgctg atggcgtcat atgctacaag gtatcgtgta   8640
```

-continued

```
gcgagtgtcc gctaaacgtc aaaggtacga ccattgggga ggtccgtaca atgaaggaca   8700
gcaaaggctc cgcccacttc ccggagtgca agatatggaa cggcgctggt cagtgtacct   8760
gcgagccgac ccgagacgac ggtgttaagc agccgagcca ctaccagctg ttcgacggtg   8820
tcgaggccat cgaggtgatt gctcgcagca tgacccaaga gatgtttaag ggtactgcc    8880
tcgggaacat cctcaagtac cgccttcggg ccgggaagaa gtccgagctg gctaccttag   8940
agaaagacat ggcgaaggcc gctttctatc tggagctgta caccaagcac aagggtctgt   9000
gttatgacgc caagtgagtg ggcaagaaag atgtacgaga agacgctcga ccctgcgtac   9060
atcaccctgt ataacatgtg gaaggagcga gaagatgcaa aagttcgtcg taacggtcga   9120
gacagctaac gcatcgtacg aactcccggt acacgctggg tctcttgatg aggccctcga   9180
agttgccgag gcggagtacg aagagttagg ccaagtgact cgggtacgcc cggatagtca   9240
ttaggacaca ctatagggac acaggttgtc cctctttctg ttataaacca aaggagattc   9300
accatggcat tcgctaagaa gaaaatttac accaccaaga ttggtacctg tgagccgtac   9360
gcttacttca acaagccgga ctatggcggt gagggttttg agaacccacg tggtacctac   9420
aaaggttacg taacgttcaa gaacgaagac tgtcaggagc tggtagacct catcgttaag   9480
acccatgagg aaaactacgc cgctcgtctg gaagcgcacg aagcgaaccc gcctaaggtt   9540
cagaagggta agaaacctct gaagccgtat gaaggcgaca tgccgttctt cgataacggt   9600
gacggcacca ccacgttcaa cttcaagtgc tacggttcgt acgaggacaa gaagactggc   9660
gagaccaaga agattgttct gggcgtagta gacgcgaagg gcaagcgcat tcaggacgtt   9720
ccgattatcg gtggcggctc caaagtgaag attcgcttct cgctggtacc gtacggctgg   9780
tctgcggtag ctggcgcttc cgttaagttg cagctggaag gcgtgatgct ggtcgaactg   9840
gctacctttg gtggtggcga agacgactgg gctgacgaag ccgtagaagg cggttacgaa   9900
gcggacgaat ctcgcagccg taaacctcag gaagacccgg aagactggtc tggtgaggaa   9960
gctgacgagg gcgaagccga agaagacgat gacttctaat ggcgggctat ggggccaaag  10020
ggattcggaa ggtgggtgcc ttccggtctg gccttgagga caaggtgtcc aagcagttag  10080
aagcaaaggg cgtcacgttc gattacgaat tgtggcgcat cccttacgtt attcctgcga  10140
gtgaccacct ttacactcca gacttcttgt tacccaacgg tatcttcgtg gagactaagg  10200
gtctctggga agccgaggac cgcaagaagc acctactgat tcgtgagcag cacccggagt  10260
tagacatccg gttagtgttc tcttcgagtc gcactaagat ttacaaaggg tcaccaacca  10320
gttacgctga gtggtgtgag aagcataaca tcttgtttgc cgacaaactg attcccgtag  10380
actggctgaa ggagccgaag cgtgatgtac cgttcggcaa gttcaagcag aagaaaggag  10440
caaagtaagt atggccaagg ttcaattcac taagcgacag gagacctctc agattttcgt  10500
tcactgttcc gccaccaagg caaacatgga cgtaggcgtc cgtgagattc gccagtggca  10560
caaagagcag ggctggctgg atgtagggta tcacttcatc atccgtcgtg acggtaccgt  10620
tgaggcgggc cgcgaccaag acgctgtggg ttcacacgtc aagggataca actcgacctc  10680
tgtcggtgtg tgtctggtag gtggtatcga cgccaagggt aaccccgagg caaacttcac  10740
gcctcagcag atgagcgcac tgaatgggtt gctgcacgag ctgaggggga cctaccccaa  10800
ggctgtcatt atggcgcacc acgatgtagc gccgaaggct tgtcctagct tcgacctgca  10860
acgttgggta aagactggcg agctggtcac ttctgaccgt gggtaaacat tagggcacac  10920
tacagggaga caattacgtt tccctgttgt cacacattct gtacaaatta tggtcaggct  10980
```

```
aaggtgcact tggcgtagcg ctgcgtttca ttcgggttcg attcccggac tgaccacacc  11040
aacggagatt actttatgaa caagttcaaa gaacactttg ctgactcatg gccactgtat  11100
gtgtacgcat cggcattcat cattggcgca ctgcgagtgt tgctcccatg agttacgggg  11160
acagtcgaga agacggtcag gaaagtatct tcctgttcca cgctccgtgc gaaaactgtg  11220
gttcttctga tggtaactca gtgtactctg acgggcatga gtattgcttc gtgtgtcaac  11280
accgggttcc cggctcagag gaacgtaccg aaaagttatc atcgagaaga cccaaaggag  11340
ggaattacgg gatgaataca caaggctcag gactactggt attcggcgag agtgacggtc  11400
ggtacactga cctgactgct cgtggtatct caaaggcgac atgccagaag gctggctatt  11460
gggtcgccaa ggtcagagga accgcctatc aggtggccga ctatcgtgac cagaatggct  11520
ccatcgtctc ccagaagctg agggacaagg agaagaactt ctctacccga gggtcccaca  11580
aaggggatgc actgtttggt aagcacctat ggaatggtgg taagaagatt gtcatcaccg  11640
agggtgaaat cgacatgcta accgtgatgc aactacagga ctgtaagtgg cctgtggttt  11700
ctctcggtca cggtgcgtca gccgctaaga aaacttgtag tgcaaactac gagtattttg  11760
atagcttcga ccagattatc ctgatgttcg acatggatga ccccggtcgg gcagctgtag  11820
aggaagccgc tcaggttctc cctcccggta aggtgcacgt agctgtgctg accgagaagg  11880
atgccaacga gtgtttactc aaaggtaagg gaaaggaggt tctcgaccag atatggaacg  11940
cggcaccttg ggtacctgat ggtgtcatcg gtgcgatgtc catgaaggac cgagtgcgtg  12000
aggccatgac cagcgaacaa agcgtaggat accttttctc gggatgcccg ggactgaatg  12060
accgaacctt gggtgcacgt ggtggcgaag tcatcatggt cacttctggg tcaggaatgg  12120
gtaagtctac gttcgttcgt cagcaggctc tagggttcgc cagagggcaa ggactgaggg  12180
taggcatggc gatgcttgag gagtccgtag aggagaccat ggaggatgtc ctagggattg  12240
ctaacggaat ccgcttacgg cagcagcctc gggagttcaa gcagaaactc attgaggatg  12300
gtacgtacga tgagtggttc gatgagctgt atggctccga ccagttccat ctctacgact  12360
cctttgcgga agctgaggtg gaccgcctgc tggccaagct gcactacatg cgcacagggt  12420
tgaactgtga cgtaatcatt ctggaccaca tctcaatcgt agtgtctgcc tcggaggaat  12480
ccgatgagcg caagatgatt gaccgactca tgaccaagct gaaagggttc gctaagtcaa  12540
ccggagtggt acttattgtt atttgccacc tgaagaaccc ggagaaaggt aaagctcatg  12600
aagaaggacg tgctgtttcc attactgacc tgcgtgggtc tgggtctctg cgccagctct  12660
ctgatactat cattgcactt gagcgtaatc agcaaggggga tatgcctaat cttgtcctcc  12720
ttcgtattct caagtgccgc tttaatggta ttggcgttgg cattgcgggg tacatggagt  12780
acaacgaaaa gacaggactc cttgaaccgt ctagctacac tggcggagaa ggagagggag  12840
atactggctg ggaaggccac gaagaagacg attactaaac gtaaatgcaa tggggcgtac  12900
tgctggtgcg cctttgaccc tgattatcaa taacggaagg agagccatca tgtttaaact  12960
tatcgaagca ttaggccgtc tggtcatcgc actgtacgta cgtgaagcca aggcactgga  13020
caaagcgtcc aaggtggaag cgaaagcagc cgctaagctg gctaaggcag ccgacaaggc  13080
acgtcaggca tctctggatg caaccgcaga ggcagctaaa gttgccgcta aagctcagaa  13140
acttaaggag ttcttctaat gactaccaaa gttaaattcc ccggcaatac cattcagctg  13200
tccgacaccg ttgaccagtg ggacgcaagg gttcacatca acgttcgcaa cgacaaggtc  13260
actctggtct accgctggaa ggccaagagc gataatcgtg cgcatactca gcgtgtgacc  13320
ctcgacgaca cacaggcagc tcggctgctg gcgtccgtag ctgtagccgc tactgtggcc  13380
```

```
ataggtgagg acaaagtgcg tgaggcaatc ctgagcaaag aggttggcga aacgtccgtg  13440
cgtctggccg aagcgtcaga agttaagtga taaactcaag gtcattacta tatgtagtgg  13500
cctttatgat tatacacaca acatattgag aggacattac catgcgtaaa cctgaagaga  13560
ttcgtaaaga gattgaagcg ctgaacaaag agctggctga ggccaagacc tatgaggcta  13620
agcgtgacgc tgctgtgcac attctggaga acttagggtg gacccacagt ggccacaagg  13680
gctggcagaa gccttcgcaa aagtggagcg actataaggc tcccctgaag gctggtgagc  13740
tggcaacttg ggacgacaag gtactaggtg ggatagtgta catacgcagt gtgggcgata  13800
agtacgctca ggtgtcccac gttcgtggtg ttagtagact gggagctgat gtactgaaca  13860
gtagctttgc tgtcgagaag agtaagttaa ccgtgcgtcc tcgtgagtat ttcatcgggc  13920
gtcgttaagc aacaggagac cactatgtta gtaaccgata tcgaggcgaa caacctctta  13980
gagaaagtca ctcagttcca ctgtggtgtc atttatgact acagtacgga cgagtacgta  14040
tcgtatcgac cttgggactt ctcagcgtat ctcgatgcgt tggaagctga ggtggctcgt  14100
ggtggtctca tcgtattcca caacggtcac aagtacgatg ccccagtgtt aaccaagctg  14160
gccaagctcc agttaaaccg agagttccac ctgccgcgtg agaacgtagt ggacacgttg  14220
gtgctcagtc gtttactgtt tgcgaacatt aaggactccg acatggccct gctgcgttcc  14280
ggtaagttac ccggtaagcg ctatgggtct cacgctctgg aggcgtgggg ttaccgcttg  14340
ggcgagatga agggtgagta caaggacgac ttcaagaagc tacttgagga acagggagag  14400
gactatgttg acggtgctga gtggattagc ttcaacgagc cgatgatggc gtataacgtt  14460
caggacgttg tggtgaccaa ggctctctta gagaagctgc tgagcgacaa gcactacttc  14520
ccactgtttg gtagtaacac catagagttc tacacctcag cgtactgctt gaggttctgg  14580
gaggaggctt gtgaggccgt ctggttggaa catcgggccg cttggttact cgctaagcag  14640
gagcgcaacg gattcccgtt caacaccaag gccattgagg agttgtacgt tgaactcgct  14700
ggtcgtcgtt ctgaactcct tcagacactt accgacactt tcggaacttg gtaccaacct  14760
aaaggcggca ctgagttatt cctgcacccg cgcactggta aacctctggg taaataccca  14820
cgagtgaagt acccgaaaca gggtggtatc tacaagaaac ccaagaacaa agctcaacga  14880
gagggtcgtg aaccctgtga gctggacact cgggattacg tagagggtgc tccatacaca  14940
ccagtagagc acgttgtgtt caacccaagt agccgagacc acattgcgct caagctgaag  15000
gaagccggat gggtacccac agagttcacc gaaaagggtg cacctaaggt agacgacgag  15060
gtccttgagc atgttcgtgt gggggaccct gagaagcagc gctgtatcga cctcatcaaa  15120
gagtacctga tgatacagaa gcgtatcggt caggcggctg agggcgacaa agcgtggcta  15180
cgttacgttc aagaggatgg taaaatccat ggaagtgtta accctaatgg tgcagttaca  15240
gggcgagcaa cgcatagctt ccctaacctt ggtcaagttc cgggcgttcg ttcgccgtat  15300
ggtgagcctt gtcgagcagc gttcggcgca gagcatcact tggacggact taccggacag  15360
ccttgggttc aagcaggcat cgacgccagc ggactcgaac tccgttgtct ggcacacttc  15420
atgtctaagt acgacgacgg ggcatatgcg gatgtcattc tcaacggtga tatacacaca  15480
gtcaaccaaa cggcggctga gttgccaaca cgtgataacg ccaagacatt catctacggt  15540
ttcctctatg gtgctggaga cgaaaagatt ggacagattg tgggcgcagg taaggaacgc  15600
ggaaaggaac tcaagaagaa attccttgag aacaccccag caatcgcagc cctgcgtgaa  15660
ggaatccagc agaccctcgt cgagtcatcc cgatgggttg ccggagagca gaaggtcaag  15720
```

-continued

```
tggaaacgac gctggattaa gggactggat ggaagaaagg tacacgttcg gtcaccacat  15780
gccgcgctca acacgttgct tcagtcagcg ggtgcgctca tttgtaagct gtggattgtc  15840
gagactgaag agttgcttct taaggcagga ttgaagcacg gatgggatgg cgacttcgcc  15900
tacatggcgt gggttcacga tgaaatacaa gtggcctgcc ggacctcaga gattgcacag  15960
caggtgattg acatagcgca gcaagctatg cgtaacgtgg gagaccactt taagttccgt  16020
tgccgtctgg acacagaagg taagatgggt ccgaactggg ccgtatgtca ctaataatac  16080
aggagattta tcatgggtat taacaaacag tttcgcgtaa cgttcgatgt aacggctact  16140
atgagtgatg accaagagcg ggagttcctt gaggacctac tatctcttgc gtatggcgtg  16200
gacgacaaac gtcaggcgca cattgtaacc gaagcaatca ccaaaggtca tgaggcggca  16260
ctggcattcg tcatgcagag tggtctgcgg gaagctatta aggacatcgg taaggagctg  16320
agctgctccg ctgtgacagt acgcttctct ccggcaaccg tgagggtgac taagtgagcg  16380
agtacctcaa agttctggcg gccctcaagg gctgccctaa gtccttccag tcgaactacg  16440
tgcggaacaa cgccgcgtta gtcgctgagg ctgcgagccg tggtcacatt tcatgtctga  16500
ccatgagtgg tcgtaacggt ggcgcttggg aaattaccag tgccggagtg aaattcctta  16560
aggcccatgg aggttgtcta tgaaagactt tttaggtaac gatatcgaga ttggcgacac  16620
cattgtgtat gctgacgctg gtggccgtgg aggctcttcg ggtcttaaca agacagtagt  16680
tacccgaatg actgataaac aggtcatggt gtacgaatca acgtggtcaa aactgtggcg  16740
tccgtttgac cgtgttgtgg ttgttgctaa gggaggttcc caatgaagca cacattgtta  16800
tccttcagtg actaccgggc aacccagaag attgccaagg gtgtccttgt gatggatggt  16860
gactggttgg tattccaagc catgagtgcc gctgagttcg atgcctcgtg ggaggaggag  16920
atttggcacc gttgctgtga ccacgctaag gcccgagaga ttctggagaa ctccatcgag  16980
tcctacaagg gccgcaagaa ggcgtggaag aatgcagacg ttgtcctagc gttcactgac  17040
cgtgtcaact ggcgcaagct gcttgtggac ccgacgtaca aagagaaccg cgcagtcgtc  17100
aagaaacctg tgggttactt tgagttcctt gagtacgtct ttgagtccta cacatgtgtc  17160
cttgagcctc agctcgaagg tgatgacgtg atgggtatca tcgggtctaa ccctctcgtg  17220
tacaactacg agaaggccgt gctggtctcc tgcgacaagg actttaagac catcccggat  17280
tgtgatttcc tgtggtgcac gactggtaac atcctcgttc agactcagga gacagccgac  17340
tactggcacc tcttccagac tatcaagggt gacatcaccg atggttacgg tgggattccc  17400
ggatggggag ataccgctga ggacttcctc aaggaaccct tcattgtgga gcctgtaacg  17460
tccgtgctga agtccggtaa gaacaagggc caagaggtaa ccaagtgggt gaaacgcgct  17520
cctgagccgg gagagacgct ctgggactgc attaagtcca ttggtgccaa agcagggatg  17580
accgaagcgg aagtaattaa gcagggccag atggctcgca tcctccgttc tgatgagtac  17640
aacatcgaga ctggggagat tactctatgg caaccgggca gctgattctc atcgtcctga  17700
ccatgggctt agttgctcgt ggtctctgga tgttggcctt gattatcaag cagatagtcg  17760
agcataaagc agagtgataa actcatgggc acaattagga cccactatag ggaagtgccc  17820
attatgatta ttacttaaag attacttaga gaggagactc aaatgttaaa acctatagag  17880
cacatcctta acaatcctaa tgaccttcct gacgtaccgc gagctgtcaa ggagtaccta  17940
cagtctcgct tcaatgctga cttcctgtat cagtcagagg tccgtaagct gcgtgaggct  18000
ggccacagtg aggagttcat ctccggtgta ctgtatggtc actacatggc ttctcgtgtc  18060
cttgacgaga tggagggccg ccagcgtgca ctcaaagaag gagattgatt atgtgtttct  18120
```

```
cacctaagat gaaagcacct aaggtcgaca caacgactgt ccctgagcca gctccgctca  18180
ctgaggaacc taagggtatc cagtacggtg gcgacgaaga ctcaaacagc accactcctg  18240
aggtgtcagg gcgtaagtca ctcaaggtga ccaagacgac cgagcccaca gggtcagtca  18300
gtaaaatccg taagtcagct ttaggaggct aacatgggac tgttcaagaa aatcaagaag  18360
gctatctcca aggtagtcaa ggcaccactc aaggccgtgg gtctagcagc agatgcgcct  18420
aacgtgcaga cagccgctga gacacctgtg gcagcacctc aggaagcacc gaaagaggtc  18480
gtggaggacg ttgagtcttc agcagacacc gagtctggta agaagaaatc ccgagcgtct  18540
ggtaagaagt ccctctcagt ttcccgcagc tcaggcggtg ggattaactt atgattggtt  18600
acggggaggg ctaacaaatg gcagaagtta aactcgaagg cttcgcagag gagggagcca  18660
aggcggtgta tgaccgtctg aagaacgacc gacaacctta cgagacacga gcagagtcct  18720
gtgcgcagta cacgattcca tcactgttcc ctaaggactc cgataacgca tcaacagatt  18780
acacgactcc gtggcaatcc gtaggtgctc gcggcctgaa caacctagcg tccaagctga  18840
tgttggccct gttcccgatg cagtcatgga tgaagttgac cattagtgaa tacgaagcga  18900
agaaccttct gggtgacgct gagggtctcg ctaaggtcga tgagggccta tcaatggtag  18960
agcgaatcat catgaactac atcgagtcca acagttaccg agtgactctc ttcgagtgct  19020
tgaagcaact gtgtgtggcc gggaacgcat tgctgtactt accggagcct gagggttaca  19080
ccccgatgaa gctctatcgc ctgaactcgt atgtggtcca gcgagacgct ttcggtaacg  19140
tactccagat tgtcactctc gacaagattg cgttcaacgc tctccctgag gatgtccgca  19200
gccaagtgga agcagcccaa ggtgagcaga aggaagacgc tgaggttgac gtctacaccc  19260
acgtgtacct gaacgaatcc ggggatggct actcgaagta cgaagaggtt gccgaagcag  19320
tagtaccggg cagcgaggct gaatacccgc tcgaagagtg tccgtacatt ccggtccgca  19380
tggtccgcat cgacggtgaa tcctacggtc gttcctacgt ggaagagtat ctgggtgacc  19440
tcaagtccct agagaacctc caagagtcca tcgtgaagat ggcgatgatt accgcgaagg  19500
tcatcggtct ggtagacccg gcaggtatca ctcaggtccg ccgactcacg gcagcacagt  19560
ctggtgcgtt cgtaccgggc cgtaagcagg acattgagtt cctccagctg gagaagtccg  19620
gtgactttac cgtagcgaag aacgtaagcg acaccattga ggctcgccta tcgtatgcct  19680
ttatgctcaa cagtgcggta caacgtacag gcgagcgagt cacagccgaa gagattcggt  19740
acgtggcgtc agagctggaa gataccctag gcggtgtcta ctcgattcta tcgcaggaac  19800
tccagctgcc tctggtaaga gtgctcttga agcaactaca agccacgcag caaatcccgg  19860
agttacctaa agaggccgtc gagccaacta tcagcactgg ccttgaggct atcggacgtg  19920
gtcaggacct tgacaagctg gagcggtgca ttgccgcatg gtcagccctt aaggccctcg  19980
aaggtgatga cgacctcaac ttggctaacc tcaagttacg tatcgctaac gctattggac  20040
tcgacactgc tggtatgctt ctcactcagg agcagaagaa cgcccttatg gcacagcaag  20100
gtgctcagat tgccacacag caaggggccg cagcgctggg tcaagggatg gccgcacagg  20160
ctactgcaag tcctgaagcg atggccgcag cagctgattc agtaggtatg caaccgggca  20220
tgtaattagg gcacactata gggagaccga ttggtttccc tcttagtctt aactttaagg  20280
agattgaaat ggctggcgaa tctaacgcag acgtatacgc atccttcggt gttaacagtg  20340
ctgtactgac tggtagtaca cctgaggagc accaagaaaa catgttggct cttgatgttg  20400
ctgcccgtga tggcgatgat gcaatcgagc tgaacacaaa cagtgatgac ccgtatggtt  20460
```

-continued

```
ccgatgtgga cccgttcggt gaacctgaag agggccgtat gcaggtccgt atctccgctg  20520
acggttcaga cgaacaggac ggcgaagagg gtcagggtga cgaagaacag cagggcgacg  20580
aagagagtca gccggaggaa gtaaccgatg aaggtgaacc tgaagagttc aaacctattg  20640
gtgaaactcc ggctgacatc aacgaagcct ctcagcagct ggaagaacac gaagctggct  20700
ttaacgacat ggttgctact gcaatcgaac gcggtctctc acaggatgct gtgacccgta  20760
ttcagcagga gtaccagaac gaggacagtt tgtccgacga gtcttaccga gagctggccg  20820
aggcgggcta cagtaaggcg ttcgtcgatg cgtacattcg cggtcaggag gctctggtca  20880
accagtacgt tgagaaagtg atggacttcg tgggaggccg tgagcgattc cagcaggtct  20940
acagtcacat gcagaccaat aaccctgagg gtgccgaggc gctcatcaag gcttttgagt  21000
ctcgtgatgt agccaccatg aagacgattc tgaacctagc gggacagtct cgtgataaaa  21060
cctttggtaa gaaagctgag cgctctattg ccaagcgtgc aaccccagcg aaacctgctc  21120
cccgcaaggc tgtaggcttc gagtctcaag ctgagatgat taaggcgatg tccgacccgc  21180
gctaccgcac cgactctaag tatcgtcgtg aagtagagca aaaggtaatc gactcaacgt  21240
tctaatgaat tagggcacac tatagggaga ccatcagact gaacacggtg acgtccactg  21300
gctcccttcg agttacacaa tgagtatcac ctcgtttcaa gtagtaactg acgcgacctt  21360
agggcaagac cttatgatag gcgcggagaa tcaccccaag agcttggcaa cgataggccc  21420
gtttggtcag cgtaatgact aattctattc gtaaacaaca taaggagatt caacatggct  21480
aacatgcaag gtggacagca gctcggtact aaccaaggta aaggtcaatc cgcagcagac  21540
aagctggcgc tattcctgaa agtattcggc ggtgaagtcc tgaccgcatt cgctcgtacc  21600
tctgtgacca ccaaccgtca catgcagcgt caaatcagct ccggtaagtc cgcacagttc  21660
cctgtgattg gccgcaccaa ggctgcttac ctgcaaccgg gcgagtctct ggatgacaaa  21720
cgtaaagaca tcaagcacac cgagaagacc attaacattg atggcctgct gaccgctgac  21780
gtgctgattt acgacatcga agacgcgatg aaccactatg acgtgcgctc cgagtacacc  21840
tctcagattg gtgaatctct ggcgatggcg gcggatggtg cggttctggc tgagctggct  21900
ggtctggtta acctcgctga ttccgtcaac gagaacatcg cgggtctggg caaaccgtcc  21960
ctgctggaag ttggtgctaa ggctgacctg accgacccgg ttaaactggg ccaagcggtt  22020
atcgcacagc tgaccattgc tcgtgcggcc ctgaccaaga actacgtccc ggcgaacgac  22080
cgtacgttct acaccacccc ggacgtgtac tctgcgattc tggcggctct gatgcctaac  22140
gctgcgaact atgcggctct gattgaccct gagcgtggct ctatccgtaa cgtgatgggc  22200
ttcgaagtcg tagaggttcc gcacctgacc gctggtggtg ctggtgatga ccgcccggac  22260
gaaggcgcag aagcgaccaa ccagaagcac gccttcccgg caactggcgg taaagtcaac  22320
aaagagaacg ttgtgggcct gttccagcac cgttccgctg tcggcaccgt taaactgaaa  22380
gacctggctc tggagcgtgc tcgtcgtact gagtatcagg ctgaccagat tgttgccaag  22440
tacgcgatgg gtcatggtgg tctgcgtcca gaatctgctg gtgcgctggt tttcacagca  22500
gcctaagcgt aaatacettt agtgctcgga cggtaactcc gtctgagtat gaggtacaga  22560
ctgtggccat tactggtgat tcacttaagg tgacacttgg tgggctggag ggagtaacgg  22620
actggtcaac acttgaggta acttatggta cttccgggat tgccagccac actcgccgga  22680
ccaacacgct gtacttcaaa ggaatcgctg tgggcgaaac tctagtgact gtcagctttg  22740
acgggtctga aaggaagtcc tttaagctgg tcgtgactaa ttaaaactaa gccaaacccc  22800
ttggggacca ctcacggtct ctgaggggtt ttttcgttag gagcttacat tatgaacatg  22860
```

-continued

```
caagatgctt actttgggtc tgccgctgag ctggatgcta tcaacgagat gctcgcagct  22920
atcggtgaat ccccggtgac cacccttgac gaagatggta gcgcagacgt agctaacgct  22980
cgtcgtatcc tcaacaggat taaccgccag attcagtcta aaggttgggc cttcaacatc  23040
aacgagtcgg ccacgctgac ccctgacgcg gacactgggc ttatcccgtt ccgtccggcc  23100
tacctgtcca tccttggtgg ccagtacgtc aaccgtggtg gttgggtgta cgacaagtcc  23160
acagagacgg ataccttctc tggggcaatc acagtgaccc taatcacact tcaggactac  23220
gacgagatgc ctgagtgttt ccgccagtgg attgtcacca aggccagccg tcagttcaac  23280
tctcggttct tcggagcgga ggacgtagag aactctctgg cacaggaaga gatggaagcg  23340
cgtatggcat gcaacgagta cgagatggac ttcggtcagt acaacatgct tgacggcgac  23400
gcatacgtgc agggtctcat cggtcgttaa tcagaaactt aaggaggacc aaatggctct  23460
cgtatcacaa tcaatcaaga acctcaaggg aggcattagc cagcagcctg aaatcctacg  23520
gtacccagag cagggtacac ttcaggtcaa cggttggtcc tccgagactg agggtctcca  23580
gaagcgacca cctatggtgt tcatcaagtc ccttggacct aggggctact tgggggaaga  23640
cccgtacatt cacctcatca accgagatga atacgagcag tattacgcag tgttcactgg  23700
gaacgatgtt cgggtattcg acctgtccgg ctatgagtac caagtaagag gtgaccgctc  23760
gtatatctca gtagtcaacc ctaaggataa cttgcggatg ataaccgtgg ccgactacac  23820
gttcatcgtt aaccgtaccc gacaggtccg cgagaaccag aacgtgacca acggtggtac  23880
cttcagggac aacgtggacg gtattgtcaa cgtccgtggt ggccagtatg gtcgtaagct  23940
cgaagtgaac attaacggtg tatgggtcag ccaccagctg cctccgggtg acaacgctaa  24000
ggatgacccg cccaaggttg acgcacaggc cattgcggct gcactcgctg acctacttcg  24060
tgtggcccac ccaacgtgga cattcaacgt ggggactggt tatatccact gcatcgcacc  24120
agctggggta actcttgatg agttccagac gagggacggt tacgcggacc agctgattaa  24180
cccggtgacc cactacgttc agagcttctc taagttgcca cttaacgcgc ctgacgggta  24240
catggtgaag attgtcgggg acacgtccaa gactgctgac cagtattacg tgaagtatga  24300
cgcttctcag aaggtctgga aggaaaccgt gggctggaac atctcggtcg gccttgagta  24360
tcacacgatg ccttggactc tggtgcgtgc agctgacggt aactttgacc tcgggtatca  24420
cgagtggagg gaccgccgtg ctggtgacga cgacactaac cctcagccgt cctttgttaa  24480
ctcaacgata accgatgtgt tcttcttcag gaaccgctta gggttcatct ctggggagaa  24540
catcgtgctt tcccgcacca gtaaatactt tgagttctac ccgccgtcag tggccaacta  24600
tacggacgat gacccgctag atgttgccgt gagtcataac cgtgtgtcgg tccttaagta  24660
cgctgtgagc ttcgctgagg agcttctgct gtggtccgat gaggctcagt tcgtcctgtc  24720
ggccaacggt gtgttatccg ctaagactgc acagctggac ctgaccactc agttcgatgt  24780
gtcagaccgt gcgcgtcctt acggtatcgg caggaacatc tactatgcgt ctcctcgaag  24840
ctcctttacg tccatcatgc gctactacgc ggtacaggat gtaagctctg tgaagaacgc  24900
agaggacatg acggcccacg tcccgaacta catcccgaac ggtgtgtaca gtatcaacgg  24960
gtccggtact gagaacttcg cgtgtgtgct gaccaagggt gctcccagca aggtgttcat  25020
ctacaagttc ctctacatgg acgagaacat tcgacagcag tcatggtccc actgggactt  25080
cggagatggt gtggaggtga tggctgcaaa ctgcatcaac tcaacgatgt acctgctgat  25140
gcggaacgcc tacaacgtgt ggatagctgc tgtggacttt aagaaggagt cgactgactt  25200
```

-continued

```
cccgttcgag ccttacaggt tccacgtgga tgccaagcgg tcatatcaca tctcagagac  25260
tgcgtacgac atcgagacca accagacggt agtgaacgtc aaggacatct acggtgcgtc  25320
gttctccaat ggtacggtgg caatctgcga gagtgacggc aaaatcaccg agtatgagcc  25380
gatgggtgac tcttgggatt caaccccaga catccgcatt agcggtgaca tctctggcaa  25440
ggatatcgtc attgggttcc tgtacgactt ccaatatgtg ttcagtcggt tcctcatcaa  25500
gcaggagcag aacgatggca caacgtccac agaggacgcc ggacgcctac aacttcggag  25560
agcgtgggtg aactatcagg acactggtgc gttcactgtg agtgtcgaga atggcaaccg  25620
tgagttcaac tatctggtca acgccagagt aggctccacg ggtctacgtc ttggccagaa  25680
ggcaacgacc actggtcagt atcgcttccc ggtgacaggt aacgccttgt accagaaggt  25740
gtccctgagt tccttcaacg cttccccggt gtcaatcatt gggtgcggct gggaaggtaa  25800
ctacagcaga cgagccaacg gcatttaact gaaggaatcc ttatggtgtg ctcaattagg  25860
gcacactata gggagaccac actaagaggg gacttaaagc atgtacataa gacaatccac  25920
taaaactgac ctatttgtgt tcaagccgtc ccgtgacgat agacttgagg cagcagcctt  25980
gggtatagct ccgggattcc caccgcatac cgaatgtgtc tcactggtta ccgatggtga  26040
catagagggc acatacaacc ttctggctat tggaggcaac gtgggtgacc aagtgtggtt  26100
cgtaacggac cagaaggtat cacgcttgac cagagaggag cgtttagagt ttcgtaagaa  26160
cattatcgaa taccgcgaca ggttacacga gaagtaccca atcctctgga actacgtgtg  26220
ggtaggtaac aagtcgcaca ttcggttcct gaagacaatt ggtgctgtat tcgagaatga  26280
ttttacactc aacggcacct tccaactgtt caccataacg aggaggtaac tatgtgctgg  26340
atggcagcta ttcctatcgc aatgacggcg gtgcaggcca tcggccagtc acgcaatgaa  26400
gccaagatga ttggccttca gaatgaccag atgcgccgac agtctgccca gatgattaaa  26460
gagtcaaaca ttcagaacgc taacgccagc cttgagcaga agcagaagct ggaagaagcc  26520
agttcggacc tgaccgctaa gaatctcgat aaggttcagg ccatgggtac aatccgtgca  26580
gcaatcggag agggaaacct tgagggtgcc agcatggacc gtatcagtcg aatcgaggag  26640
ggcaagttca ttcgggaggc caacgcggtc accgataact accgtcgaga ctatgcgtca  26700
ctgttcgctc agcagctggg caactcagag tcaactattg accaagttaa gtccatgcag  26760
aaggctgagg gcaaaggtaa gtctaagctg gaacaggtgc tggacccgct ggcattgatg  26820
acctcacaag gcgcatccgc atattcgtca ggtgcgttcg acagtaaggg aaccaaggca  26880
ccaattagtc aggcccaagg tactaaggta ggaggtaagt aatggccagt aaattagaac  26940
aagcattaag ccaactgccg caggccgggt ctacccgcat ccgtggtggc tcagcgtcca  27000
tgcagtatcg cccagtaacc atccaacagg aagggttccg tcagtccaac ctcgtgcagt  27060
ccttggcgaa gtttggtact gcggtgggtg aggcagcgga tgcctacgac aagcgccaac  27120
gggacaaggc cgatgagcgg tccgacgaga ttatccgcaa gttgacccca gagcagcgcc  27180
gggaggcaat caagaacggg accctgctgt atcaggatga cccgtacgct atggaggccc  27240
tacggttcaa gactggtcgt aacgcagcgt tcctcattga cgacgaagtg gcacagcgtg  27300
ttcagaacgg tgagttccgt acccgtgctg agatggaaga gtaccgccac aaacggttga  27360
ccgaaggtgc caacgagttc gctgaacagt tcatgattaa ccctgaggac tctgagttcc  27420
agagagggtt caacgcgaac atcactgagc gcaacatctc gctgtacggt aagcacgata  27480
cgttcctgag cgagcaggcc cagaagggtg ccatactggc ctcgaaggtg gagctgtcag  27540
gtgtgctcaa agaccctgcc gttctggccc gtccagagtc cggtgagttc ttccagcgct  27600
```

```
acatcgacaa cgcacttaag actgggagta tccctagcga cgctcaggca cagcaggtca  27660
tcatcgggtc ccttaacgac gtcattcagc gtccgggtgc taccaacttc ctccagagcc  27720
ttgagggccg cccagtcacc cttaatggga agaccacgac ctataaggag ctgatgggag  27780
aggagcaatg gaacgccctg atggtcaagg cccagtcaac tcagttcgac aatgacgcta  27840
agttgtctga aggtttccgc cttgggatta ccagcgcgtt gaaccaagac gataccagca  27900
agggctggga gatgcttcag ggtgccaaag cggaacttga ccgcctgcaa cccggtgagc  27960
agatgacccc agagcgtgag cgcttgattc aggctgagga gcagatgcag gcccgtttcc  28020
gtcaggaggc ccaagccgca gccaaggaga tggacaagcg tcagaagacc atcaacaaga  28080
atcaggtcat cgaccagcag ttcaccaagc gtatcaacgg tcagtacgtg tccaccagct  28140
acaaggacat gccgaccaat gagaacaccg gagagttcac gcacagtgac atggtgaact  28200
acgctaacgg taagctggcc gagattgacc agatgcagct cacggagcaa cagaaggacc  28260
gcatgaagct gagctacctc cgggcagact cagagggtgg agccttccgt accgttgtgg  28320
gccagttggt aaccgacgcc gggtctgaat ggtctgccgc tgtgattaac ggtaagttac  28380
cggaggacac cacagcgttg aacaaactgc gcaccatgcg taacaccgac ccggacctct  28440
tcgctgcact gtacccggac aaggctgact tgttcctgac gatggacatg atggataagc  28500
agggcattga cccgcagatt ctcatcgacg ctgaccgttc tcgccgcagt ctcaccaagg  28560
agatgcagta cgaggacgat aaggcgtggg cgtccctgaa gaacaactca gagtccccag  28620
agctgtcccg cattccggct agtctggatg gtatggcccg taagatttac gacagcgtca  28680
agtaccgtac aggcaacagc gacatggcga tgcagcagac cgacaagttc ctcaaggaat  28740
ccactgtgac cttcaagggt gatgacgtgg atggcgatac cattggtatt atcccgaaga  28800
acatcctaca ggtcagtgat gaccctaaga gctgggagca gggccgagac atcctcgaag  28860
aagcccgtaa gggaatcatt gcggctaacc cttgggtgac caacaagcag ctgacgatgt  28920
accagcaggg tgactctatc tacatgatgg acaccactgg cactgtgcga atccgctacg  28980
acaaggagct actgactcgc acttatcagg aacagcagca gcgtctggcc aaggaagccg  29040
aagagaaggc actgaaggaa gcaaccaagc gtgcacctat cgccgcagcc actcaggccc  29100
gtaaggccgc tggtgagcgt gtccgtgcga aacgtaaagc cactccgaag ttcatctatg  29160
gaggtggtga ccaataatca ttaaggagac aacatgagct acgataagtc caaacctagc  29220
gattacgatg gcatctttca gaaggcagca gactctcatg ggtctcccta tgacctcctg  29280
cgtaagttat cgtttaacga atcatccttc aaccctaagg ccgtctctaa gactggccct  29340
aagggaatca tgcagttcac ccgcaacacg gcccgagcga tgggccttaa cgtgacagat  29400
ggtgacgacg atgggcgcta caaccctgag ttagccattg acgctggcgc taagctgctt  29460
gcgagcctcg ttaagaagta caatggggat gagcttaaag cggccctagc gtacaaccaa  29520
ggggaaggcc cagcaggtgc ccctcagctc caagcgtacg acaagggaga cttcgggtct  29580
atctcggagg aagggcgtaa ctacatgcgc aagctgctgg atgtggccaa gagtccgaac  29640
tcaggcgcac tggaggcgtt cggtggcatc accccaaagg gtaaagggat tcccgcagag  29700
gatgccttca agggcatcgc taaggctgga aaggttggta ccgaactgcc ggagtcccat  29760
gggttcgaca ttgagggtgt agcgcaggaa gcaccaaaca ctccatacgc taaggacttc  29820
tgggagaaga ccgggactac tctcgatgag tataactctc ggtcaacctt cttcgggttc  29880
ggggacgctg ctgaggctca gattcagaac tccacattag gtgtggcctt ccgtgctgcg  29940
```

-continued

```
cgggctgacg atgggtacga tgtgttcaag gacacgatga ccccgactcg ctggaactct  30000
tatgttccct ccaaggaaga cctacagaag ctgcgcgact ctgggctacc tccgagctac  30060
tacggtgtgg tgactggtgg tgacggtgag aactgggatg cactcatcaa gctggccaag  30120
gataacttcg aggctgacca acgggccgct gaggctggta ctggggcgaa actcgctgct  30180
ggtatcgttg gggctggtgt agacccactc agctatgtac ctctggtcgg tgtggccggg  30240
aagggactca aggttgtcaa taaggccctg ctagtaggcg cacaggctgg ggcactcagt  30300
gttgcctctg agggaatccg tacgtcagtg gctggtggcg aggctcacta cgctgatgcg  30360
gcactcggtg ggttactgtt tggcgctggt atgtcggctc tcagtgatgc tgtggcggct  30420
ggtatccgta aggcccgtgg agtcgattct gtgaatgagt tcgctggacc agcactccgt  30480
atggaagcgc gagagactgc catcaacact ggtggtcatg acacctcgac gctacctcca  30540
gagaacttct cgttcgagca ggaccacaga ggcgttccgt ttgctgacca cccgaccgaa  30600
gagggagcag tggttctggc caatggttcc atcctgagcg ataccaaccc gcttaaccca  30660
aggactcaac gtgacttcgc agagattgac ccagagcgtg cagctcccgg tatcaaactc  30720
ggtgggttca ctgagattgg cctgaagacc ttagggtcca aggatgctgg tgtacgtgca  30780
atcgctcagg acctcgtgcg ctctcccaca gggatgcaat cagggtctag tggtaagttc  30840
ggtgcgaccg cttcggacat ccacgagcga ctccatgcga ctgaccaacg gatgtataac  30900
caactgtatg acgctgttga ccgtgccatg aaggacccag agttctccgt gggcgagcag  30960
aagatgtcac gcagagccat ccgtcaggaa gtctacaagc gtgcctcatt ggcgattgag  31020
cgcccagagt tacaggctga tttgaccaaa ggtgaacgtg aggtgatgga cctgctgaaa  31080
gagcacttcg acaccaagcg tgaactgatg gaacagccgg gtatcttcgg taacgctaac  31140
gccgtgagca tcttccccgg tagtcgacac aagggtactt acgtgcctaa cgtgtacgac  31200
aggggtgcca aggaactgat gatgcagaag ctgggcggac ctgaaggact ccaacaggca  31260
atcgctcaga gctggcttac cagttaccga gtgcgacctg aggtcaaggc gcgtgttgac  31320
gagtacctga tggaactcaa cggctacaag tcggtagacc aagtgacacc tgaggtggtc  31380
cagaagcacg ctatggataa ggcgtacggt atcagccaca ctgaggactt cacagcgtcc  31440
agtgtcattg acgacaacat cacaggtctg gtcggtatcg agaacaactc gttccttgag  31500
gcccgtaaca tgttcgacag cgacctcccg gttaccttac cggatgggtc aaccttcagc  31560
gtcaacgacc tgagggactt cgacatggca cggattatcc cagcgtacga ccgtcgagtt  31620
aacggtgata tctccatcat gggcggtagc ggtaagacca cgcagcagct caaggacgaa  31680
atcatggcgt tagacaagcg ggctgagcgt aagggacagc tgaagggcga agtggaagca  31740
ctgaaggaca ccgttaagat tctcacgggg cgtgctcgtc gtaacaacga tacagccttt  31800
gagaccgcca tgcgtaccct gaacgaccta gcgttcttcg ctaagaactt ctacatgggt  31860
ccgcagaacc tcacagagat tgctgggatg ttggctaagg gtaacgttaa ggcgatgctc  31920
cacggtatcc cgacgttgcg tgacctagcc accagaacct ctccggtgtc cggtagtgaa  31980
ctccgcgaac tccatggggc gctgttcggt aaggaactcg accagttaat ccgtccgggg  32040
cgtgaggata tcgtacagcg aatccgcgag gcttccgata ccagtggggc catggcgtca  32100
gtcattggca ccatcaagtt cggtactcag gagctgtcgg ctcgttctcc ttggaccaag  32160
atgctgaacg gtacggctaa ctacattctg gacactgccc gtcagggtgt gctcggtgat  32220
gtggctggtg cggccctagg cggtaagggt tccaagtttg gcaaagagaa cttcctcaaa  32280
gctgcctcta tcagtcctga gcagtggaag ggaatcaagc aactctttgt cgaccacgca  32340
```

-continued actcgtgacg ctaacggcca gttcaccatc aaggacaaga aggctttcag tcaggacccg 32400
agagcgatgg acctgtggcg tcttgccgat aaggttgccg acgagaccat gctgcgccct 32460
cacaaggtat cccagcagga ttccaaggcg tacggtgctg gtgtcaagat ggctatgcag 32520
ttcaagaact tcaccatcaa gtcactcaat gccaagttca ttcggtcctt ctacgagggc 32580
tacaagaaca accgcgctat cgacatggcg ttgacacacg tgttgtctct gggtatcgcc 32640
gggacttact ttgcgatgca ggcccacgtg aaggcttacg gcctccaaga gtcccaacgt 32700
aaggactacc tgaagaaagc cctgaacccg accatgctgg gctacgcagc gttgactcga 32760
agttcccaca ctggtgcccc gctgtccatc gtttcgatga tggctggtgc cgctgggttc 32820
caagacgcca acatgctgcg ctccaccatc ttacctaagg aggaacaatt ccagaagaaa 32880
gatggagcgt ccaaaggtcg agccgagtcg agcaaccttg cgggtaactt agggtctcag 32940
gtcccagctc tgggttacgt agggaacgtc attgctaccg ccaagaacgc ctacggtgtt 33000
gctacagcac ccaacaagcc gactgagcgt gactacatga ctggcctgat gaactccacc 33060
aaggagcttg ttccgaacga cccactgacc cagcagctca tcatgaaaat ctatgaagcc 33120
aacggggtca ccatcaagca gcagccgaag cctaactaat taggacacac tatagggaga 33180
ccgattggtt tccccccttc tcattcaact aaaggaggtc acaatggacc aagacattaa 33240
aacagtcatt cagtacccag taggggccac tgagttcgac atcccgttcg actacctgtc 33300
ccgtaagttt gtccgtgtgt cgctggcagc tgacgacaac cgcagactgc tgagtaacat 33360
cactgagtac cgctacgtgt ctaagaccag agtgaagctc cttgtggaaa ctaccgggtt 33420
cgaccgtgtg gaaatccgca gattcacctc agcgtctgag cgtattgttg acttcagcga 33480
cggctccgta ctgcgggcaa cagaccttaa cgtttctcag attcagtctg cccatatcgc 33540
agaggaagca cgtgattcag cactgttggc tatgccgcag gatgatgctg gcaaccttga 33600
tgcccgtaac cgcagaatcg ttcggctggc tccgggtgtc gaaggtacgg atgcaatcaa 33660
caagaaccag ctggacacca ccttaggtga agctggtggc atcctgtcgg aaatcaaaca 33720
gaccgagaag gacattcagg attacatcga gaactttgca gatgacacca cgtctctcaa 33780
gggaatcaac tgggtgtata acaatgggtc ggccaatggt ggcgagacct ccatcctgat 33840
tacccgcgag gggccagtgt tcgctgtgcc taccatttac atcaatgggg acagacagtc 33900
tgttggttac cactactctt acgactccgg tgataagacc attcacctag ttaagccgct 33960
aactgctgga gactttgtgg aatgtgttac ctctgagggc gtactgccgc tgtctaatct 34020
tctgtcgaca ccagacgggg ccagtcagat tggcactaaa agcggcctga ctgtgcaaga 34080
ctaccttaac ggcgtgaagt ccgctaccat cctgcgcaac attgagccag tcattgatgg 34140
acagcgcatc gtcctctctg agattagccc tactttgggg cctaagtctg gaggtacctt 34200
ggtgtacgac cagtctgata catcctctgt ggacgacggg tacactgttt tcgtgacagc 34260
tggcggtaaa cggtggaagc gagaagagtc ctacattgac gtagcgtggt tcggtcctaa 34320
ctttggcctt gccttacaga ccgctgttaa cctcgttgac aactacgtga gaactgtcgg 34380
tttctacagt cgcaagacca tctacattgc agctggtacc tatacgacag accgtcaggt 34440
ggacattcca tcttatgtct ctgtggtggc cataggtaac gttagcatca atggttctgg 34500
gcttccagta aactcctacg tactccgcat aacgaacaag gttggtggca ttgtcacaac 34560
ccaccactca gggtggaacc tcggggccgt aggtgggacc cttcgtcttg taggaaacgg 34620
caacaccggg caagtggatg ggctttatgt gggcggtgcg acttctatga gcgacgtacg 34680

-continued

```
gaacgttagc ctttacgctg tgtcaacttc gggtgttcgc tatgggctaa catttggtag  34740
caccaacact tacctcttca cggcaaccaa atgccacttt gagacgtctc ttgtaaacct  34800
gtacattccg ggcaccacaa gctctaactc aggggagaag atggtattca atgatactgt  34860
gttcggtggc tcatctagga accatgtaga ggtaagcacc ccaggcatgg acctcacgtt  34920
caataactgc tctttcgact tcacaagcgg tagcgtcctg tacgggacag agacttgggg  34980
ctatgcgaaa gtaggcatga ataattgcca cttcgagggg ttcaatagtt tgtggataaa  35040
ggtggatgcc ccgcaaggtg gattcattgg gtcaaaccga gcgataaccg tatcaaacgc  35100
cacagtcctt cctaggcttc gctccaacac tgctggaaca aactcggcga gccgtatgca  35160
cattgatgcc aagtctaccc cggtgtatat cagtgggctg gacctacggc acgaggtcgt  35220
accatacacc gaggaaatct tcatggcttc agctgaaact accctgtctc tgcaaggata  35280
tcttaaggac ccgcatttcc agattccaag tgctgcgcac attcagaacc gtgggtggaa  35340
catcgctgac gaaacaactg gaactgttgt gaacagcccc gcaaccttgg attcccttac  35400
gcgatttaca tgcaccgaga ggaacgcgat gtctgcggct gtggtcgatg gtggaacttc  35460
tggtaagctc ttagcaatga ctggagcggg tgggtatttc actctggtca ctaaaggatt  35520
cattccggtg agtacgttcc aacggattgg cggagcaatg tcgattcagg cagcagcaag  35580
taccggaaac atccagtgca cgcttggtgt ccagtggttc gactacgatg gtaacctaat  35640
cgggacagac caagcctttg cgattaacat gcgtgaggtg ttcaacaact cttctctacc  35700
taacttcgcc gaaggcaaca accgcttcat ctctacatct gcgagaacat tccgtgcgcc  35760
agcgggggcc gctaagtgta aaccattgtg gcgaatctct ggtcatactg gcgttgtgaa  35820
catctcgaga ttagcatcat ttgttttata aggagacaac atgctgaatg atttaaacca  35880
accacgaggc tcgacgctgg gcctctttac tccaaacctt ccgttgaaga agcggttgga  35940
caccttacca aacattttag attttgattc agacagcctt aacgatgata gcactcggtt  36000
tcaaaaggct attacagctg gtgtgaaatc tttatacgtc ccagaacctc agttctttgg  36060
caacaataag cctcttaaaa ttgctaacgt tgacattgtg accaatatgc acatctacgg  36120
gaacggctca gcgggatacc gtcaggttgg cggggccatc accatcctag atggagcgga  36180
ctatgggttt aaactggctg gtgtcgactc tcagacgcga aacattggag gccgcattga  36240
cggtctctcg ttccaaggtg agttcccaac gaccgtggcc gacgccatcc ggtgccaatc  36300
tgccagtagc ttcgcgctgg tcaacctctc gttcaggaac ctctccgggt ccgctctgga  36360
cctgcgtgac ttcatggaga gccacattga gcactgctac tttaactcag taggttccga  36420
cacaaagaac ccaatcaaca tcggggactt cgtcgggtcg gctccttgga acgtcaacaa  36480
cctgcacatt gagaacaaca ccttcgggtc atgtagtggg aacattatca acattagtga  36540
ctcagctaac gccgacctca tttggattct caacaataaa ttcgaatggg actcgacccc  36600
agtaagcccc aacgtttcca acaaggcggt ggcatacatc gggcgagccg agcgtgtaaa  36660
tgtgtccggt aacggcttcg tgtactacta cccggcccac aacaagtacg atgcccttat  36720
ccgagtttcc gataagtcgg cctatggtaa cttgttctct gataataccg cttggggctg  36780
tacgcctcct tcaggtagtg acctcactcc agcgttctat tgggacattg ctggtgggtc  36840
gtctgcgggg tctaacaaca aggctaacac aaacctccct acgcgctgca ccagtatcca  36900
ctctcaggat atcgacgagc cgctggtaag gactactccg ggtaaccgac caaacctcca  36960
gagcatcggg gcaatgtctc ccggatatct ctctgcgcac tccttaggtg gggctaacgc  37020
ttccaacttc tttgtgccag acactggtgc taccaagtac ggtacggtgc tagaggctca  37080
```

```
aactggtggt gaggttcgcc gcttgttcat tcctaaggac attgttagcc agcgtgcttg  37140
cgttcgagtt caggccagag tgatgccgtc gccgacagct gatgcccttg tggggctgac  37200
ctgtgacggc tccattgttt ccaccacaat ccaaggcgca acccaagact accatacggt  37260
ggcggctggt ggcggctggc agattgtcga gtggctcatc ccggcgtcta gttacactgc  37320
gggccagtta atcttcacga accgtagtga caccgtcaag ttcaaacttg atggcgtccg  37380
tgtgtcacgt gcagacttcg tagatgtgac gattgcatgg agtccgaccc caatctccgc  37440
agggtctgtg gtaaacacca ctgcatcaat cactcgcgta agttcccacg tggtcggcac  37500
tagtggtctg aagacagacg gtacgttagg tggcgctgtt agtagctctt atttcaaccg  37560
tggggccaat accttagtgg tacagctggc agcactcaca gcagccactc cgtcaatcac  37620
tcaggttacg gttaggctgt tccttaacta aggaggtaac atgttgtccc tagacttcaa  37680
caacgaagtt atcaaggcgg ctcccattgc gggggtcgct ggggccgatg gtgtagcgag  37740
gctcttctgg ggcctctcac tcaacgagtg gttctacgtc gcggcaatcg cctacacagt  37800
ggttcagatt ggtgccaagg tagtcgacaa aatcattgac tggaagaaag caaataagga  37860
gtaacatatg gacctgatta agttcctcga aatgttagat actgagatgg ctcagcagat  37920
gctcatggac ctgaagaatc ccgagaagcg aacccctcag ctgtacaacg ccattggtaa  37980
actactggag cgccataagt tccaaatctc taagctgacc cctgacgtta acatcttggg  38040
cggactggct gagggtctgg aggcttacaa ctccaaggtg ggcgccgatg gtctgacaga  38100
cgacgatacg ttcaccctac agtgatatac tcaaggtact actatatgta gtgcctttat  38160
ggatgtcatt gcactacgct aggcgttcct acgtgaaatc tgagaaacaa cgggaggcat  38220
tatgctggag ttcacaaaga gaatcgtccc gtatcttgtg gctatcatgg tgtttgcctt  38280
cgggtggcac ttggggtctc aatctacgga cgctaaatgg aaggaggtag tacagcatga  38340
atacgttaag aagcaaacgg ctagagctga aactcagaaa gcgattgacg caatatcggc  38400
taagtaccaa gcagaccttg aggggctgga gggcagcact gatagggtta ttgctgattt  38460
gcgtagcgac aataagcggc tgcgcgtcag agtcaaacct accagtgtcg ccgcaggacc  38520
agacggtcga tgcctcgttg atggttccgt cgaactacac gaagcaactg ctcgaagtct  38580
tatcgcaata acccagaagg ccgacctcaa agagaaggcc ctacaggaca ctattcgcaa  38640
gctacagcgg aaaggaggtg aacattgagt aactctcagc aagccaagaa cgccttaatc  38700
attgcgcaac tgaagggtga ctttgtcgcc tttctcttcg tgctctggaa ggccctgaac  38760
ctgccggaac caaccaagtg tcaaatcgac atggccaagt gtctggcgaa cccaaagaac  38820
aagaagttta tccttcaggc tttccgtggt atcgggaagt cattcatcac gtgtgcgttc  38880
gtagtgtgga ccctgtggcg tgaccctcag ttaaagatac tgattgtctc ggcctcaaag  38940
gaacgtgcgg acgctaactc catcttcatc aagaacatca tcgacttgtt gcctttcctg  39000
agtgagctta agccccgccc cggtcagcgt gactccgtga ttagctttga tgtaggccct  39060
gccaagccag accacagccc gtcagttaag tctgtgggta ttactggtca gcttactggt  39120
agccgtgctg atatcatcat tgcggatgac gtggagattc ccggtaactc tgcaacccaa  39180
ggcgctcgtg agaaactctg gacgctggtt caggagttcg ccgcactgtt gaaacctctg  39240
ccgactagcc gtgttatcta tctgggtaca cctcagaccg agatgacgct ctacaaggaa  39300
cttgaggaca accgtgggta ctccaccatt atctggcctg cacagtatcc tcgctccaaa  39360
gaggaggacc tgtactatgg cgaccgactg gccccgatgc tccgtagtga gtacgatgag  39420
```

-continued

```
gacaaagagg gcctcagcag tcagcctact gacccggttc gattcgactc catggacctt  39480

caggaacgtg aggtggaata cggcaaggct ggctatacgc ttcagttcat gctcaacccg  39540

aacctcagtg acgccgagaa gtacccgcta cgcctccgtg acgctatcgt gtgcggtcta  39600

cagatggaca aggccccaat gcattaccag tggttgccga accgtcagaa ccgcaatgag  39660

gagcttccta acgtgggcat gaagggtgac gagatttact ccttccatac agcctcaagt  39720

aacactggcg cgtatcaggg taagattctg gtcattgacc ccagcggtcg cggtaaggat  39780

gagactggct ggtgcgtact gtacaccctc aacggttaca tctacttgat ggacgctggc  39840

ggtactcgtg ggtacgaaga gaagtccctt gagttcctcg ctaagaaagc caaacagtgg  39900

caggttcaga ctgtggtctt cgagagcaac ttcggtgacg gtatgttcgg taacgtgttc  39960

cagcctgtgc tcctgaagca tcacccagcg caactcgaag agattcgtgc tcgtggtatg  40020

aaagaggtcc gtatctgcga tacccttgag cctgtactgg caagtcaccg cttggtcatc  40080

cgtgatgagg ttatccgaca ggactaccag acggcacgtg atgcagacgg taagcacgct  40140

ctgaagtaca gtctgttcta ccagatgacc cgtatgagcc gtgagaaggg cgcggtggca  40200

cacgatgacc gacttgatgc gttagcattg ggtgtcgagt tcctacgctc tacgatgcag  40260

caggacgctg tgaagataga ggctgaggta cttcaggagt tcttggagca ccacatggag  40320

aagcccctga gtaacatctc ccagttccgg gccaccagta gcaacggtgt ggacatccga  40380

tgggaagacg atggggatga cactatgttc atcgcatggt gattatgcag ggattgtgca  40440

taaggattca ttaggccacg gaaggccact ttgaggaaac tccatgtata acagacactt  40500

ggaattagga cccactatag ggagagaccc ttgaagactt actataagac aacttaaaga  40560

ttcattcata tagttattca ctttaagtct ccttaaaggc agagggtagt gatgataata  40620

tcaccctctc actataagac actaagagcc aacataagga ggacctatgc gcttattgtt  40680

aaccttactg cgccataggg ctacttggcg atttctgctg gtacttgctg gtgcccttgg  40740

ggcttcactg gttactcagc agcaactcag tggactggag actctcgtgt gctctctact  40800

cacttgtagc gattagggtc ttcctgacgc gctagggatt ccgtagtgat gcttatcagc  40860

atacaccact ccatccctct acagtcaata cttaaagtta accttaggtg attcactggg  40920

tctacctacg ggtctatgca atgacctgag gagtacctga ggttaccttt aagaatttta  40980

cataaagttc tgagtgtaca tctcacagtt tacacttttg gttatccccc cggtaccctc  41040

cagttcaccc aaagtaacct agggtacccc tctttacctt tggtttaacc ttgggtggta  41100

ccttgggaat cccttaggtg ataccatatg ttggggtaat ggtgacctga ggacactata  41160

tgttgatgtc tctgtgtccc t                                            41181
```

<210> SEQ ID NO 2
<211> LENGTH: 103
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 2

```
gccaccugag guuagaccag guuuuagagc uagaaauagc aaguuaaaau aaggcuaguc    60

cguuaucaac uugaaaaagu ggcaccgagu cggugcuuuu uuu                     103
```

<210> SEQ ID NO 3
<211> LENGTH: 103
<212> TYPE: RNA

-continued

```
<213> ORGANISM: Artificial Sequence
<220> FEATURE:
<223> OTHER INFORMATION: Description of Artificial Sequence: Synthetic
      polynucleotide

<400> SEQUENCE: 3

ggcuacuugg cgauuucugc guuuuagagc uagaaauagc aaguuaaaau aaggcuaguc     60

cguuaucaac uugaaaaagu ggcaccgagu cggugcuuuu uuu                      103


<210> SEQ ID NO 4
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

taatacgact cactatagga aggtcattac tatatgtagg ttttagagct agaaatagca     60

agttaaaata aggctagtcc gttatcaact tgaaaaagtg gcaccgagtc ggtgcttttt    119


<210> SEQ ID NO 5
<211> LENGTH: 729
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

gcgtgaggca atcctgagca aagaggttgg cgaaacgtcc gtgcgtctgg ccgaagcgtc     60

agaagttaag tgataaactc aaggtcatta ctatatgtag aaggagattc aacatggtct    120

tcacactcga agatttcgtt ggggactggc gacagacagc cggctacaac ctggaccaag    180

tccttgaaca gggaggtgtg tccagtttgt ttcagaatct cggggtgtcc gtaactccga    240

tccaaaggat tgtcctgagc ggtgaaaatg ggctgaagat cgacatccat gtcatcatcc    300

cgtatgaagg tctgagcggc gaccaaatgg gccagatcga aaaaattttt aaggtggtgt    360

accctgtgga tgatcatcac tttaaggtga tcctgcacta tggcacactg gtaatcgacg    420

gggttacgcc gaacatgatc gactatttcg gacggccgta tgaaggcatc gccgtgttcg    480

acggcaaaaa gatcactgta acagggaccc tgtggaacgg caacaaaatt atcgacgagc    540

gcctgatcaa ccccgacggc tccctgctgt tccgagtaac catcaacgga gtgaccggct    600

ggcggctgtg cgaacgcatt ctggcgtaat ggcctttatg attatacaca caacatattg    660

agaggacatt accatgcgta aacctgaaga gattcgtaaa gagattgaag cgctgaacaa    720

agagctggc                                                            729
```

PHAGE ENGINEERING: PROTECTION BY CIRCULARIZED INTERMEDIATE

CROSS-REFERENCE TO RELATED APPLICATIONS

This application claims the benefit of and priority to U.S. Provisional Appl. No. 62/513,707, filed Jun. 1, 2017, the disclosures of which are incorporated by reference herein in their entireties.

SEQUENCE LISTING

The instant application contains a Sequence Listing which has been submitted electronically in ASCII format and is hereby incorporated by reference in its entirety. Said ASCII copy, created on Aug. 21, 2018, is named 102590-0634_SL.txt and is 56,076 bytes in size.

TECHNICAL FIELD

The present technology relates generally to methods and kits for generating recombinant bacteriophage genomes. In particular, the present technology relates to methods of integrating a heterologous nucleic acid sequence into a linear bacteriophage DNA genome, and isolating recombinant bacteriophages that express the heterologous nucleic acid sequence.

BACKGROUND

The following description of the background of the present technology is provided simply as an aid in understanding the present technology and is not admitted to describe or constitute prior art to the present technology.

Model phages have been engineered using molecular biology techniques to deliver heterologous protein products to bacterial cells. E.g., US 2009/0155215; M. J. Loessner et. al., *Applied and Environmental Microbiology*, Vol. 62, No. 4, pp. 1133-40 (1996)). The natural host range of model phage engineered to date is limited. Methods for creating variations in phage genomes and engineering new phage genomes may lead to the identification of phages with varied properties (e.g., varied host ranges) that are useful for diagnostic and therapeutic purposes.

Engineering diverse phage is generally made more difficult by the properties of phage genomes. For example, phage genomes have relatively few restriction sites and are heavily modified, making use of traditional cloning techniques with phage challenging. Phages also have compact genomes with very little non-coding DNA, which can make it challenging to find sites within the genome that are compatible with traditional engineering. Many existing phage engineering technologies that rely on in vitro strategies are generally inefficient and challenging to scale up. Further, engineering phages within bacteria can be problematic due to toxicity of phages to bacteria as well as the difficulty in maintaining the stability of large engineered genomes.

SUMMARY OF THE PRESENT TECHNOLOGY

In one aspect, the present disclosure provides a method for integrating a heterologous nucleic acid into a linear bacteriophage DNA genome comprising: (a) cleaving a first site at the 5' end of a plurality of linear bacteriophage DNA genomes and a second site at the 3' end of the plurality of linear bacteriophage DNA genomes with a CRISPR enzyme in vitro, wherein the plurality of linear bacteriophage DNA genomes is present in an isolated sample; (b) recombining in vitro the cleaved plurality of linear bacteriophage DNA genomes with the heterologous nucleic acid in the presence of a recombination system, wherein the heterologous nucleic acid comprises a 3' flanking region and a 5' flanking region that are homologous to the 5' and 3' ends of the cleaved plurality of linear bacteriophage DNA genomes respectively, thereby generating a plurality of circularized bacteriophage DNA genomes; and (c) enriching the plurality of circularized bacteriophage DNA genomes by incubating the sample with at least one exonuclease. The at least one exonuclease may be bidirectional or unidirectional. Additionally or alternatively, in some embodiments, the at least one exonuclease is selected from the group consisting of Lambda exonuclease, Exonuclease III, RecBCD, Exonuclease VIII truncated, T5 exonuclease, and T7 exonuclease. In some embodiments, the at least one exonuclease is RecBCD. In certain embodiments, the method further comprises propagating the plurality of circularized bacteriophage DNA genomes in a non-natural bacterial host. The plurality of linear bacteriophage DNA genomes may be recombinant or non-recombinant. In some embodiments, the linear bacteriophage DNA genome is a terminally redundant linear bacteriophage DNA genome.

In certain embodiments, the plurality of linear bacteriophage DNA genomes correspond to a bacteriophage family or order selected from the group consisting of Myoviridae, Styloviridae, Siphoviridae, Pedoviridae, Tectiviridae, Leviviridae, Podoviridae, and Plasmaviridae. In some embodiments, the plurality of linear bacteriophage DNA genomes are derived from one or more bacteriophage genuses (or genera) selected from the group consisting of T7-like phage, phiKMV-like phage, LUZ24-like phage, phiKZ-like phage, PB1-like phage, Felix-O1-like phage, T4-like phage, phi92-like phage, rV5-like phage, SP6-like phage, N4-like phage, phiEco32-like phage, T5-like phage, KP34-like phage, KP15-like phage, GAP227-like phage, AP22-like phage, phiFel-like phage, Sap6-like phage, Silvia-like phage, Kay-like phage, Twort-like phage, P68-like phage, and phiETA-like phage.

Additionally or alternatively, in some embodiments, the plurality of linear bacteriophage DNA genomes correspond to *Klebsiella* phage K11, lambda phage, Enterobacteria phage T2, Enterobacteria phage T1, Enterobacteria phage T7, Enterobacteria phage T5, Enterobacteria phage P1, Enterobacteria phage PRD1, K1E phage, K1-5 phage, RB49 phage, RB16 phage, KP15 phage, KP27 phage, Miro phage, Matisse phage, phiEap-3 phage, ECP3 phage, EFDG1 phage, EFLK1 phage, vB_Efae230P-4 phage, vB_EfaP_IME195 phage, SA11 phage, Stau2 phage, K phage, G1 phage, SA12 phage, 812 phage, P68 phage, SAP-2 phage, 44AHJD phage, or SA97 phage.

Additionally or alternatively, in some embodiments of the method, the CRISPR enzyme is a Cas protein selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. The CRISPR enzyme may be coupled to a sgRNA.

Additionally or alternatively, in some embodiments of the method, the recombination system comprises a 5'-3' exonuclease, a DNA polymerase, and a DNA ligase. In one embodiment, the 5'-3' exonuclease is T5 exonuclease, the DNA polymerase is Phusion® DNA polymerase (Thermo Fisher Scientific, Waltham, Mass.), and the DNA ligase is Taq ligase. In other embodiments, the recombination system comprises a 3'-5' exonuclease, a DNA polymerase, and a DNA ligase.

In any of the above embodiments, the heterologous nucleic acid comprises an open reading frame that encodes a bioluminescent protein, a fluorescent protein, a chemiluminescent protein, or any combination thereof. In certain embodiments, the open reading frame of the heterologous nucleic acid is operably linked to an expression control sequence that is capable of directing expression of the bioluminescent protein, the fluorescent protein, the chemiluminescent protein, or any combination thereof. In some embodiments, the expression control sequence is an inducible promoter or a constitutive promoter. The heterologous nucleic acid can be about 100-500 base pairs in length, about 500-1000 base pairs in length, 1000-1500 base pairs in length, about 1500-2000 base pairs in length, 2000-2500 base pairs in length, about 2500-3000 base pairs in length, 3000-3500 base pairs in length, or about 3500-4000 base pairs in length.

Examples of bioluminescent protein include, but are not limited to, Aequorin, firefly luciferase, *Renilla* luciferase, red luciferase, luxAB, and nanoluciferase. Examples of chemiluminescent protein include β-galactosidase, horseradish peroxidase (HRP), and alkaline phosphatase. Examples of fluorescent protein include, but are not limited to, TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOK, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherry1, PATagRFP, Kaede (green), Kaede (red), KikGR1 (green), KikGR1 (red), PS-CFP2, PS-CFP2, mEos2 (green), mEos2 (red), PSmOrange, or Dronpa.

In some embodiments of the method, the plurality of linear bacteriophage DNA genomes correspond to *Klebsiella* phage K11, wherein the first site at the 5' end of the plurality of linear bacteriophage DNA genomes is after the nucleotide located at position 232 of SEQ ID NO:1 and the second site at the 3' end of the plurality of linear bacteriophage DNA genomes is after the nucleotide located at position 40,715 of SEQ ID NO: 1. In certain embodiments, the CRISPR enzyme is Cas9 and is coupled to a single-guide RNA (sgRNA) having the sequence 5' GCCACCUGAGGUUAGACCAGGUUUUAGAGCUAGAAAUAGCAAGUUAAAAUAA GGCUAGUCCGUUAUCAACUUGAAAAAGUGGCACCGAGUCGGUGCUUUUUUU 3' (SEQ ID NO:2) or 5' GGCUACUUGGCGAUUUCUGCGUUUUAGAGCUAGAAAUAGCAAGUUAAAAUAA GGCUAGUCCGUUAUCAACUUGAAAAAGUGGCACCGAGUCGGUGCUUUUUUU 3' (SEQ ID NO:3).

In another aspect, the present disclosure provides a method for making an enriched plurality of recombinant circularized bacteriophage DNA genomes from a plurality of linear bacteriophage DNA genomes comprising: (a) contacting a sample comprising the plurality of linear bacteriophage DNA genomes with a first sgRNA-CRISPR enzyme complex and a second sgRNA-CRISPR enzyme complex in vitro under conditions where (i) the first sgRNA-CRISPR enzyme complex cleaves a first site at the 5' end of the plurality of linear bacteriophage DNA genomes; and (ii) the second sgRNA-CRISPR enzyme complex cleaves a second site at the 3' end of the plurality of linear bacteriophage DNA genomes; (b) recombining in vitro the cleaved plurality of linear bacteriophage DNA genomes with a heterologous nucleic acid in the presence of a recombination system under conditions to produce recombinant circularized bacteriophage DNA genomes; and (c) contacting the sample with at least one exonuclease to obtain an enriched plurality of recombinant circularized bacteriophage DNA genomes. The at least one exonuclease may be bidirectional or unidirectional. Additionally or alternatively, in some embodiments, the at least one exonuclease is selected from the group consisting of Lambda exonuclease, Exonuclease III, RecBCD, Exonuclease VIII truncated, T5 exonuclease, and T7 exonuclease. In some embodiments, the at least one exonuclease is RecBCD. The plurality of linear bacteriophage DNA genomes may be recombinant or non-recombinant.

The heterologous nucleic acid comprises a 3' flanking region and a 5' flanking region that are homologous to the 5' and 3' ends of the cleaved plurality of linear bacteriophage DNA genomes respectively. In certain embodiments, the method further comprises propagating the plurality of bacteriophage circularized genomes in a non-natural bacterial host.

In some embodiments, the plurality of linear bacteriophage DNA genomes correspond to *Klebsiella* phage K11. In certain embodiments, the first sgRNA-CRISPR enzyme complex comprises the sequence 5' GCCACCUGAGGUUAGACCAGGUUUUAGAGCUAGAAAUAGCAAGUUAAAAUAA GGCUAGUCCGUUAUCAACUUGAAAAAGUGGCACCGAGUCGGUGCUUUUUUU 3' (SEQ ID NO:2), and the second gRNA-CRISPR enzyme complex comprises the sequence 5' GGCUACUUGGCGAUUUCUGCGUUUUAGAGCUAGAAAUAGCAAGUUAAAAUAA GGCUAGUCCGUUAUCAACUUGAAAAAGUGGCACCGAGUCGGUGCUUUUUUU 3' (SEQ ID NO:3).

In another aspect, the present disclosure provides a method for integrating a heterologous nucleic acid into a non-terminally redundant linear bacteriophage DNA genome. In some embodiments, the method comprises: (a) contacting a sample comprising a linear bacteriophage DNA genome with a sgRNA-CRISPR enzyme complex in vitro under conditions where the sgRNA-CRISPR enzyme complex cleaves a first site at the 3' end of the linear bacteriophage DNA genome to produce a cleaved bacteriophage genome, wherein the cleaved bacteriophage genome comprises genomic sequence that is upstream of the first site; (b) recombining in vitro the cleaved bacteriophage genome with a heterologous nucleic acid in the presence of a recombination system under conditions to produce a circularized recombinant bacteriophage genome; and (c) contacting the sample with at least one exonuclease to enrich for the circularized recombinant bacteriophage genome. In other embodiments, the method comprises: (a) contacting a sample comprising a linear bacteriophage DNA genome with a sgRNA-CRISPR enzyme complex in vitro under conditions where the sgRNA-CRISPR enzyme complex cleaves a first site at the 5' end of the linear bacteriophage DNA genome to produce a cleaved bacteriophage genome, wherein the cleaved bacteriophage genome comprises genomic sequence that is downstream of the first site; (b) recombining in vitro the cleaved bacteriophage genome with a heterologous nucleic acid in the presence of a recombination system under conditions to produce a circularized recombinant bacteriophage genome; and (c) contacting the sample with at least one exonuclease to enrich for the circularized recombinant bacteriophage genome. In any of the above embodiments of the method, the heterologous nucleic acid comprises a 5' flanking region that is homologous to the 3' end of the cleaved bacteriophage genome, and a 3' flanking region that is homologous to the 5' end of the cleaved bacteriophage genome. In any of the above embodiments, the linear bacteriophage DNA genome may be recombinant or non-recombinant.

Additionally or alternatively, in some embodiments of the methods of the present technology, the at least one exonuclease is selected from the group consisting of Lambda exonuclease, Exonuclease III, RecBCD, Exonuclease VIII truncated, T5 exonuclease, and T7 exonuclease. The at least one exonuclease may be bidirectional or unidirectional. In some embodiments, the at least one exonuclease is RecBCD. In certain embodiments, the methods disclosed herein further comprise propagating the circularized recombinant bacteriophage genome in a bacterial host. The non-terminally redundant linear bacteriophage DNA genome may correspond to a bacteriophage family or order selected from the group consisting of Myoviridae, Styloviridae, Siphoviridae, Pedoviridae, Tectiviridae, Leviviridae, Podoviridae, and Plasmaviridae.

Additionally or alternatively, in some embodiments of the methods of the present technology, the recombination system comprises a 5'-3' exonuclease, a DNA polymerase, and a DNA ligase. In one embodiment, the 5'-3' exonuclease is T5 exonuclease, the DNA polymerase is Phusion® DNA polymerase (Thermo Fisher Scientific, Waltham, Mass.), and the DNA ligase is Taq ligase. In other embodiments, the recombination system comprises a 3'-5' exonuclease, a DNA polymerase, and a DNA ligase.

Additionally or alternatively, in some embodiments of the methods of the present technology, the CRISPR enzyme is a Cas protein selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4.

In any of the above embodiments of the methods disclosed herein, the heterologous nucleic acid comprises an open reading frame that encodes a bioluminescent protein, a fluorescent protein, a chemiluminescent protein, or any combination thereof. In certain embodiments, the open reading frame of the heterologous nucleic acid is operably linked to an expression control sequence that is capable of directing expression of the bioluminescent protein, the fluorescent protein, the chemiluminescent protein, or any combination thereof. In some embodiments, the expression control sequence is an inducible promoter or a constitutive promoter. The heterologous nucleic acid can be about 100-500 base pairs in length, about 500-1000 base pairs in length, 1000-1500 base pairs in length, about 1500-2000 base pairs in length, 2000-2500 base pairs in length, about 2500-3000 base pairs in length, 3000-3500 base pairs in length, or about 3500-4000 base pairs in length.

Examples of bioluminescent protein include, but are not limited to, Aequorin, firefly luciferase, *Renilla* luciferase, red luciferase, luxAB, and nanoluciferase. Examples of chemiluminescent protein include β-galactosidase, horseradish peroxidase (HRP), and alkaline phosphatase. Examples of fluorescent protein include, but are not limited to, TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOK, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherry1, PATagRFP, Kaede (green), Kaede (red), KikGR1 (green), KikGR1 (red), PS-CFP2, PS-CFP2, mEos2 (green), mEos2 (red), PSmOrange, or Dronpa.

Also disclosed herein are kits for integrating a heterologous nucleic acid sequence into a linear bacteriophage DNA genome.

BRIEF DESCRIPTION OF THE DRAWINGS

FIG. 3 shows the complete genome sequence of *Klebsiella* phage K11 (SEQ ID NO: 1).

DETAILED DESCRIPTION

Figure 1:
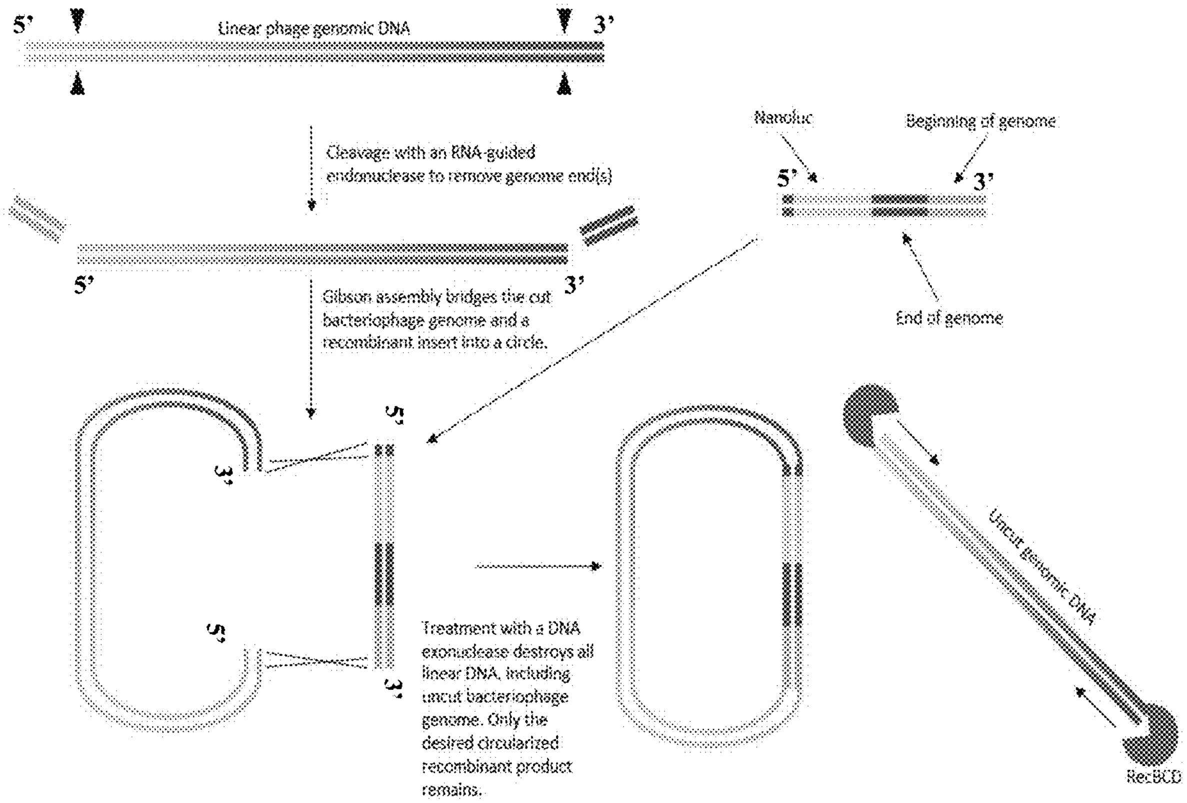
FIG. 1 shows the schematic representation of the circular payload integration method disclosed herein.

It is to be appreciated that certain aspects, modes, embodiments, variations and features of the present methods are described below in various levels of detail in order to provide a substantial understanding of the present technology.

Manipulating phage genomes is more difficult compared to manipulating bacterial hosts. In vitro synthesis and assembly of phage genomes is inefficient and relies on the delivery of large DNA molecules across the cell membranes of a bacterial host. Some bacterial strains are recalcitrant to large DNA transformation across the membrane. Classic in vivo recombination strategies are also inefficient and are complicated by the fact that lytic phage genomes have a comparatively short residence time in a host before lysis.

One of the most commonly used and well-established methods for engineering phage genomes is homologous recombination in their bacterial hosts, which can occur between two homologous DNA sequences as short as 23 bp (Alberts B et al., MOLECULAR BIOLOGY OF THE CELL, 5th ed. Garland Science, New York, N.Y. (2007); Snyder L et al., MOLECULAR GENETICS OF BACTERIA, 4th ed. ASM Press, Washington, D.C. (2013)). Homologous recombination occurs between the plasmid and the phage genome, allowing the heterologous gene to be integrated into the phage genome and eventually packaged within the phage particle. However, homologous recombination only yields a small fraction of recombinant progeny phage. Reported recombination rates range from $10^{-10}$ to $10^{-4}$ (Loessner M. et al., *Appl Environ Microbiol* 62:1133-1140 (1996); Le S. et al., *PLoS One* 8:e68562 (2013); Mahichi F. et al., *FEMS Microbiol Lett* 295:211-217 (2009)). One of the major challenges of generating recombinant bacteriophages is that the recombinant processes used to create such bacteriophages are inefficient, and often result in a low yield of recombinant bacteriophage genomes. Transformation of large bacteriophage genomes (e.g., about or greater than 40-48 kb) is prohibitive in many bacterial strains and species, making it difficult to isolate viable bacteriophage particles post-transformation. See e.g., Chauthaiwale et al., *Microbiological Reviews* 56 (4): 577-592 (1992); see also Vaughan et al., *Nature Biotechnology* 14:309-314 (1996). Thus, finding the desired clone using conventional phage screening methods is labor-intensive and unpredictable.

The present disclosure provides methods for integrating a heterologous nucleic acid sequence into a linear bacteriophage DNA genome, and isolating recombinant bacteriophages that express the heterologous nucleic acid sequence. The methods disclosed herein permit higher recovery of recombinant bacteriophage genomes that express the phenotypic properties associated with the heterologous nucleic acid sequence relative to that observed with other phage engineering methods, such as Break and Recombine 3.0 (BAR 3.0). For example, the overall yield of recombinant bacteriophage genomes obtained using the methods of the present technology was about 81% (13 out of 16 isolates). In contrast, no recombinant bacteriophages were generated using BAR 3.0 (i.e., 0% recovery of recombinant bacteriophage genomes).

In practicing the present methods, many conventional techniques in molecular biology, protein biochemistry, cell biology, microbiology and recombinant DNA are used. See, e.g., Sambrook and Russell eds. (2001) *Molecular Cloning: A Laboratory Manual,* 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual; Freshney* (2005) *Culture of Animal Cells: A Manual of Basic Technique,* 5th edition; Gait ed. (1984) *Oligonucleotide Synthesis*; U.S. Pat. No. 4,683,195; Hames and Higgins eds. (1984) *Nucleic Acid Hybridization*; Anderson (1999) *Nucleic Acid Hybridization*; Hames and Higgins eds. (1984) *Transcription and Translation; Immobilized Cells and Enzymes* (IRL Press (1986)); Perbal (1984) *A Practical Guide to Molecular Cloning*; Miller and Calos eds. (1987) *Gene Transfer Vectors for Mammalian Cells* (Cold Spring Harbor Laboratory); Makrides ed. (2003) *Gene Transfer and Expression in Mammalian Cells*; Mayer and Walker eds. (1987) *Immunochemical Methods in Cell and Molecular Biology* (Academic Press, London); and Herzenberg et al. eds (1996) *Weir's Handbook of Experimental Immunology.*

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, "bacteriophage" or "phage" refers to a virus that infects bacteria. Bacteriophages are obligate intracellular parasites that multiply inside bacteria by co-opting some or all of the host biosynthetic machinery (i.e., viruses that infect bacteria). Though different bacteriophages may contain different materials, they all contain nucleic acid and protein, and can under certain circumstances be encapsulated in a lipid membrane. Depending upon the phage, the nucleic acid can be either DNA or RNA (but not both) and can exist in various forms.

As used herein, "expression" includes one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

As used herein, an "expression control sequence" refers to polynucleotide sequences which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to encompass, at a minimum, any component whose presence is essential for expression, and can also encompass an additional component whose presence is advantageous, for example, leader sequences.

As used herein, "heterologous nucleic acid sequence" is any sequence placed at a location in the genome where it does not normally occur. A heterologous nucleic acid sequence may comprise a sequence that does not naturally occur in a bacteriophage, or it may comprise only sequences naturally found in the bacteriophage, but placed at a non-normally occurring location in the genome. In some embodiments, the heterologous nucleic acid sequence is not a natural phage sequence. In certain embodiments, the heterologous nucleic acid sequence is a natural phage sequence that is derived from a different phage. In other embodiments, the heterologous nucleic acid sequence is a sequence that occurs naturally in the genome of a wild-type phage but is then relocated to another site where it does not naturally occur, rendering it a heterologous sequence at that new site.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same nucleobase or amino acid, then the molecules are homologous at that position. A degree of homology between sequences is a function of the number of matching or homologous positions shared by the sequences. A polynucleotide or polynucleotide region (or a polypeptide or polypeptide region) has a certain percentage (for example, at least 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art. In some embodiments, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information. Biologically equivalent polynucleotides are those having the specified percent homology and encoding a polypeptide having the same or similar biological activity. Two sequences are deemed "unrelated" or "non-homologous" if they share less than 40% identity, or less than 25% identity, with each other.

As used herein, a "host cell" is a bacterial cell that can be infected by a phage to yield progeny phage particles. A host cell can form phage particles from a particular type of phage genomic DNA. In some embodiments, the phage genomic DNA is introduced into the host cell by infecting the host cell with a phage. In some embodiments, the phage genomic DNA is introduced into the host cell using transformation, electroporation, or any other suitable technique. In some embodiments, the phage genomic DNA is substantially pure when introduced into the host cell. In some embodiments, the phage genomic DNA is present in a vector when introduced into the host cell. The definition of host cell can vary from one phage to another. For example, *E. coli* may be the natural host cell for a particular type of phage, but *Klebsiella pneumoniae* is not.

As used herein, the term "isolated" refers to a substance or entity that has been separated from at least some of the components with which it was associated when initially produced (whether in nature or in an experimental setting). Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances and/or entities are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

As used herein, "operably linked" means that expression control sequences are positioned relative to the nucleic acid of interest to initiate, regulate or otherwise control transcription of the nucleic acid of interest.

As used herein, a "phage genome" includes naturally occurring phage genomes and derivatives thereof. Generally, the derivatives possess the ability to propagate in the same hosts as the naturally occurring phage. In some embodiments, the only difference between a naturally occurring phage genome and a derivative phage genome is at least one of a deletion and an addition of nucleotides from at least one end of the phage genome (if the genome is linear) or at least one point in the genome (if the genome is circular).

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, an endogenous nucleic acid sequence in the genome of an organism (or the encoded protein product of that sequence) is deemed "recombinant" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous to the organism (originating from the same organism or progeny thereof) or exogenous (originating from a different organism or progeny thereof). By way of example, a promoter sequence can be substituted (e.g., by homologous recombination) for the native promoter of a gene in the genome of an organism, such that this gene has an altered expression pattern. This gene would be "recombinant" because it is separated from at least some of the sequences that naturally flank it. A nucleic acid is also considered "recombinant" if it contains any modifications that do not naturally occur in the corresponding nucleic acid in a genome. For instance, an endogenous coding sequence is considered "recombinant" if it contains an insertion, deletion or a point mutation introduced artificially, e.g., by human intervention. A "recombinant nucleic acid" also includes a nucleic acid integrated into a host cell chromosome at a heterologous site and a nucleic acid construct present as an episome.

As used herein, a "recombinant bacteriophage genome" is a bacteriophage genome that has been genetically modified by the insertion of a heterologous nucleic acid sequence into the bacteriophage genome. A "recombinant bacteriophage" means a bacteriophage that comprises a recombinant bacteriophage genome. In some embodiments, the bacteriophage genome is modified by recombinant DNA technology to introduce a heterologous nucleic acid sequence into the genome at a defined site. In some embodiments, the heterologous nucleic acid sequence is introduced with no corresponding loss of endogenous phage genomic nucleotides. In other words, if bases N1 and N2 are adjacent in the wild-type bacteriophage genome, the heterologous nucleic acid sequence is inserted between N1 and N2. Thus, in the resulting recombinant bacteriophage genome, the heterologous nucleic acid sequence is flanked by nucleotides N1 and N2. In some embodiments, endogenous phage nucleotides are removed or replaced during the insertion of the heterologous nucleic acid sequence. For example, in some embodiments, the heterologous nucleic acid sequence is inserted in place of some or all of the endogenous phage sequence which is removed. In some embodiments, endogenous phage sequences are removed from a position in the phage genome distant from the site(s) of insertion of the heterologous nucleic acid sequences.

As used herein, the term "sample" refers to clinical samples obtained from a subject or isolated microorganisms. In certain embodiments, a sample is obtained from a biological source (i.e., a "biological sample"), such as tissue, bodily fluid, or microorganisms collected from a subject. Sample sources include, but are not limited to, mucus, sputum, bronchial alveolar lavage (BAL), bronchial wash (BW), whole blood, bodily fluids, cerebrospinal fluid (CSF), urine, plasma, serum, or tissue.

Bacteriophage

Bacteriophage are obligate intracellular parasites that multiply inside bacteria by co-opting some or all of the host biosynthetic machinery. Phages contain nucleic acid and protein, and may be enveloped by a lipid membrane. Depending upon the phage, the nucleic acid genome can be either DNA or RNA but not both, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances no more than 500,000 bp. The number and amount of individual types of protein in phage particles will vary depending upon the phage. The proteins function in infection and to protect the nucleic acid genome from environmental nucleases.

Phage genomes come in a variety of sizes and shapes (e.g., linear or circular). Most phages range in size from 24-200 nm in diameter. The capsid is composed of many copies of one or more phage proteins, and acts as a protective envelope around the phage genome. Many phages have tails attached to the phage capsid. The tail is a hollow tube through which the phage nucleic acid passes during infection. The size of the tail can vary and some phages do not even have a tail structure. In the more complex phages, the tail is surrounded by a contractile sheath which contracts during infection of the bacterial host cell. At the end of the tail, phages have a base plate and one or more tail fibers attached to it. The base plate and tail fibers are involved in the binding of the phage to the host cell.

Lytic or virulent phages are phages which can only multiply in bacteria and lyse the bacterial host cell at the end of the life cycle of the phage. The lifecycle of a lytic phage begins with an eclipse period. During the eclipse phase, no infectious phage particles can be found either inside or outside the host cell. The phage nucleic acid takes over the host biosynthetic machinery and phage specific mRNAs and proteins are produced. Early phage mRNAs code for early proteins that are needed for phage DNA synthesis and for shutting off host DNA, RNA and protein biosynthesis. In some cases, the early proteins actually degrade the host chromosome. After phage DNA is made late mRNAs and late proteins are made. The late proteins are the structural proteins that comprise the phage as well as the proteins needed for lysis of the bacterial cell. In the next phase, the phage nucleic acid and structural proteins are assembled and infectious phage particles accumulate within the cell. The bacteria begin to lyse due to the accumulation of the phage lysis protein, leading to the release of intracellular phage particles. The number of particles released per infected cell can be as high as 1000 or more. Lytic phage may be enumerated by a plaque assay. The assay is performed at a low enough concentration of phage such that each plaque arises from a single infectious phage. The infectious particle that gives rise to a plaque is called a PFU (plaque forming unit).

Lysogenic phages are those that can either multiply via the lytic cycle or enter a quiescent state in the host cell. In the quiescent state, the phage genome exists as a prophage (i.e., it has the potential to produce phage). In most cases, the phage DNA actually integrates into the host chromosome and is replicated along with the host chromosome and passed on to the daughter cells. The host cell harboring a prophage is not adversely affected by the presence of the prophage and the lysogenic state may persist indefinitely. The lysogenic state can be terminated upon exposure to adverse conditions. Conditions which favor the termination of the lysogenic state include: desiccation, exposure to UV or ionizing radiation, exposure to mutagenic chemicals, etc. Adverse conditions lead to the production of proteases (rec A protein), the expression of the phage genes, reversal of the integration process, and lytic multiplication.

In some embodiments, a phage genome comprises at least 5 kilobases (kb), at least 10 kb, at least 15 kb, at least 20 kb, at least 25 kb, at least 30 kb, at least 35 kb, at least 40 kb, at least 45 kb, at least 50 kb, at least 55 kb, at least 60 kb, at least 65 kb, at least 70 kb, at least 75 kb, at least 80 kb, at least 85 kb, at least 90 kb, at least 95 kb, at least 100 kb, at least 105 kb, at least 110 kb, at least 115 kb, at least 120 kb, at least 125 kb, at least 130 kb, at least 135 kb, at least 140 kb, at least 145 kb, at least 150 kb, at least 175 kb, at least 200 kb, at least 225 kb, at least 250 kb, at least 275 kb, at least 300 kb, at least 325 kb, at least 350 kb, at least 375 kb, at least 400 kb, at least 425 kb, at least 450 kb, at least 475 kb, or at least 500 kb of nucleic acids.

In certain embodiments, the linear bacteriophage DNA genomes correspond to a bacteriophage family or order selected from the group consisting of Myoviridae, Styloviridae, Siphoviridae, Pedoviridae, Tectiviridae, Leviviridae, Podoviridae, and Plasmaviridae. In some embodiments, the plurality of linear bacteriophage DNA genomes are derived from one or more bacteriophage genuses (or genera) selected from the group consisting of T7-like phage, phiKMV-like phage, LUZ24-like phage, phiKZ-like phage, PB1-like phage, Felix-O1-like phage, T4-like phage, phi92-like phage, rV5-like phage, SP6-like phage, N4-like phage, phiEco32-like phage, T5-like phage, KP34-like phage, KP15-like phage, GAP227-like phage, AP22-like phage, phiFel-like phage, Sap6-like phage, Silvia-like phage, Kay-like phage, Twort-like phage, P68-like phage, and phiETA-like phage.

Examples of bacteriophages with linear genomes useful in the methods of the present technology include *Klebsiella* phage K11, lambda phage, Enterobacteria phage T2, Enterobacteria phage T1, Enterobacteria phage T7, Enterobacteria phage T5, Enterobacteria phage P1, Enterobacteria phage PRD1, K1E phage, K1-5 phage, RB49 phage, RB16 phage, KP15 phage, KP27 phage, Miro phage, Matisse phage, phiEap-3 phage, ECP3 phage, EFDG1 phage, EFLK1 phage, vB_Efae230P-4 phage, vB_EfaP_IME195 phage, SA11 phage, Stau2 phage, K phage, G1 phage, SA12 phage, 812 phage, P68 phage, SAP-2 phage, 44AHJD phage, or SA97 phage.

Phase Engineering Methods of the Present Technology

In one aspect, the present disclosure provides a method for integrating a heterologous nucleic acid into a linear bacteriophage DNA genome comprising: (a) cleaving a first site at the 5' end of a plurality of linear bacteriophage DNA genomes and a second site at the 3' end of the plurality of linear bacteriophage DNA genomes with a CRISPR enzyme in vitro, wherein the plurality of linear bacteriophage DNA genomes is present in an isolated sample; (b) recombining in vitro the cleaved plurality of linear bacteriophage DNA genomes with the heterologous nucleic acid in the presence of a recombination system, wherein the heterologous nucleic acid comprises a 3' flanking region and a 5' flanking region that are homologous to the 5' and 3' ends of the cleaved plurality of linear bacteriophage DNA genomes respectively, thereby generating a plurality of circularized bacteriophage DNA genomes; and (c) enriching the plurality of circularized bacteriophage DNA genomes by incubating the sample with at least one exonuclease. The at least one exonuclease may be bidirectional or unidirectional. Additionally or alternatively, in some embodiments, the at least one exonuclease is selected from the group consisting of Lambda exonuclease, Exonuclease III, RecBCD, Exonuclease VIII truncated, T5 exonuclease, and T7 exonuclease. In some embodiments, the at least one exonuclease is RecBCD. In certain embodiments, the method further comprises propagating the plurality of circularized bacteriophage DNA genomes in a non-natural bacterial host. The plurality of linear bacteriophage DNA genomes may be recombinant or non-recombinant. In some embodiments, the linear bacteriophage DNA genome is a terminally redundant linear bacteriophage DNA genome.

In another aspect, the present disclosure provides a method for making an enriched plurality of recombinant circularized bacteriophage DNA genomes from a plurality of linear bacteriophage DNA genomes comprising: (a) contacting a sample comprising the plurality of linear bacteriophage DNA genomes with a first sgRNA-CRISPR enzyme complex and a second sgRNA-CRISPR enzyme complex in vitro under conditions where (i) the first sgRNA-CRISPR enzyme complex cleaves a first site at the 5' end of the plurality of linear bacteriophage DNA genomes; and (ii) the second sgRNA-CRISPR enzyme complex cleaves a second site at the 3' end of the plurality of linear bacteriophage DNA genomes; (b) recombining in vitro the cleaved plurality of linear bacteriophage DNA genomes with a heterologous nucleic acid in the presence of a recombination system under conditions to produce recombinant circularized bacteriophage DNA genomes; and (c) contacting the sample with at least one exonuclease to obtain an enriched plurality of recombinant circularized bacteriophage DNA genomes. The at least one exonuclease may be bidirectional or unidirectional. Additionally or alternatively, in some embodiments, the at least one exonuclease is selected from the group consisting of Lambda exonuclease, Exonuclease III, RecBCD, Exonuclease VIII truncated, T5 exonuclease, and T7 exonuclease. In some embodiments, the at least one exonuclease is RecBCD. The plurality of linear bacteriophage DNA genomes may be recombinant or non-recombinant.

The heterologous nucleic acid comprises a 3' flanking region and a 5' flanking region that are homologous to the 5' and 3' ends of the cleaved plurality of linear bacteriophage DNA genomes respectively. In certain embodiments, the first sgRNA-CRISPR enzyme complex comprises the sequence 5' GCCACCUGAGGUUAGACCAGGUUUUA-GAGCUAGAAAUAGCAAGUUAAAAUAA GGCUA-GUCCGUUAUCAACUUGAAAAAGUGGCACCGAGU-CGGUGCUUUUUUU 3' (SEQ ID NO:2), and the second gRNA-CRISPR enzyme complex comprises the sequence 5' GGCUACUUGGCGAUUUCUGCGUUUUAGAGCUA-GAAAUAGCAAGUUAAAAUAA GGCUAGU-CCGUUAUCAACUUGAAAAAGUGGCACCGAGUCG-GUGCUUUUUUU 3' (SEQ ID NO:3).

In some embodiments of the methods disclosed herein, the homologous 5' flanking region of the heterologous nucleic acid sequence has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the methods disclosed herein, the homologous 3' flanking region of the heterologous nucleic acid sequence has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

In certain embodiments, the plurality of linear bacteriophage DNA genomes correspond to a bacteriophage family or order selected from the group consisting of Myoviridae, Styloviridae, Siphoviridae, Pedoviridae, Tectiviridae, Leviviridae, Podoviridae, and Plasmaviridae. In some embodiments, the plurality of linear bacteriophage DNA genomes are derived from one or more bacteriophage genuses (or genera) selected from the group consisting of T7-like phage, phiKMV-like phage, LUZ24-like phage, phiKZ-like phage, PB1-like phage, Felix-O1-like phage, T4-like phage, phi92-like phage, rV5-like phage, SP6-like phage, N4-like phage, phiEco32-like phage, T5-like phage, KP34-like phage, KP15-like phage, GAP227-like phage, AP22-like phage, phiFel-like phage, Sap6-like phage, Silvia-like phage, Kay-like phage, Twort-like phage, P68-like phage, and phiETA-like phage.

Additionally or alternatively, in some embodiments, the plurality of linear bacteriophage DNA genomes correspond to *Klebsiella* phage K11, lambda phage, Enterobacteria phage T2, Enterobacteria phage T1, Enterobacteria phage T7, Enterobacteria phage T5, Enterobacteria phage P1, Enterobacteria phage PRD1, K1E phage, K1-5 phage, RB49 phage, RB16 phage, KP15 phage, KP27 phage, Miro phage, Matisse phage, phiEap-3 phage, ECP3 phage, EFDG1 phage, EFLK1 phage, vB_Efae230P-4 phage, vB_EfaP_IME195 phage, SA11 phage, Stau2 phage, K phage, G1 phage, SA12 phage, 812 phage, P68 phage, SAP-2 phage, 44AHJD phage, or SA97 phage.

In some embodiments of the methods disclosed herein, the plurality of linear bacteriophage DNA genomes correspond to *Klebsiella* phage K11, wherein the first site at the 5' end of the plurality of linear bacteriophage DNA genomes is after the nucleotide located at position 232 of SEQ ID NO:1 and the second site at the 3' end of the plurality of linear bacteriophage DNA genomes is after the nucleotide located at position 40,715 of SEQ ID NO:1. In certain embodiments, the CRISPR enzyme is Cas9 and is coupled to a sgRNA having the sequence 5' GCCACCUGAGGUUAGACCAGGUUUUAGAGCUAGAAAUAGCAAGUUAAAAUAA GGCUAGUCCGUUAUCAACUUGAAAAAGUGGCACCGAGUCGGUGCUUUUUUU 3' (SEQ ID NO:2) or 5' GGCUACUUGGCGAUUUCUGCGUUUUAGAGCUAGAAAUAGCAAGUUAAAAUAA GGCUAGUCCGUUAUCAACUUGAAAAAGUGGCACCGAGUCGGUGCUUUUUUU 3' (SEQ ID NO:3).

In another aspect, the present disclosure provides a method for integrating a heterologous nucleic acid into a non-terminally redundant linear bacteriophage DNA genome. In some embodiments, the method comprises: (a) contacting a sample comprising a linear bacteriophage DNA genome with a sgRNA-CRISPR enzyme complex in vitro under conditions where the sgRNA-CRISPR enzyme complex cleaves a first site at the 3' end of the linear bacteriophage DNA genome to produce a cleaved bacteriophage genome, wherein the cleaved bacteriophage genome comprises genomic sequence that is upstream of the first site; (b) recombining in vitro the cleaved bacteriophage genome with a heterologous nucleic acid in the presence of a recombination system under conditions to produce a circularized recombinant bacteriophage genome; and (c) contacting the sample with at least one exonuclease to enrich for the circularized recombinant bacteriophage genome. In other embodiments, the method comprises: (a) contacting a sample comprising a linear bacteriophage DNA genome with a sgRNA-CRISPR enzyme complex in vitro under conditions where the sgRNA-CRISPR enzyme complex cleaves a first site at the 5' end of the linear bacteriophage DNA genome to produce a cleaved bacteriophage genome, wherein the cleaved bacteriophage genome comprises genomic sequence that is downstream of the first site; (b) recombining in vitro the cleaved bacteriophage genome with a heterologous nucleic acid in the presence of a recombination system under conditions to produce a circularized recombinant bacteriophage genome; and (c) contacting the sample with at least one exonuclease to enrich for the circularized recombinant bacteriophage genome. In any of the above embodiments of the method, the heterologous nucleic acid comprises a 5' flanking region that is homologous to the 3' end of the cleaved bacteriophage genome, and a 3' flanking region that is homologous to the 5' end of the cleaved bacteriophage genome. In any of the above embodiments, the linear bacteriophage DNA genome may be recombinant or non-recombinant.

In some embodiments of the methods disclosed herein, the homologous 5' flanking region of the heterologous nucleic acid sequence has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the methods disclosed herein, the homologous 3' flanking region of the heterologous nucleic acid sequence has a length of about 20-30 base pairs (bps), 30-40 bps, 40-50 bps, 50-60 bps, 60-70 bps, 70-80 bps, 80-90 bps, 90-100 bps, 100-110 bps, 110-120 bps, 120-130 bps, 130-140 bps, 140-150 bps, 150-160 bps, 160-170 bps, 170-180 bps, 180-190 bps, 190-200 bps, 200-210 bps, 210-220 bps, 220-230 bps, 230-240 bps, 240-250 bps, 250-260 bps, 260-270 bps, 270-280 bps, 280-290 bps, 290-300 bps, 300-310 bps, 310-320 bps, 320-330 bps, 330-340 bps, 340-350 bps, 350-360 bps, 360-370 bps, 370-380 bps, 380-390 bps, 390-400 bps, 400-410 bps, 410-420 bps, 420-430 bps, 430-440 bps, 440-450 bps, 450-460 bps, 460-470 bps, 470-480 bps, 480-490 bps, 490-500 bps, 500-510 bps, 510-520 bps, 520-530 bps, 530-540 bps, 540-550 bps, 550-560 bps, 560-570 bps, 570-580 bps, 580-590 bps, or 590-600 bps.

Additionally or alternatively, in some embodiments of the methods of the present technology, the at least one exonuclease is selected from the group consisting of Lambda exonuclease, Exonuclease III, RecBCD, Exonuclease VIII truncated, T5 exonuclease, and T7 exonuclease. The at least one exonuclease may be bidirectional or unidirectional. In some embodiments, the at least one exonuclease is RecBCD. In certain embodiments, the methods disclosed herein further comprise propagating the circularized recombinant bacteriophage genome in a bacterial host. The non-terminally redundant linear bacteriophage DNA genome may correspond to a bacteriophage family or order selected from the group consisting of Myoviridae, Styloviridae, Siphoviridae, Pedoviridae, Tectiviridae, Leviviridae, Podoviridae, and Plasmaviridae.

Additionally or alternatively, in some embodiments of any of the methods disclosed herein, the recombination system comprises a 5'-3' exonuclease, a DNA polymerase, and a DNA ligase. In one embodiment, the 5'-3' exonuclease is T5 exonuclease, the DNA polymerase is Phusion® DNA polymerase (Thermo Fisher Scientific, Waltham, Mass.), and the DNA ligase is Taq ligase. In other embodiments, the recombination system comprises a 3'-5' exonuclease, a DNA polymerase, and a DNA ligase.

Accurate identification of bacterial species within a biological sample informs the selection of suitable therapies for treating bacterial infections. Recombinant bacteriophage generated using the methods disclosed herein, may be used to identify bacteria present within a biological sample (e.g., whole blood, plasma, serum). Such methods entail contacting the biological sample with a recombinant bacteriophage generated using the methods disclosed herein, and detecting the presence of bacterial host cells infected by the recombinant phage, wherein the recombinant phage comprises a heterologous nucleic acid that encodes a detectable gene product, thereby leading to the identification of bacteria present within the biological sample.

Additionally or alternatively, recombinant bacteriophage generated using the methods disclosed herein, may be used in methods for profiling antibiotic susceptibility of bacteria present within a biological sample (e.g., whole blood, plasma, serum). These methods include (a) contacting the biological sample with an antibiotic and a recombinant bacteriophage generated using the methods disclosed herein, (b) detecting the presence of bacterial host cells infected by the recombinant phage, wherein the recombinant phage comprises a heterologous nucleic acid that encodes a detectable gene product, and (c) determining that the antibiotic is effective in inhibiting the bacteria present in the biological sample when the number of recombinant phage infected bacterial host cells is reduced relative to that observed in an untreated control sample.

CRISPR Enzymes

A variety of CRISPR enzymes are available for use in conjunction with any of the methods of the present disclosure. In some embodiments, the CRISPR enzyme is a Type II CRISPR enzyme. In some embodiments, the CRISPR enzyme catalyzes DNA cleavage. In some embodiments, the CRISPR enzyme catalyzes RNA cleavage. In some embodiments, the CRISPR enzyme is any Cas9 protein, for instance any naturally-occurring bacterial Cas9 as well as any variants, homologs or orthologs thereof. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or variants thereof. In some embodiments, the CRISPR enzyme cleaves both strands of the target nucleic acid at the Protospacer Adjacent Motif (PAM) site.

Heterologous Nucleic Acids

In any of the above embodiments of the methods disclosed herein, the heterologous nucleic acid comprises an open reading frame that encodes a bioluminescent protein, a fluorescent protein, a chemiluminescent protein, or any combination thereof. In some embodiments, the encoded gene product(s) produces a detectable signal upon exposure to the appropriate stimuli, and the resulting signal permits detection of bacterial host cells infected by the recombinant phage. In certain embodiments, the open reading frame encodes a protein that serves as a marker that can be identified by screening bacterial host cells infected by a recombinant phage comprising a heterologous nucleic acid sequence comprising the open reading frame. Examples of such markers include by way of example and without limitation: a fluorescent label, a luminescent label, a chemiluminescence label, or an enzymatic label. In some embodiments, the heterologous nucleic acid sequence further comprises sequences naturally found in the bacteriophage, but placed at a non-normally occurring location in the genome.

In some embodiments of the methods disclosed herein, the length of the heterologous nucleic acid sequence is at least 100 bases, at least 200 bases, at least 300 bases, at least 400 bases, at least 500 bases, at least 600 bases, at least 700 bases, at least 800 bases, at least 900 bases, at least 1 kilobase (kb), at least 1.1 kb, at least 1.2 kb, at least 1.3 kb, at least 1.4 kb, at least 1.5 kb, at least 1.6 kb, at least 1.7 kb, at least 1.8 kb, at least 1.9 kb, at least 2.0 kb, at least 2.1 kb, at least 2.2 kb, at least 2.3 kb, at least 2.4 kb, at least 2.5 kb, at least 2.6 kb, at least 2.7 kb, at least 2.8 kb, at least 2.9 kb, at least 3.0 kb, at least 3.1 kb, at least 3.2 kb, at least 3.3 kb, at least 3.4 kb, at least 3.5 kb, at least 3.6 kb, at least 3.7 kb, at least 3.8 kb, at least 3.9 kb, at least 4.0 kb, at least 4.5 kb, at least 5.0 kb, at least 5.5 kb, at least 6.0 kb, at least 6.5 kb, at least 7.0 kb, at least 7.5 kb, at least 8.0 kb, at least 8.5 kb, at least 9.0 kb, at least 9.5 kb, at least 10 kb, or more. In certain embodiments, the heterologous nucleic acid sequence comprises a length that is less than or equal to a length selected from the group consisting of 1 kb, 2 kb, 3 kb, 4 kb, 5 kb, 6 kb, 7 kb, 8 kb, 9 kb, and 10 kb. In some embodiments, the heterologous nucleic acid sequence comprises a length that is less than or equal to the maximum length of heterologous nucleic acid sequence that can be packaged into a phage particle comprising the linear phage genome.

In some embodiments, the length of the heterologous nucleic acid sequence is from 100 to 500 bases, from 200 to 1,000 bases, from 500 to 1,000 bases, from 500 to 1,500 bases, from 1 kb to 2 kb, from 1.5 kb to 2.5 kb, from 2.0 kb to 3.0 kb, from 2.5 kb to 3.5 kb, from 3.0 kb to 4.0 kb, from 3.5 kb to 4.5 kb, from 4.0 kb to 5.0 kb, from 4.5 kb to 5.5 kb, from 5.0 kb to 6.0 kb, from 5.5 kb to 6.5 kb, from 6.0 kb to 7.0 kb, from 6.5 kb to 7.5 kb, from 7.0 kb to 8.0 kb, from 7.5 kb to 8.5 kb, from 8.0 kb to 9.0 kb, from 8.5 kb to 9.5 kb, or from 9.0 kb to 10.0 kb.

In some embodiments, the heterologous nucleic acid sequence is inserted into the linear phage genome with no loss of endogenous phage genomic sequence. In some embodiments, the heterologous nucleic acid sequence replaces an endogenous linear phage genomic sequence. In some embodiments, the heterologous nucleic acid sequence includes an endogenous linear phage genomic sequence that was previously excised from the linear phage genome.

In certain embodiments, the heterologous nucleic acid sequence replaces an endogenous linear phage genomic sequence that is less than the length of the heterologous nucleic acid sequence. Accordingly, in some embodiments, the length of the recombinant linear phage genome is longer than the length of the wild-type linear phage genome. In some embodiments, the heterologous nucleic acid sequence replaces an endogenous linear phage genomic sequence that is greater than the length of the heterologous nucleic acid sequence. Thus, in some embodiments, the length of the recombinant linear phage genome is shorter than the length of the wild-type linear phage genome. In certain embodiments, the heterologous nucleic acid sequence replaces an endogenous linear phage genomic sequence that is equal to the length of the heterologous nucleic acid sequence.

In certain embodiments, the open reading frame of the heterologous nucleic acid encodes a protein that confers a phenotype of interest on a host cell infected by a recombinant phage expressing the heterologous nucleic acid. In some embodiments, the phenotype of interest is the expression of the gene product encoded by the open reading frame of the heterologous nucleic acid.

In certain embodiments, the open reading frame of the heterologous nucleic acid is operably linked to an expression control sequence that is capable of directing expression of the open reading frame, wherein the open reading frame encodes a bioluminescent protein, a fluorescent protein, a chemiluminescent protein, or any combination thereof. In some embodiments, the expression control sequence is located within the heterologous nucleic acid sequence. In other embodiments, the expression control sequence is located in the endogenous linear phage genome sequence. For example, the open reading frame may be inserted into the linear phage genome downstream of or in the place of an endogenous phage open reading frame sequence. In some embodiments, the expression control sequence is an inducible promoter or a constitutive promoter (e.g., sarA promoter or lpp promoter). See e.g., Djordjevic & Klaenhammer, *Methods in Cell Science* 20(1):119-126 (1998). The inducible promoter or constitutive promoter may be an endogenous phage promoter sequence, a non-endogenous phage promoter sequence, or a bacterial host promoter sequence. Additionally or alternatively, in some embodiments, the inducible promoter is a pH-sensitive promoter, or a temperature sensitive promoter.

In some embodiments, the heterologous nucleic acid sequence comprises a first open reading frame and at least one supplemental open reading frame. In certain embodiments, the first and the at least one supplemental open reading frames are operably linked to the same expression control sequences. In some embodiments, the first and the at least one supplemental open reading frames are operably linked to different expression control sequences.

Fluorescent proteins include but are not limited to blue/UV fluorescent proteins (for example, TagBFP, Azurite, EBFP2, mKalama1, Sirius, Sapphire, and T-Sapphire), cyan fluorescent proteins (for example, ECFP, Cerulean, SCFP3A, mTurquoise, monomeric Midoriishi-Cyan, TagCFP, and mTFP1), green fluorescent proteins (for example, EGFP, Emerald, Superfolder GFP, Monomeric Azami Green, TagGFP2, mUKG, and mWasabi), yellow fluorescent proteins (for example, EYFP, Citrine, Venus, SYFP2, and TagYFP), orange fluorescent proteins (for example, Monomeric Kusabira-Orange, mKOK, mKO2, mOrange, and mOrange2), red fluorescent proteins (for example, mRaspberry, mCherry, dsRed, mStrawberry, mTangerine, tdTomato, TagRFP, TagRFP-T, mApple, and mRuby), far-red fluorescent proteins (for example, mPlum, HcRed-Tandem, mKate2, mNeptune, and NirFP), near-IR fluorescent proteins (for example, TagRFP657, IFP1.4, and iRFP), long stokes-shift proteins (for example, mKeima Red, LSS-mKate1, and LSS-mKate2), photoactivatable fluorescent proteins (for example, PA-GFP, PAmCherry1, and PATagRFP), photoconvertible fluorescent proteins (for example, Kaede (green), Kaede (red), KikGR1 (green), KikGR1 (red), PS-CFP2, PS-CFP2, mEos2 (green), mEos2 (red), PSmOrange, and PSmOrange), fluorescein, rhodamine, and photoswitchable fluorescent proteins (for example, Dronpa).

Examples of bioluminescent proteins are aequorin (derived from the jellyfish *Aequorea victoria*) and luciferases (including luciferases derived from firefly and *Renilla*, nanoluciferase, red luciferase, luxAB, and the like). These proteins have also been genetically separated into two distinct functional domains that will generate light only when the protein domains are closely co-localized. A variety of emission spectrum-shifted mutant derivatives of both of these proteins have been generated over the past decade and have been used for multi-color imaging and co-localization within a living cell.

Examples of chemiluminescent protein include β-galactosidase, horseradish peroxidase (HRP), and alkaline phosphatase. Peroxidases generate peroxide that oxidizes luminol in a reaction that generates light, whereas alkaline phosphatases remove a phosphate from a substrate molecule, destabilizing it and initiating a cascade that results in the emission of light.

In some embodiments, the open reading frame of the heterologous nucleic acid comprises an epitope that can be detected with an antibody or other binding molecule. For example, an antibody that recognizes the epitope may be directly linked to a signal generating moiety (such as by covalent attachment of a chemiluminescent or fluorescent protein), or can be detected using at least one additional binding reagent such as a secondary antibody, directly linked to a signal generating moiety. In some embodiments, the epitope is absent in wild-type bacteriophage and the bacterial host cell. Accordingly, detection of the epitope in a sample demonstrates the presence of a bacterial host cell infected by a recombinant phage comprising a heterologous nucleic acid, wherein the open reading frame of the heterologous nucleic acid comprises the epitope.

In other embodiments, the open reading frame of the heterologous nucleic acid comprises a polypeptide tag sequence, such that the expression product of the open reading frame comprises the tag fused to a polypeptide or protein encoded by the open reading frame (e.g., polyhistidine, FLAG, Glutathione S-transferase (GST) etc.).

In some embodiments, the open reading frame of the heterologous nucleic acid sequence comprises a biotin binding protein such as avidin, streptavidin, or neutrAvidin that can be detected with a biotin molecule conjugated to an enzyme (e.g., β-galactosidase, horseradish peroxidase (HRP), and alkaline phosphatase) or an antibody. In some embodiments, the antibody conjugated to a biotin molecule may be directly linked to a signal generating moiety (such as by covalent attachment of a chemiluminescent or fluorescent protein), or can be detected using at least one additional binding reagent such as a secondary antibody, directly linked to a signal generating moiety.

Kits

The present technology provides kits for integrating a heterologous nucleic acid sequence into a linear bacteriophage DNA genome.

In one aspect, the kits of the present technology comprise (a) one or more coded/labeled vials that contain a plurality of linear bacteriophage DNA genomes, (b) at least one CRISPR enzyme, (c) a recombination system, and (d) at least one exonuclease. The at least one exonuclease may be bidirectional or unidirectional. Additionally or alternatively, in some embodiments, the at least one exonuclease is selected from the group consisting of Lambda exonuclease, Exonuclease III, RecBCD, Exonuclease VIII truncated, T5 exonuclease, and T7 exonuclease. In certain embodiments, the at least one exonuclease is RecBCD. The plurality of linear bacteriophage DNA genomes may be recombinant or non-recombinant.

In some embodiments, each coded/labeled vial containing a plurality of linear bacteriophage DNA genomes corresponds to a different bacteriophage type. In other embodiments, each coded/labeled vial containing a plurality of linear bacteriophage DNA genomes corresponds to the same bacteriophage type. In some embodiments, each phage vial is assigned a unique code that identifies the bacteriophage in the phage vial, or the types of bacteria that the bacteriophage strain infects. The unique code can be encoded by a machine discernible pattern, such as a bar code, a QR code, an alphanumeric string, or any other pattern that can be discerned by a reader. Each unique code may be shown as, for example, a bar code sticker on a vial or container storing a corresponding phage sample. In some embodiments, the kit is stored under conditions that permit the preservation of the linear bacteriophage DNA genomes for extended periods, such as under bacteriophage-specific, controlled temperature, moisture, and pH conditions.

In some embodiments, the kits comprise a recombination system that includes a 5'-3' exonuclease, a DNA polymerase, and a DNA ligase. For example, in one embodiment, the 5'-3' exonuclease is T5 exonuclease, the DNA polymerase is Phusion® DNA polymerase (Thermo Fisher Scientific, Waltham, Mass.), and the DNA ligase is Taq ligase. In other embodiments, the kits comprise a recombination system that includes a 3'-5' exonuclease, a DNA polymerase, and a DNA ligase.

Additionally or alternatively, in some embodiments, the kits comprise one or more CRISPR enzymes selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. The one or more CRISPR enzymes may be coupled to a sgRNA. In certain embodiments, the sgRNA has the sequence 5' GCCACCUGAGGUUAGACCAGGUUUUAGAGCUAGAAAUAGCAAGUUAAAAUAA GGCUAGUCCGUUAUCAACUUGAAAAAGUGGCACCGAGUCGGUGCUUUUUUU 3' (SEQ ID NO:2) or 5' GGCUACUUGGCGAUUUCUGCGUUUUAGAGCUAGAAAUAGCAAGUUAAAAUAA GGCUAGUCCGUUAUCAACUUGAAAAAGUGGCACCGAGUCGGUGCUUUUUUU 3' (SEQ ID NO:3).

Additionally or alternatively, in some embodiments, the kits further comprise vials containing natural or non-natural bacterial host cells. In some embodiments, the bacterial host cells are *E. coli*. In certain embodiments, the bacterial host cells are *E. coli* strain DH10β.

In some embodiments, the kits further comprise positive control heterologous nucleic acid sequences to correct for any variability in the recombination systems between experimental runs. The kits may also comprise instructions for use, software for automated analysis, containers, packages such as packaging intended for commercial sale and the like.

The kit may further comprise one or more of: wash buffers and/or reagents, hybridization buffers and/or reagents, labeling buffers and/or reagents, and detection means. The buffers and/or reagents are usually optimized for the particular detection technique for which the kit is intended. Protocols for using these buffers and reagents for performing different steps of the procedure may also be included in the kit. Further optional components of the kits may include expression media for gene products encoded by the heterologous nucleic acids disclosed herein, such as a medium containing nutrients and cofactors for bioluminescence, devices such as a lamp configured to illuminate at specific wavelengths of light to detect biofluorescence, and devices for measuring the extent of heterologous nucleic acid expression, such as a photometer or photodetector.

Additionally or alternatively, the kits disclosed herein may also include coded and labeled vials that contain a plurality of antibiotics.

EXAMPLES

Example 1: Phage Engineering Methods of the Present Technology in *Klebsiella* Bacteriophage K11

This Example demonstrates that the methods of the present technology are useful for integrating a heterologous nucleic acid into a linear bacteriophage DNA genome (e.g., *Klebsiella* bacteriophage K11) and for isolating recombinant bacteriophages that express the heterologous nucleic acid sequence.

The *Klebsiella* phage K11 has a 41,181 base pair linear double-stranded DNA genome that is shown in FIG. 3 (GenBank Accession No. NC_011043, a.k.a, SEQ ID NO: 1). FIG. 1 shows the schematic representation of the circular payload integration method disclosed herein. SgRNAs complexed with *S. pyogenes* Cas9 endonuclease were used to generate double-stranded breaks after the nucleotide located at position 232, and after the nucleotide located at position 40,715 of phage K11 genomic DNA. The sgRNA sequences were 5' GCCACCUGAGGUUAGACCAGGUUUUAGAGCUAGAAAUAGCAAGUUAAAAUAA GGCUAGUCCGUUAUCAACUUGAAAAAGUGGCACCGAGUCGGUGCUUUUUUU 3' (SEQ ID NO:2) and 5' GGCUACUUGGCGAUUUCUGCGUUUUAGAGCUAGAAAUAGCAAGUUAAAAUAA GGCUAGUCCGUUAUCAACUUGAAAAAGUGGCACCGAGUCGGUGCUUUUUUU 3' (SEQ ID NO:3). The first 20 base pairs of each sgRNA represents the K11 phage sequence that was targeted. These cleavage sites were selected because they excised the very beginning and very end of the K11 genome. About 2.288 μg of K11 genomic DNA was digested with the Cas9:sgRNAs.

A heterologous nucleic acid sequence containing the nanoluciferase reporter gene was constructed. The heterologous nucleic acid sequence also included nucleotides 1-232, and 40,716-41,181 of the wild-type K11 phage genomic sequence. The 3' flanking region of the heterologous nucleic acid was homologous to the 5' end of the cleaved linear K11 phage genome, whereas the 5' flanking region of the heterologous nucleic acid was homologous to the 3' end of the cleaved linear K11 phage genome, thus facilitating recombination between the heterologous nucleic acid and the truncated linear K11 phage genome.

The cleaved linear K11 phage DNA and the heterologous nucleic acid sequence were subsequently joined together in a Gibson Assembly® (New England Biolabs, Ipswich, Mass.) reaction to form a circular recombinant phage genome. About 150 ng of the heterologous nucleic acid sequence (~2.3-fold molar excess) was added to the cleaved linear K11 phage DNA. The reaction was purified and about 1 μg total DNA was recovered. After completion of the Gibson Assembly® (New England Biolabs, Ipswich, Mass.) reaction, the K11 phage sample (which contained a mixture of circular recombinant K11 phage genome sequences and wild-type linear K11 phage genome sequences) was subjected to treatment with RecBCD, a bidirectional DNA exonuclease, according to the manufacturer's protocol. RecBCD degraded any unassembled wild-type linear phage genomic DNA, but did not affect the circularized recombinant phage genomic DNA. Next, 2 μL of the RecBCD treated reaction (about 67 ng total DNA) was transformed into the *E. coli* strain DH10β. Although not a natural host for the K11 phage, DH10β cells replicated the K11 phage genome and packaged fully infective recombinant phage particles that could be used to subsequently infect the native *Klebsiella pneumoniae* host.

Because most phages have mechanisms to resolve linear concatamers or circular replication intermediates, the recombinant circularized K11 phage genomes were converted into functional linear double-stranded DNA genomes that retained the heterologous nucleic acid sequence. Accordingly, the recombinant K11 phages contained nanoluciferase, a bioluminescent reporter that can be expressed in infected *Klebsiella pneumoniae* host cells. The phage engineering methods of the present technology yielded a total of 226 plaques.

Figure 2:
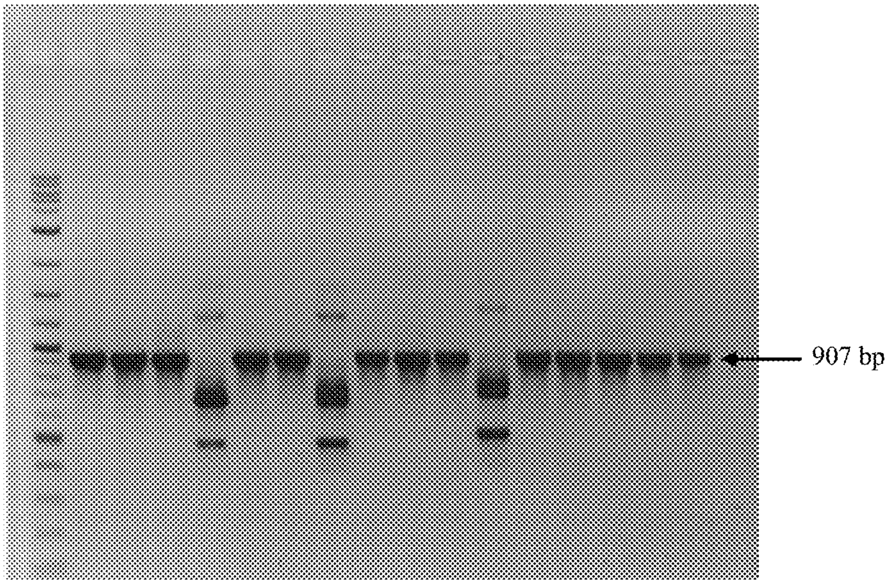
FIG. 2 shows the efficient recovery of recombinant bacteriophages containing the 907 base pairs (bp) nanoluciferase sequence using the methods of the present technology. Junctional PCR amplified a 907 bp product expected only in recombinant phages (13 out of 16 isolates). Primers span from inside the nanoluciferase insertion site to downstream of the nanoluciferase insert. The three isolates that yielded amplicons of different sizes correspond to viable phage that were incorrectly assembled during Gibson assembly or had otherwise incorporated an expanded or truncated insert.
Figure 4:
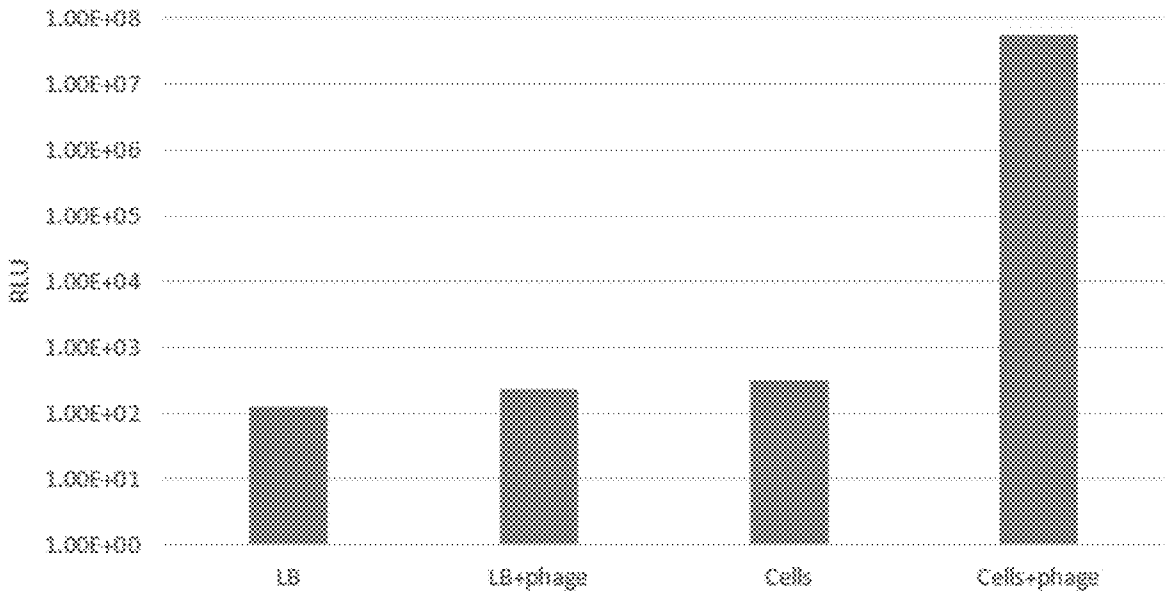
FIG. 4 shows the luminescence activity profile of a recombinant K11 phage. The recombinant K11 phage was picked and mixed into 25 μL of Tris-HCl with 10 mM $MgSO_4$ and was subsequently diluted by 1:100. 1 μL of diluted phage was added to 100 μL LB media, alone or in combination with 100 μL log-phase *K. pneumoniae* strain Kp390. Both the LB and *K. pneumoniae* cultures contained 10 mM $MgSO_4$. Paired negative controls that lacked phage were also included. The infections/mock infections were incubated at 37° C. for 1 hour.

A total of sixteen plaques were screened by PCR, out of which thirteen (81%) yielded the 907 bp amplicon that corresponded to the Nanoluciferase insert. See FIG. 2. Four of the thirteen plaques containing the recombinant K11 bacteriophage were tested on a host population of *Klebsiella pneumoniae*. The infected bacterial hosts displayed luminescence that was nearly five orders of magnitude above the background level. See FIG. 4.

These results demonstrate that the methods of the present technology permit the efficient recovery of recombinant linear bacteriophage DNA genomes that (a) contain a heterologous nucleic acid sequence of interest, and (b) express the phenotypic properties associated with the heterologous nucleic acid sequence of interest. Accordingly, the methods disclosed herein are useful for integrating heterologous nucleic acids into linear bacteriophage DNA genomes.

Example 2: Comparison Against BAR 3.0 Phage Engineering Method

This Example demonstrates that the methods of the present technology are useful for integrating a heterologous nucleic acid into a linear bacteriophage DNA genome (e.g., *Klebsiella* bacteriophage K11) and for isolating recombinant bacteriophages that express the heterologous nucleic acid sequence. Moreover, this Example demonstrates that the methods disclosed herein show superior efficiency with respect to recovering recombinant phage genomes compared to other phage engineering techniques, such as BAR 3.0.

Figure 5:
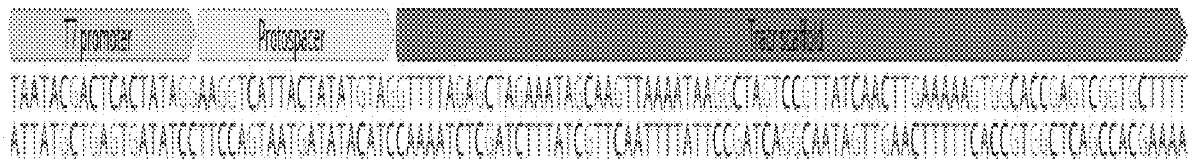
FIG. 5 shows the design of the K11 chimeric guide RNA expression construct used in the Break and Recombine 3.0 (BAR 3.0) experiments. Figure discloses SEQ ID NO: 4.

The CRISPR/Cas system was used to cleave the K11 phage genome after gene 4.5 to create an insertion site for a nanoluciferase reporter sequence into the phage genome. The desired chimeric guide sequence was placed under the control of a T7 promoter (FIG. 5) and was transcribed using the NEB HiScribe T7 High Yield RNA Synthesis Kit (NEB E2040, Ipswich, Mass.). The resulting RNA product was purified using the Qiagen RNeasy Mini Kit (Qiagen 74104, Hilden Germany).

The Cas9 endonuclease from New England Biolabs (NEB M0386, Ipswich, Mass.) was complexed with the sgRNA using a modified protocol. Briefly, in a 27 μL volume, 30 nM of sgRNA was incubated with 30 nM of Cas9 endonuclease. NEBuffer 3.1 was used instead of the included Cas9 Nuclease Reaction buffer. After a 10 minute preincubation at 25° C., 2.3 μg of K11 genomic DNA was added to the reaction to achieve a final concentration of 3 nM target DNA. The reaction was then incubated at 37° C. for 1 hr before adding an additional 3 nM Cas9 endonuclease. After incubation for another hour, 10 Units of RNAse A (ThermoFisher EN0351, Waltham, Mass.) was added to the reaction mixture to degrade any remaining RNA.

Figure 6:
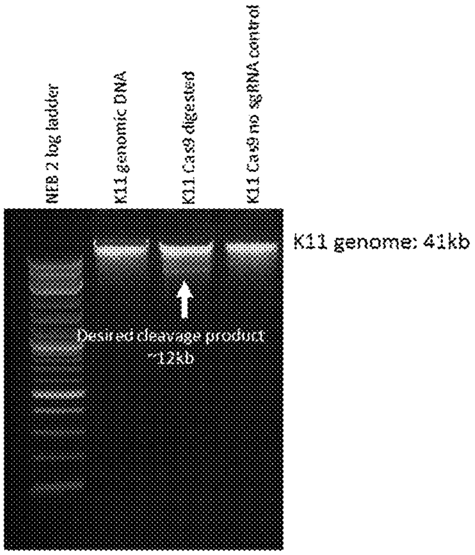
FIG. 6 shows a representative gel image of K11 genomic DNA after cleavage with the Cas9/sgRNA 4.5 complex.

After cleavage, the DNA was purified using phenol/chloroform precipitation. Cleavage of the K11 genomic DNA was verified using gel imaging. See FIG. 6.

Figure 7:
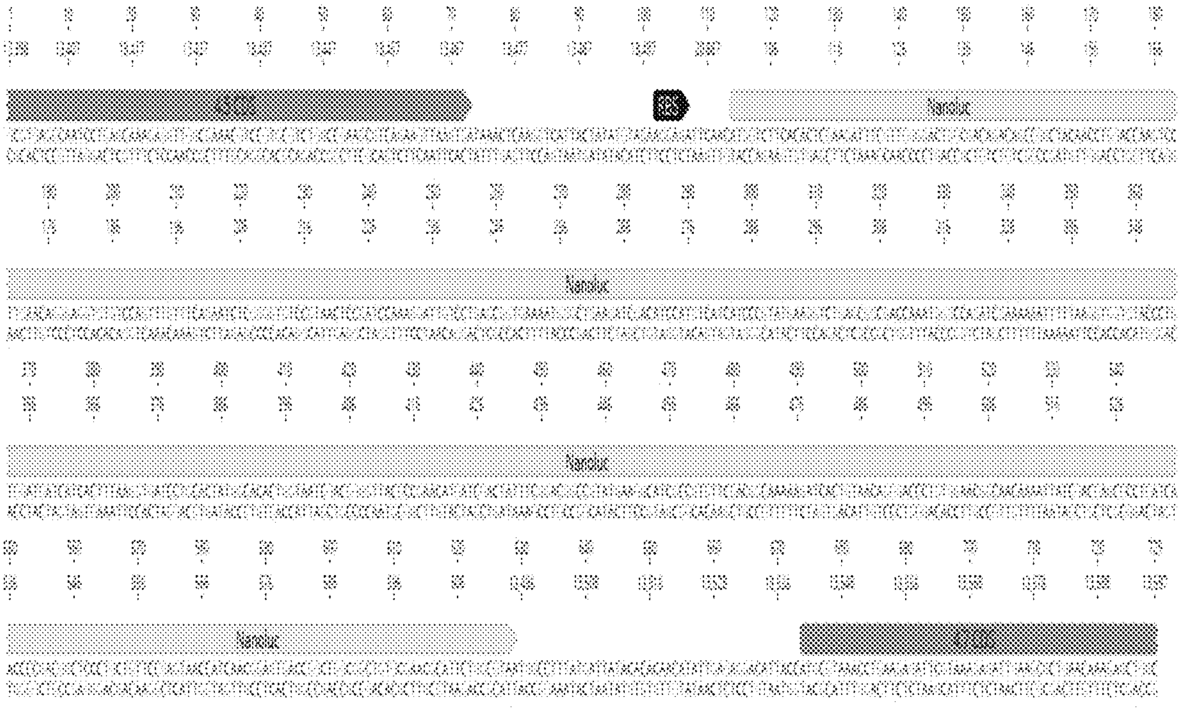
FIG. 7 shows the synthetic DNA construct used to introduce the nanoluciferase gene into the cleaved K11 genome via BAR 3.0. Figure discloses SEQ ID NO: 5.

A synthetic DNA construct containing 60 bp of homology to the K11 genome around the gene 4.5 cleavage site surrounding a nanoluciferase gene (FIG. 7) was introduced into the cleaved K11 phage genome using NEBuilder HiFi DNA assembly mix (NEB E5520, Ipswich, Mass.) according to the manufacturer's protocol. Briefly, 4 μg of cleaved K11 DNA was mixed with 90 ng of the nanoluc/K11 homology construct. The reaction was incubated at 50° C. for 60 minutes.

The reaction was subsequently purified using phenol/chloroform precipitation and 1 μg of the reaction product was electroporated into competent *Klebsiella pneumoniae* Sp 390 using the following electroporation settings: 200Ω resistance, 25 μF capacitance, and 2.4 kV. After electroporation, 400 μl of SOC broth was added to the cultures and cells were allowed to recover for one hour at 37° C. with shaking. Cells were then plated on a 0.65% soft agar overlay on an LB plate and incubated overnight at 37° C. Plaque formation was evaluated the following day. As shown in the Table below, no recombinant K11 bacteriophage were recovered using the BAR 3.0 protocol.

Electroplaquing Results for Cas9 cleaved K11 and recombined K11/nanoluciferase

| | 60 ng K11 DNA (uncleaved control) | 60 ng cleaved K11 DNA | 1 μg recombinant K11 phage with nanoluciferase insert |
|---|---|---|---|
| pfu/ml | 2.00E+08 | 0 | 0 |

These results demonstrate that the methods disclosed herein show superior efficiency with respect to recovering recombinant phage genomes compared to other phage engineering techniques, such as BAR 3.0. These results demonstrate that the methods of the present technology permit the efficient recovery of recombinant linear bacteriophage DNA genomes that (a) contain a heterologous nucleic acid sequence of interest, and (b) express the phenotypic properties associated with the heterologous nucleic acid sequence of interest. Accordingly, the methods disclosed herein are useful for integrating heterologous nucleic acids into linear bacteriophage DNA genomes.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for integrating a heterologous nucleic acid into a terminally redundant linear bacteriophage DNA genome comprising:

(a) cleaving a first site at the 5' end of a plurality of terminally redundant linear bacteriophage DNA genomes and a second site at the 3' end of the plurality of terminally redundant linear bacteriophage DNA genomes with a CRISPR enzyme in vitro, wherein the plurality of terminally redundant linear bacteriophage DNA genomes is present in an isolated sample;

(b) recombining in vitro the cleaved plurality of terminally redundant linear bacteriophage DNA genomes with the heterologous nucleic acid in the presence of a recombination system, wherein the heterologous nucleic acid comprises a 3' flanking region and a 5' flanking region that are homologous to the 5' and 3' ends of the cleaved plurality of terminally redundant linear bacteriophage DNA genomes respectively, thereby generating a plurality of circularized recombinant bacteriophage DNA genomes; and (c) enriching the plurality of circularized recombinant bacteriophage DNA genomes by incubating the sample with at least one exonuclease, wherein the heterologous nucleic acid encodes a non-endogenous protein, wherein the plurality of circularized recombinant bacteriophage genomes gives rise to recombinant bacteriophage particles that produce functionally active non-endogenous protein when transformed into a bacterial host cell, wherein the CRISPR enzyme is Cas9, and wherein the plurality of terminally redundant linear bacteriophage DNA genomes are selected from the group consisting of *Klebsiella* phage K11, Enterobacteria phage T7, and K15 phage.

2. The method of claim 1, further comprising propagating the plurality of circularized recombinant bacteriophage DNA genomes in a non-natural bacterial host.

3. The method of claim 1, wherein the at least one exonuclease is selected from the group consisting of Lambda exonuclease, Exonuclease III, RecBCD, Exonuclease VIII truncated, T5 exonuclease, and T7 exonuclease.

4. The method of claim 1, wherein the recombination system comprises a 5'-3' exonuclease, a DNA polymerase, and a DNA ligase.

5. The method of claim 1, wherein the recombination system comprises a 3'-5' exonuclease, a DNA polymerase, and a DNA ligase.

6. The method of claim 1, wherein the CRISPR enzyme is coupled to a sgRNA.

7. The method of claim 1, wherein the heterologous nucleic acid comprises an open reading frame that encodes a bioluminescent protein, a fluorescent protein, a chemiluminescent protein, or any combination thereof.

8. The method of claim 7, wherein the open reading frame of the heterologous nucleic acid is operably linked to an expression control sequence that is capable of directing expression of the bioluminescent protein, the fluorescent protein, the chemiluminescent protein, or any combination thereof.

9. The method of claim 8, wherein the expression control sequence is an inducible promoter or a constitutive promoter.

10. The method of claim 7, wherein the chemiluminescent protein is β-galactosidase, horseradish peroxidase (HRP), or alkaline phosphatase.

11. The method of claim 7, wherein the bioluminescent protein is Aequorin, firefly luciferase, *Renilla* luciferase, red luciferase, luxAB, or nanoluciferase.

12. The method of claim 7, wherein the fluorescent protein is TagBFP, Azurite, EBFP2, mKalama1, Sirius, Sapphire, T-Sapphire, ECFP, Cerulean, SCFP3A, mTurquoise, monomeric Midoriishi-Cyan, TagCFP, mTFP1, EGFP, Emerald, Superfolder GFP, Monomeric Azami Green, TagGFP2, mUKG, mWasabi, EYFP, Citrine, Venus, SYFP2, TagYFP, Monomeric Kusabira-Orange, mKOK, mKO2, mOrange, mOrange2, mRaspberry, mCherry, dsRed, mStrawberry, mTangerine, tdTomato, TagRFP, TagRFP-T, mApple, mRuby, mPlum, HcRed-Tandem, mKate2, mNeptune, NirFP, TagRFP657, IFP1.4, iRFP, mKeima Red, LSS-mKate1, LSS-mKate2, PA-GFP, PAmCherry1, PATagRFP, Kaede (green), Kaede (red), KikGR1 (green), KikGR1 (red), PS-CFP2, PS-CFP2, mEos2 (green), mEos2 (red), PSmOrange, or Dronpa.

* * * * *